(12) United States Patent
Hou et al.

(10) Patent No.: US 8,808,878 B2
(45) Date of Patent: Aug. 19, 2014

(54) COMPOUND AND USE THEREOF

(75) Inventors: Zhaomin Hou, Wako (JP); Yu Liu, Wako (JP)

(73) Assignee: RIKEN, Saitama (JP)

(*) Notice: Subject to any disclaimer, the term of this patent is extended or adjusted under 35 U.S.C. 154(b) by 534 days.

(21) Appl. No.: 13/131,444

(22) PCT Filed: Nov. 27, 2009

(86) PCT No.: PCT/JP2009/006425
§ 371 (c)(1),
(2), (4) Date: May 26, 2011

(87) PCT Pub. No.: WO2010/061625
PCT Pub. Date: Jun. 3, 2010

(65) Prior Publication Data
US 2011/0234089 A1 Sep. 29, 2011

(30) Foreign Application Priority Data

Nov. 28, 2008 (JP) ................................ 2008-304956
Jun. 5, 2009 (JP) ................................ 2009-136102

(51) Int. Cl.
*H01L 51/54* (2006.01)
*C09K 11/06* (2006.01)
*C07D 277/66* (2006.01)
*C07F 15/00* (2006.01)
*H01L 51/00* (2006.01)
*H01L 51/50* (2006.01)

(52) U.S. Cl.
CPC ..... *C07F 15/0033* (2013.01); *C09K 2211/1037* (2013.01); *C09K 11/06* (2013.01); *C09K 2211/1011* (2013.01); *C09K 2211/1092* (2013.01); *H01L 51/0081* (2013.01); *C09K 2211/1029* (2013.01); *C09K 2211/185* (2013.01); *C07D 277/66* (2013.01); *H01L 51/0085* (2013.01); *C09K 2211/1033* (2013.01); *H01L 2251/308* (2013.01); *H01L 51/5016* (2013.01); *Y10S 428/917* (2013.01)
USPC ........... 428/690; 428/917; 303/504; 303/506; 252/301.16; 257/40; 257/E51.044; 546/4; 548/103

(58) Field of Classification Search
None
See application file for complete search history.

(56) References Cited

U.S. PATENT DOCUMENTS

| | | | |
|---|---|---|---|
| 2004/0253477 A1 | 12/2004 | Kathirgamanathan et al. | |
| 2004/0265633 A1* | 12/2004 | Son et al. ................ | 428/690 |
| 2006/0069275 A1 | 3/2006 | Eberhardt et al. | |
| 2007/0292631 A1 | 12/2007 | Shinozaki et al. | |
| 2009/0058286 A1 | 3/2009 | Koyama et al. | |
| 2010/0213824 A1 | 8/2010 | Adler et al. | |
| 2010/0320449 A1 | 12/2010 | Schmid | |

FOREIGN PATENT DOCUMENTS

| | | |
|---|---|---|
| CN | 1720254 A | 1/2006 |
| CN | 101182412 | 5/2008 |
| CN | 101280186 | 10/2008 |
| JP | 2003-264086 | 9/2003 |
| JP | A-2004-349224 | 12/2004 |
| JP | 2006-131561 | 5/2006 |
| JP | 2006-147549 | 6/2006 |
| JP | 2007-145897 | 6/2007 |
| JP | 2007-266071 | 10/2007 |
| JP | 2010-540701 A | 12/2010 |
| WO | WO 2005/118606 | 12/2005 |

OTHER PUBLICATIONS

International Search Report for PCT/JP2009/006425, mailed Jan. 19, 2010.
Villa, J. M. et al., "Cyclometallated Complexes of Palladium(li) With 1-Methyl-2-Phenylimidazole and Tertiary Diphosphines. Crystal and Molecular Structure of [{Pd[O-$C_6h_4$c=Nc(H)=C(H)Nme]}($Ph_2$pch(Me)$Pph_2$-P,P)][$Pf_6$)", Journal of Organomettalic Chemistry 547, (1997), pp. 297-307.
Lamansky, S. et al., "Synthesis and Characterization of Phosphorescent Cyclometalated Iridium Complexes", Inorg. Chem., 40, (2001), pp. 1704-1711.
Wang et al., "Highly Efficient Electroluminescent Materials Based on Fluorinated Organomettalic Iridium Compounds", Applied Physics Letters, vol. 79, No. 4, (Jul. 23, 2001), pp. 449-451.
Holmes, R.J. et al I., "Efficient, Deep Blue Organic Electrophosphorescence by Guest Charge Trapping", Applied Physics Letters, vol. 83, No. 18, (Nov. 3, 2003), pp. 3818-3820.
Song, Y-H et al., "Bright and Efficient, Non-Doped, Phosphorescent Organic Red-Light-Emitting Diodes", Adv. Funct. Mater., 14, 12, (Dec. 2004), pp. 1221-1226.

(Continued)

*Primary Examiner* — Michael H Wilson
(74) *Attorney, Agent, or Firm* — Nixon & Vanderhye PC

(57) ABSTRACT

A compound according to the present invention is represented by the general formula (1):

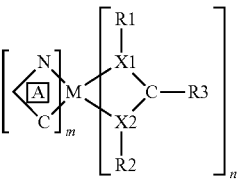

as defined herein. This makes it possible to provide (i) a novel compound that exhibits a practically sufficient light-emitting property not only in a case where the novel compound is used as a luminescent dopant, but also in a case where the novel compound is used solely, and (ii) use of the novel compound.

15 Claims, 29 Drawing Sheets

(56) References Cited

OTHER PUBLICATIONS

Liu, Z. et al., "Red Phosphorescent Iridium Complex Containing Carbazole-Functionalized B-Diketonate for Highly Efficient Nondoped Organic Light-Emitting Diodes", Adv. Func. Mater., No. 16, (2006), pp. 1441-1448.

Zhi, H. et al., "Reduction of Self-Quenching Effect in Organic Electrophosphorescence Emitting Devices Via the Use of Sterically Hindered Spacers in Phosporescence Molecules", Advanced Materials, (4 pages), 2001.

Jung, S. et al., "Effect of Substitution of Methyl Groups on the Luminescence Performance of Ir" Complexes: Preparation, Structures, Electrochemistry, Photophysical Properties and Their Applications in Organic Light-Emitting Diodes (Oleds), Eur. J. Inorg. Chem., (2004), pp. 3415-3423.

Tamayo, B. et al., "Synthesis and Characterization of Facial and Meridional Tris-Cyclometalated Iridium(III) Complexes", J. Am. Chem. Soc, No. 125, (2003), pp. 7377-7387.

Lamansky, S. et al., "Highly Phosphorescent Bis-Cyclometalated Iridium Complexes: Synthesis, Photophysical Characterization, and Use. In Organic Light Emitting Diodes", J. Am. Chem. Soc., No. 123, (2001), pp. 4304-4312.

Adachi, C. et al., "Nearly 100% Internal Phosphorescence Efficiency in an Organic Light Emitting Device", Journal of Applied Physics, vol. 90, No. 10, (Nov. 15, 2001), pp. 5048-5051.

Nazeeruddin, M.K. et al., "Highly Phosphorescence Iridium Complexes and Their Application in Organic Light-Emitting Devices", J. Am Chem. Soc., vol. 125, (2003), pp. 8790-8797.

Duan, J-P et al., "New Iridium Complexes As Highly Efficient Orange-Red Emitters in Organic Light-Emitting Diodes", Adv. Mater., vol. 15, No. 3, (Feb. 5, 2003), pp. 224-228.

Chien, C-H et al., "Elecrophosphorescent Polyfluorenes Containing Osmium Complexes in the Conjugated Backbone", Adv. Func. Mater., vol. 18, (2008), pp. 1430-1439.

Ding, J. et al I., "Solution-Processible Red Iridium Dendrimers Based on Oligocarbazole Host Dendrons: Synthesis, Properties, and Their Applications in Organic Light-Emitting Diodes", Adv. Func. Mater., vol. 18, (2008), pp. 2754-2762.

Tai Peng et al. "Very high-efficiency red-electroluminescence devices based on an amidinate-ligated phosphorescent iridium complex" Journal of Materials Chemistry 2009, 19, p. 8072-8074.

Chem. Comm., Jul. 7, 2009, No. 25, "Amidinate-ligated iridium(III) bis(2-pyridyl)phenyl complex as an excellent phosphorent material for electroluminescence devices", Yu Liu et al., pp. 3699-3701.

Int'l Search Report for PCT/JP2009/006425, three pages, mailed Jan. 19, 2010.

Written Opinion for PCT/ JP2009/006425, six pages, mailed Jan. 19, 2010.

Int'l Preliminary Report on Patentability for PCT/ JP2009/006425, eight pages, mailed Jul. 5, 2011.

Chen et al. "Novel, highly efficient blue-emitting heteroleptic iridium (III) complexes based on fluorinated 1,3,4-oxadiazole: Tuning to blue by dithiolate ancillary ligands" Chem. Commun. 1352-1354 (2007).

English translation of JPO's Office Action for JP 2010-540385, eight pages, mailed Feb. 12, 2014.

\* cited by examiner

COMPOUND AND USE THEREOF

This application is the U.S. national phase of International Application No. PCT/JP2009/006425 filed 27 Nov. 2009, which designated the U.S. and claims priority to JP Application No. 2008-304956, filed 28 Nov. 2008; and JP Application No. 2009-136102, filed 5 Jun. 2009, the entire contents of each of which are hereby incorporated by reference.

TECHNICAL FIELD

The present invention related to a novel compound and use of the compound. More specifically, the present invention relates to a light-emitting device including the compound.

BACKGROUND ART

Organic light-emitting devices (hereinafter referred to as "OLEDs") containing a phosphorescent metal complex as a luminescent material have luminous efficiency markedly higher than that of light-emitting devices containing a fluorescent material. In view of this, the OLEDs attract much attention.

Among heavy-metal complexes such as platinum, osmium, and iridium, which can be used as the luminescent material, the iridium complex has the highest luminous efficiency.

However, in order to obtain high-performance OLEDs, an iridium complex (luminescent dopant) should be doped on a base material of a luminescent host such as 4,4'-N,N'-dicarbazole-biphenyl (hereinafter referred to as "CBP") or the like while the iridium complex is precisely controlled at a low concentration within a certain concentration range (for example, 6% by weight to 10% by weight).

That is, the production of the high-performance OLEDs requires careful control of production steps to optimize a doping amount of the luminescent dopant. Further, there is a problem that prolonged use of such OLEDs causes phase separation between the luminescent host and the luminescent dopant.

In view of this, instead of this type of OLEDs (hereinafter referred to as "doped OLEDs") in which the luminescent dopant is doped on the luminescent host, another type of OLEDs (hereinafter referred to as "non-doped OLEDs") in which the luminescent dopant is not doped on the luminescent host is being developed. If non-doped OLEDs that practically exhibit sufficient performance can be produced, it is unnecessary to take account of such problems as the precise control of a doping amount and the phase separation.

Even if the non-doped OLEDs are produced by use of a conventional luminescent dopant, the performance of the non-doped OLEDs is at least about one order of magnitude lower than best-performance doped OLEDs in terms of obtainable luminance and luminous efficiency (see Non-patent Literature 1). This problem is presumably attributable to at least one of the following common characteristics among phosphorescent materials: (i) carrier (charge) transfer is extremely poor; and (ii) self-quenching is caused.

In view of this, as reported in Non-patent Literatures 2 to 5, novel phosphorescent materials suitable for the non-doped OLEDs are been developed.

Further, as reported in Non-patent Literature 6, an attempt to decrease self-quenching by introducing a stereocontrol spacer into a phosphorescent material is being also made.

CITATION LIST

Non-Patent Literature

Non-patent Literature 1
S. Lamansky et al.: J. Am. Chem. Soc. 2001, 123, 4304.
Non-patent Literature 2
Y. Wang et al.: Appl. Phys. Lett. 2001, 79, 449.
Non-patent Literature 3
R. J. Holmes et al.: Appl. Phys. Lett 2003, 83, 3818.
Non-patent Literature 4
Y. H. Song et al.: Adv. Func. Mater. 2004, 14, 1221.
Non-patent Literature 5
Z. W. Liu et al.: Adv. Func. Mater. 2006, 16, 1441.
Non-patent Literature 6
H. Z. Xie et al.: Adv. Mater. 2001, 13, 1245.

SUMMARY OF INVENTION

Technical Problem

However, most of the phosphorescent materials disclosed in Non-patent Literatures 2 to 5 have problems that they are produced by very complicated synthetic pathways and that their performances are far from a practical level.

Further, it cannot be said that the phosphorescent material disclosed in Non-patent Literature 6 is easily synthesized or its performance is sufficient in terms of practical use.

The present invention is accomplished in view of the above problems. An object of the present invention is to provide (i) a novel compound that exhibits a practically sufficient light-emitting property not only in a case where the compound is used as a luminescent dopant but also in a case where the compound is solely used, and (ii) use of the novel compound.

Solution to Problem

Inventors of the present invention conducted diligent study to solve the above problems. As a result of their diligent study, they found a fact that with the use of an ancillary ligand having a specific structure, a compound exhibiting an excellent phosphorescent property can be obtained. On the basis of the fact, they achieved the present invention.

That is, in order to achieve the above object, a compound according to the present invention is a compound represented by a general formula (1) as below. With the above arrangement, it is possible to produce a novel compound that exhibits a practically sufficient light-emitting property not only in a case where the compound is used as a luminescent dopant, but also in a case where the compound is used solely. Here, the general formula (1) is as follows:

[Chem. 1]

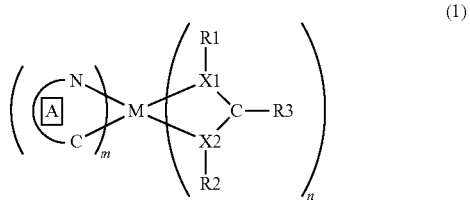

(1)

(In the formula (1), C^N (indicated by A) represents a cyclometalating ligand; M represents a transition metal atom; X1 and X2 each independently represent a nitrogen atom, an oxygen atom, a sulfur atom, or a phosphorous atom; R1 and R2 each independently represent a straight, branched, or cyclic alkyl group, an aryl group, an aralkyl group, or an ether group, which groups may have a substituent; R3 represents a straight, branched, or cyclic alkyl group, an alkenyl group, an alkynyl group, an aryl group, an aralkyl group, an aliphatic, aromatic, or cyclic amino group, a phosphino group, a boryl group, an alkylthio group, an arylthio group, an alkoxy group, an aryloxy group, an ether group, or an imino group, which groups may have a substituent; and m and n each independently represent an integer of not less than 1, and a total of m and n is not more than the largest number of ligands that can coordinate with M.)

A compound according to the present invention is more preferably a compound represented by the following general formula (2) or (3):

[Chem. 2]

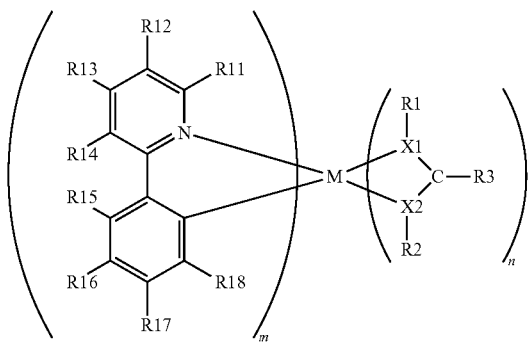

(2)

(In the formula (2), the definitions of M, X1, X2, R1, R2, R3, m, and n are the same as those in the general formula (1); R11 to R18 each independently represent a hydrogen atom, a halogen atom, or a C1 to C10 hydrocarbon group; at least one hydrogen included in the hydrocarbon group may be substituted with a halogen atom; in a case where the hydrocarbon group includes at least two carbon atoms, the at least two carbon atoms may be partially substituted with a sulfur atom or a nitrogen atom; and hydrocarbon groups may be connected to each other so as to form a ring.)

[Chem. 3]

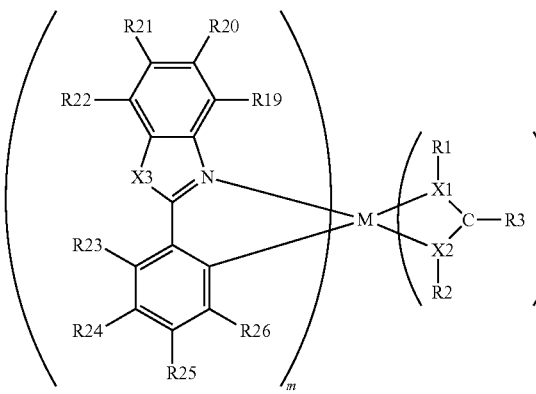

(3)

(In the formula (3), the definitions of M, X1, X2, R1, R2, R3, m, and n are the same as those in the general formula (1); X3 represents a sulfur atom or an oxygen atom; R19 to R26 each independently represent a hydrogen atom, a halogen atom, or a C1 to C10 hydrocarbon group; at least one hydrogen included in the hydrocarbon group may be substituted with a halogen atom; in a case where the hydrocarbon group includes at least two carbon atoms, the at least two carbon atoms may be partially substituted with a sulfur atom or a nitrogen atom; and hydrocarbon groups may be connected to each other so as to form a ring.)

Further, the compound according to the present invention is preferably arranged such that M represents iridium, and X1 and X2 each represent a nitrogen atom in the above formula.

The compound according to the present invention is more preferably arranged such that X3 represents a sulfur atom in the above formula.

A light-emitting method according to the present invention is a method for causing the compound according to the present invention to emit light by applying a voltage thereto.

A light-emitting device according to the present invention is a light-emitting device including a pair of electrodes, and an emitting layer containing a luminescent material and provided between the pair of electrodes, the emitting layer containing the compound according to the present invention. With the above arrangement, it is possible to provide a light-emitting device that exhibits a practically sufficient light-emitting property.

It is preferable that the light-emitting device according to the present invention contain only the compound according to the present invention as the luminescent material. With this arrangement, it is possible to provide a light-emitting device in which an emitting layer can be easily formed and in which quality deterioration is less likely to happen.

Advantageous Effects of Invention

In accordance with a compound according to the present invention and use thereof, it is advantageously possible to provide (i) a novel compound that exhibits a practically sufficient light-emitting property not only in a case where the compound is used as a luminescent dopant but also in a case where the compound is solely used, (ii) a light-emitting method using the compound, and (III) a light-emitting device using the compound.

BRIEF DESCRIPTION OF DRAWINGS (a) and (b) of FIG. 1 are views schematically illustrating crystal packing of compounds according to the present invention.

DESCRIPTION OF EMBODIMENTS

Figure 1:
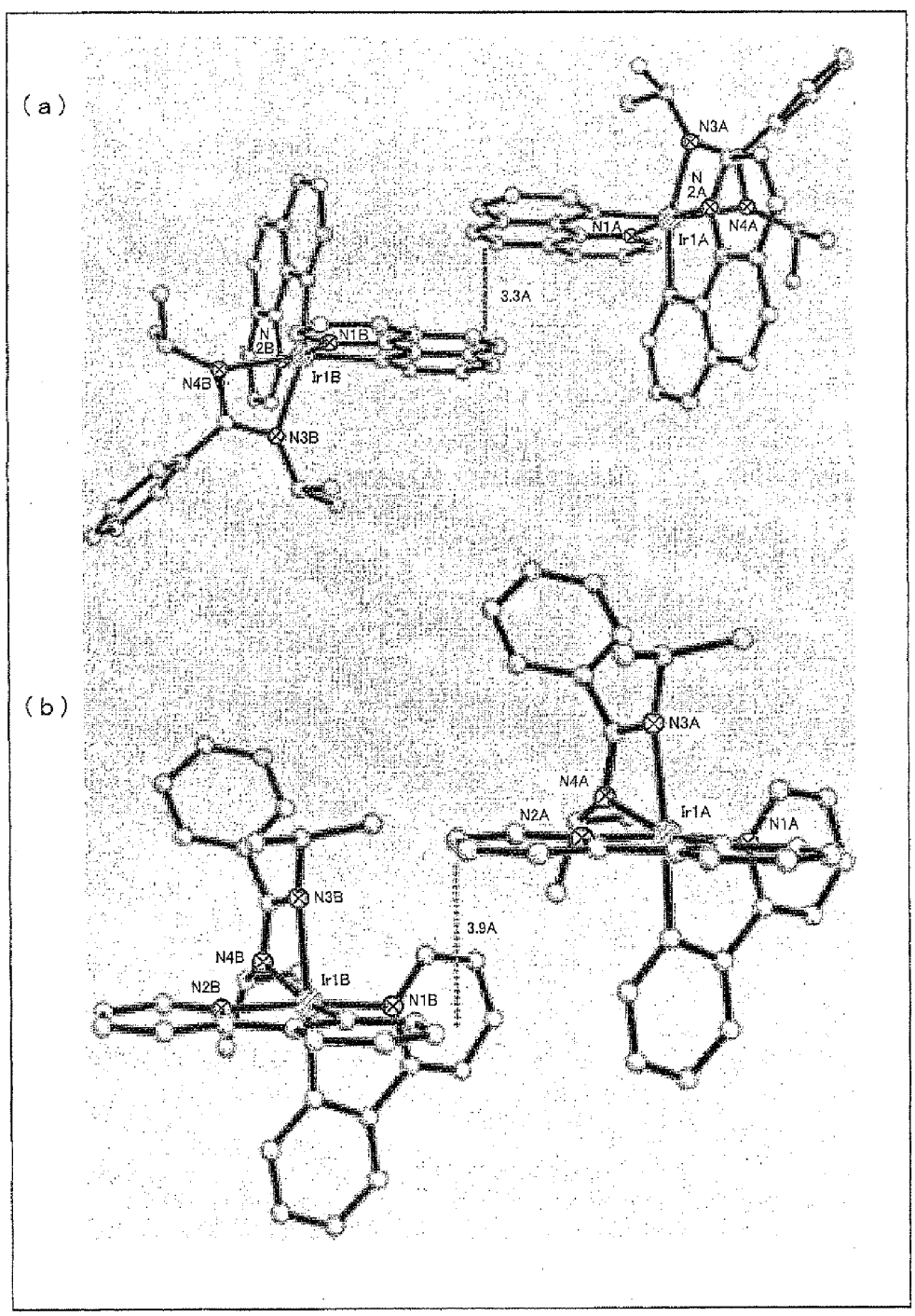

The following describes an embodiment of the present invention, more specifically.

[Novel Compound According to the Present Invention]

A novel compound according to the present invention is a compound having a structure represented by the following general formula (1):

[Chem. 4]

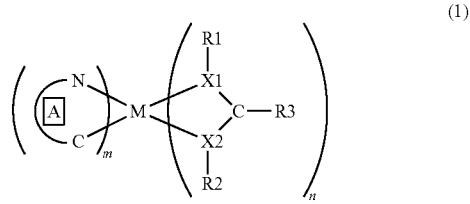

(1)

In the formula (1), C^N (hereinafter referred to as A) represents a cyclometalating ligand. In a case where there are a plurality of portions indicated by A (that is, the after-mentioned "m" is an integer of 2 or more), the plurality of portions indicated by A may represent the same cyclometalating ligand or different cyclometalating ligands from each other.

From the viewpoint of easy synthesis of the novel compound and enhancement of a light-emitting property of the compound, it is preferable that the plurality of portions indicated by A be the same cyclometalating ligand. A portion corresponding to the cyclometalating ligand mainly functions as a portion (a luminescent ligand) that is directly related to a luminous phenomenon in the novel compound according to the present invention. That is, the portion corresponding to the cyclometalating ligand functions as a portion that emits light (phosphorescence) from triplet excited state.

As the cyclometalating ligand, any ligand that is known as a ligand that is directly related to a luminous phenomenon of a metal complex can be employed, and a suitable ligand may be selected depending on what kind of light-emitting property (emission wavelength and the like) is intended. The cyclometalating ligand is not especially limited. Examples of the cyclometalating ligand encompass cyclometalating ligands represented by (a) to (q) in the following chemical formulae (4). In the chemical formulae (4), a hydrogen atom in an aromatic ring or a heterocyclic ring, or a hydrogen atom binding to any other carbon may be substituted with, for example, any one of the following substituents: a halogen group such as a fluorine atom, a chlorine atom, a bromine atom, or an iodine atom; a hydrocarbon group such as a C1 to C20, preferably, C1 to C6 alkyl group; a halogenated hydrocarbon group such as a C1 to C20, preferably, C1 to C6 halogenated alkyl group; an amino group; an alkoxy group; a thioalkoxy group; an aromatic ring, a heterocyclic ring, or a saturated or unsaturated hydrocarbon ring, and the like. Further, the cyclometalating ligands shown in the chemical formulae (4) may further have one or several aromatic rings, heterocyclic rings, saturated or unsaturated hydrocarbon rings, or the like cyclic structures.

[Chem. 5]

(4)

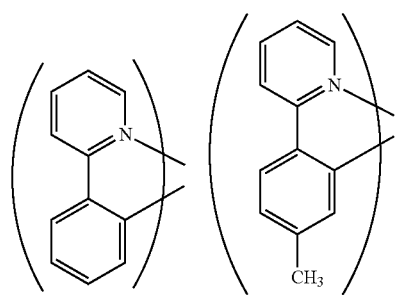

(a) (b)

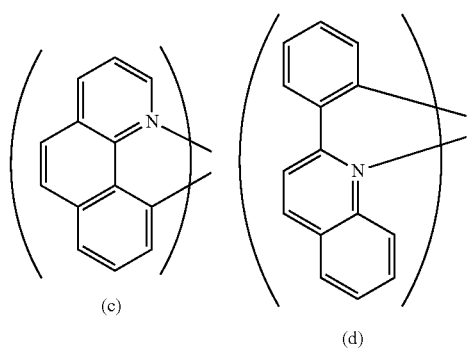

(c) (d)

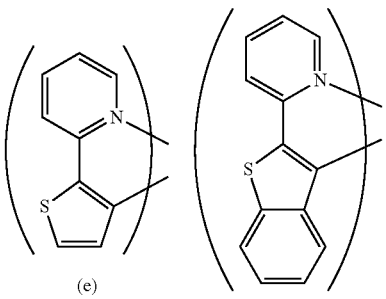

(e) (f)

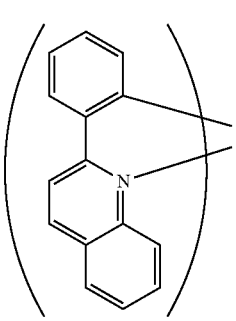 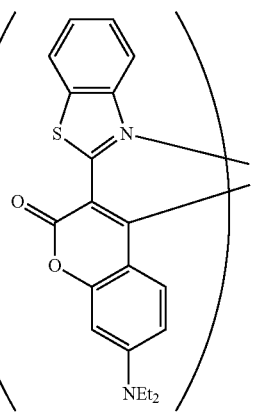

(g) (h)

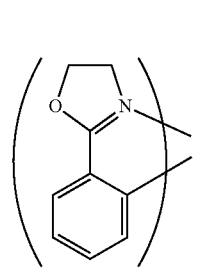 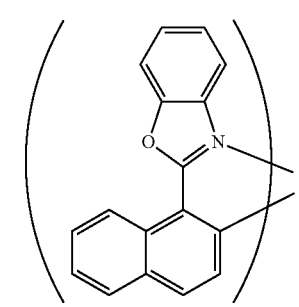

(i) (j)

(k) (l)

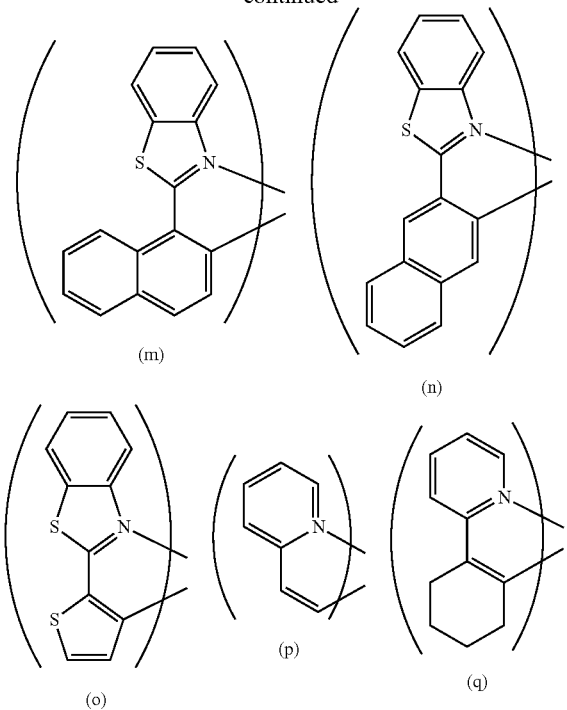

Further, in the general formula (1), a portion indicated by R1-X1-C(R3)-X2-R2 presumably functions as an ancillary ligand related to stereocontrol of the novel compound according to the present invention. Further, it is presumed that lone-electron pairs included in X1 and X2 cause the portion to have a potential hole-transport capability. In a case where there are a plurality of ancillary ligands (the after-mentioned "n" is an integer of not less than 2), the plurality of ancillary ligands may be the same ancillary ligand or different ancillary ligands from each other.

Conventionally, an acetylacetonate ligand (acetylacetonate: referred to as acac) is widely used as the ancillary ligand. However, in the present invention, the ancillary ligand exemplified above is employed, thereby making it possible to produce, by an extremely simple synthetic method, a novel phosphorescent substance (the novel compound according to the present invention) in which an occurrence of self-quenching can be minimized and which has an enhanced charge transport capability. With the above arrangement, it is possible to provide a novel luminescent material that exhibits a practically sufficient light-emitting property, not only in a case where the luminescent material is used as a luminescent dopant but also in a case where the luminescent material is used solely.

In the general formula (1), X1 and X2 each independently represent a nitrogen atom (N); an oxygen atom (O); a sulfur atom (S); or a phosphorous atom (P). Among them, it is preferable that both X1 and X2 represent a nitrogen atom so as to form an amidinate structure or a guanidinate structure, or that at least either X1 or X2 represent a phosphorous atom so as to form a phosphidinato structure.

Further, in the general formula (1), R1 and R2 each independently represent a straight, branched, or cyclic alkyl group; an aryl group; an aralkyl group; or an ether group. Examples of the alkyl group encompass: straight or branched C1 to C10 alkyl groups such as a methyl group, an ethyl group, an n-propyl group, an isopropyl group, an n-butyl group, an s-butyl group, an isobutyl group, and a t-butyl group; and cycloalkyl groups such as a cyclopentyl group and a cyclohexyl group. Examples of the aryl group encompass a phenyl group and the like. Examples of the aralkyl group encompass a benzyl group and the like. Examples of the ether group encompass a diethylether group, an ethyl methyl ether group, a cyclopentyl methyl ether group, a cyclohexyl methyl ether group, a phenyl methyl ether group, and the like. These groups may have a substituent such as a C1 to C4 alkyl group, a halogen group, or a C1 to C4 halogenated alkyl group. Among these examples, an isobutyl group or isopropyl group which may be halogenated, a cyclohexyl group which may have a substituent, or an aryl group which may have a substituent is preferable. Further, in a case where X1 or X2 is a phosphorous atom, two pieces of R1 or R2 may be bound to the phosphorous atom. In this case, the two pieces of R1 or the two pieces of R2 may be the same or different from each other.

Further, in the general formula (1), R3 represents a straight, branched, or cyclic alkyl group; an alkenyl group; an alkynyl group; an aryl group; an aralkyl group; an aliphatic, aromatic or cyclic amino group; a phosphino group; a boryl group; an alkylthio group; an arylthio group; an alkoxy group; an aryloxy group; an ether group; or an imino group. Examples of the alkyl group encompass C1 to C10 straight or branched alkyl groups such as a methyl group, an ethyl group, an n-propyl group, an isopropyl group, an n-butyl group, an s-butyl group, an isobutyl group, and a t-butyl group; cycloalkyl groups such as a cyclopentyl group, a cyclohexyl group; and the like groups. The alkenyl group may be, for example, a phenylvinyl group or the like. The alkynyl group may be, for example, a phenylacetyl group or the like. Examples of the aryl group encompass a phenyl group, an indenyl group, a fluorenyl group, a naphthyl group, a thiophenyl group, a pyridyl group, and the like. The aralkyl group may be, for example, a benzyl group or the like. Examples of the aliphatic amino group encompass a diethylamino group, a diisopropyl amino group, a diisobutyl amino group, a diaryl amino group, a bis(trimethylsilyl)amino group, and the like. Examples of the aromatic amino group encompass a phenyl amino group, a diphenyl amino group, and the like. Examples of the cyclic amino group encompass a carbazolyl group, an indolyl group, and the like. The boryl group may be, for example, phenylboryl or the like. The arylthio group may be, for example, a phenylthio group or the like. Examples of the alkoxy group encompass a methoxy group, an isopropyloxy group, a t-butoxy group, and the like. The aryloxy group may be, for example, a phenyloxy group or the like. Examples of the ether group encompass a diethylether group, an ethyl methyl ether group, a cyclopentyl methyl ether group, a cyclohexyl methyl ether group, a phenyl methyl ether group, and the like. The imino group may be, for example, an isopropyl imino group or the like. Any of these groups may have a substituent, e.g., a C1 to C4 alkyl group, a halogen group, a C1 to C4 halogenated alkyl group, or the like. Among these examples, R3 is preferably an isobutyl group which may be halogenated, a cyclohexyl group which may have a substituent, or an aryl group which may have a substituent. Further, among them, the aryl group which may have a substituent is more preferable, and the phenyl group which may have a substituent is especially preferable as R3.

That is, a particularly preferable ancillary ligand as the above ancillary ligand is an ancillary ligand (1) which has an amidinate structure or guanidinate structure in which both X1 and X2 represent a nitrogen atom, or a phosphidinato structure in which at least either X1 or X2 represents a phosphorous atom, (2) in which R1 and R2 each independently represent any one of (a) an isobutyl group, an isopropyl group or a tert-butyl group which may be halogenated, (b) a cyclohexyl group which may have a substituent, (c) an aryl group which may have a substituent; and (d) an ether group, and (3) in which R3 represents a phenyl group, a diphenyl amino group, a diallyl amino group, a diethyl amino group, a diisobutyl amino group, a diisopropyl amino group, a ditriethylsilyl amino group, a carbazolyl group, a fluorenyl group, or an isopropyl amino group, and these groups may have a substituent.

Further, in the general formula (1), a central metal M is a metal arbitrarily selected from transition metal atoms, for example, iridium (Ir), platinum, palladium, rhodium, rhenium, ruthenium, osmium, thallium, lead, bismuth, indium, tin, antimony, tellurium, gold, silver, and the like. Among them, any one of iridium, osmium or platinum is preferable, and iridium is more preferable as the central metal M.

Moreover, in the general formula (1), m and n are each independently an integer of not less than 1, and a total of m and n is not more than the largest number of ligands that can coordinate with the central metal M, preferably the same as the largest number of ligands. It depends on what type of central metal M is used, but in order to obtain a better light-emitting property, n is preferably 1 and m is preferably equal to <"the largest number of ligands that can coordinate with the central metal M"−1>. For example, in a case where the central metal M is iridium, the total of m and n is not more than 3, and therefore, it is preferable that n be 1 and m be 2.

Further, the novel compound according to the present invention represented by the general formula (1) is preferably a compound represented by the following general formula (2):

[Chem. 6]

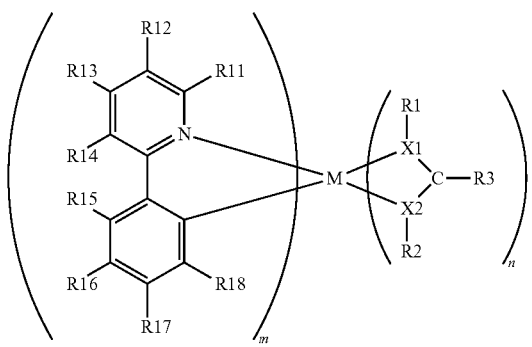

(2)

In the general formula (2), R11, R12, R13, R14, R15, R16, R17, and R18 (hereinafter collectively referred to as "R11 to R18") each independently represent a hydrogen atom; a halogen atom; or a C1 to C10 hydrocarbon group. The number of carbons included in the hydrocarbon group is preferably 1 to 5. Further, at least one hydrogen atom included in the hydrocarbon group may be substituted with a halogen atom such as fluorine, chlorine, bromine, iodine, or the like. Further, in a case where the hydrocarbon group includes at least two carbon atoms, the at least two carbon atoms may be partially substituted with at least either a sulfur atom or a nitrogen atom. Moreover, hydrocarbon groups (more preferably, adjacent hydrocarbon groups, i.e., at least one selected from pairs of R11 and R12, R12 and R13, R13 and R14, R14 and R15, R15 and R16, R16 and R17, and R17 and R18) may be bound to each other, so as to form an aromatic ring, a saturated or unsaturated hydrocarbon ring (except for an aromatic ring), or a heterocyclic ring having a sulfur atom and/or a nitrogen atom (heteroatom).

Further, in the general formula (2), the definitions of M, m, n, R1, R2, R3, X1, and X2 are the same as those explained in connection with the general formula (1).

The novel compound represented by the general formula (2) is more preferably a compound in which: 1) R11 to R18 each independently represent a hydrogen atom, a halogen atom, or a C1 to C5 hydrocarbon group; 2) M is iridium; 3) m is 2 and n is 1; 4) both X1 and X2 represent a nitrogen atom so as to form an amidinate structure or a guanidinate structure, or either X1 or X2 is a phosphorous atom so as to form a phosphidinato structure; 5) R1 and R2 each independently represent any one of (a) an isobutyl group, isopropyl group, or tert-butyl group which may be halogenated, (b) a cyclohexyl group which may have a substituent, (c) an aryl group which may have a substituent, and (d) an ether group; and 6) R3 represents a phenyl group a diphenyl amino group, a diallyl amino group, a diethyl amino group, a diisobutyl amino group, a diisopropyl amino group, a ditriethylsilyl amino group, a carbazolyl group, a fluorenyl group, or an isopropyl imino group, and these groups may have a substituent.

The novel compound represented by the general formula (2) is not limited to any particular compound. However, concrete examples of the novel compound represented by the general formula (2) encompass compounds represented by the following chemical formulae (5), for example. Note that a novel compound represented by (a) of the chemical formulae (5), i.e., bis(2-phenylpyridine)iridium(III)(N,N'-diisopropylbenzamidine) is hereinafter referred to as (ppy)$_2$Ir(dipba), and a novel compound represented by (b) of the chemical formulae (5), i.e., bis(7,8-benzoquinolinato)iridium(III)(N,N'-diisopropylbenzamidine) is hereinafter referred to as (bzq)$_2$Ir(dipba). The (ppy)$_2$Ir(dipba) and (bzq)$_2$Ir(dipba) use, as a cyclometalating ligand, phenylpyridine and benzoquinoline, respectively. Further, either of the novel compounds uses N,N'-diisopropylbenzamidine (a compound having an amidinate structure) as an ancillary ligand. The compounds represented by the chemical formulae (5) are as follows:

[Chem. 7]

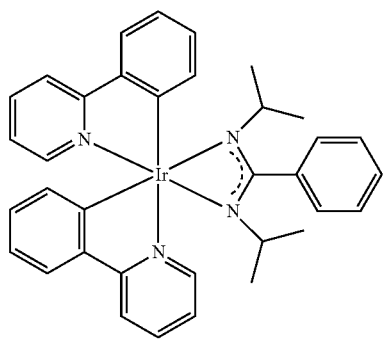

(5)

(a)

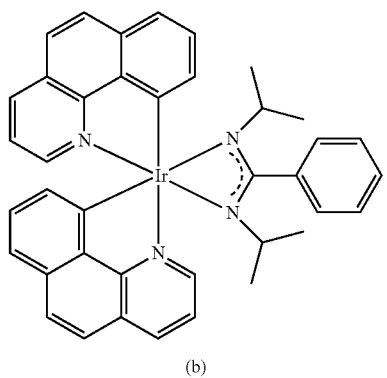

(b)

Except for these compounds, the following compounds represented by chemical formulae (8) to (21) can be exemplified as the compound according to the present invention as follows:

[Chem. 8]

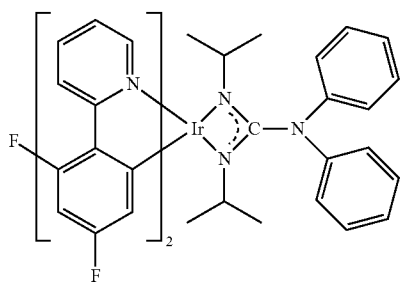

(8)

A novel compound represented by the chemical formula (8), i.e., bis(2-phenylpyridine)iridium(III)(N,N'-diisopropyl-N'',N'''-diphenylguanidine) is hereinafter referred to as Ir(ppy)$_2$didpg,

[Chem. 9]

(9)

A novel compound represented by the chemical formula (9), i.e., bis(2-(2,4-difluorophenyl)pyridine)iridium(III)N,N'-diisopropyl-N'',N'''-diphenylguanidine) is hereinafter referred to as Ir(dfppy)$_2$didpg.

[Chem. 10]

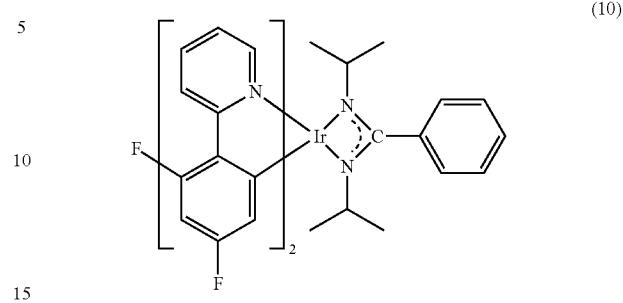

(10)

A novel compound represented by the chemical formula (10), i.e., bis(2-(2,4-difluorophenyl)pyridine)iridium(III)(N,N'-diisopropylbenzamidine) is hereinafter referred to as Ir(dfppy)$_2$dipba.

[Chem. 11]

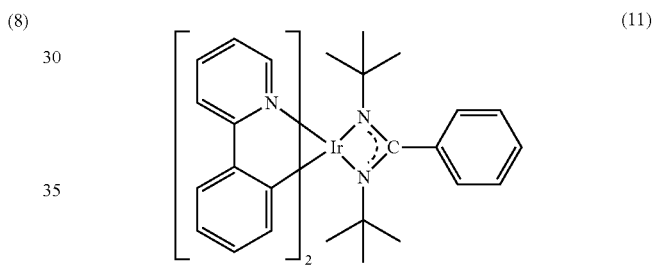

(11)

A novel compound represented by the chemical formula (11), i.e., bis(2-phenylpyridine)iridium(III)(N,N'-di-tert-butylbenzamidine) is hereinafter referred to as Ir(ppy)$_2$tbu-ba.

[Chem. 12]

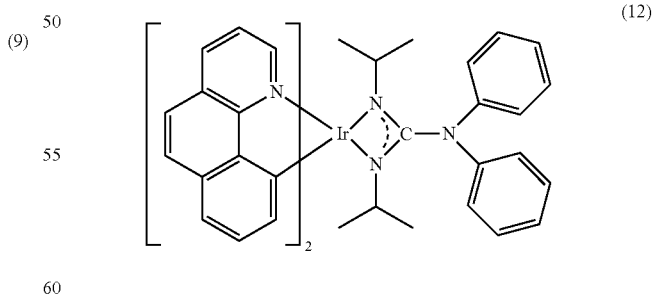

(12)

A novel compound represented by the chemical formula (12), i.e., bis(7,8-benzoquinolinato)iridium(III)(N,N'-diisopropyl-N'',N'''-diphenylguanidine) is hereinafter referred to as Ir(bzq)$_2$dip-dpg.

[Chem. 13]

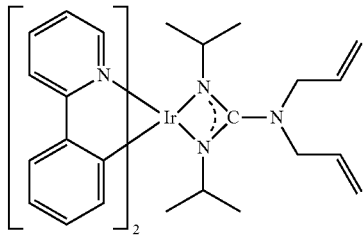

(13)

A novel compound represented by the chemical formula (13), i.e., bis(2-phenylpyridine)iridium(III)(N,N'-diisopropyl-N'',N''-diallylguanidine) is hereinafter referred to as Ir(ppy)$_2$(dipdg).

[Chem. 14]

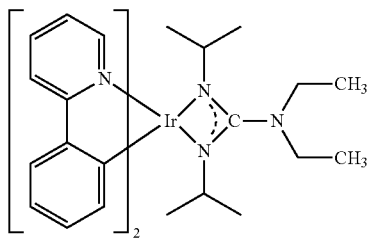

(14)

A novel compound represented by the chemical formula (14), i.e., bis(2-phenylpyridine)iridium(III)(N,N'-diisopropyl-N'',N''-diethylguanidine) is hereinafter referred to as Ir(ppy)$_2$(dipdeg).

[Chem. 15]

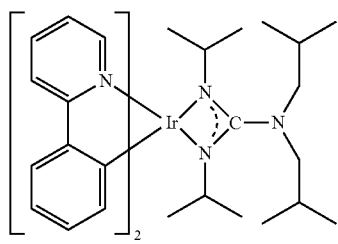

(15)

A novel compound represented by the chemical formula (15), i.e., bis(2-phenylpyridine)iridium(III) (N,N'-diisopropyl-N'',N''-diisobutylguanidine) is hereinafter referred to as Ir(ppy)$_2$(dipdbg).

[Chem. 16]

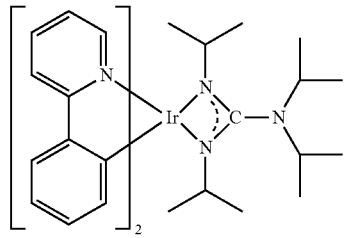

(16)

A novel compound represented by the chemical formula (16), i.e., bis(2-phenylpyridine)iridium(III)(N,N'-diisopropyl-N'',N''-diisopropylguanidine) is hereinafter referred to as Ir(ppy)$_2$dipgdip.

[Chem. 17]

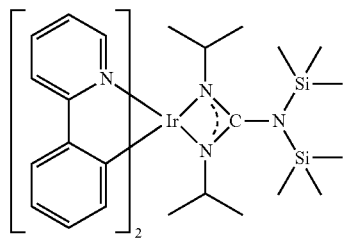

(17)

A novel compound represented by the chemical formula (17), bis(2-phenylpyridine)iridium(III) (N,N'-diisopropyl-N'',N''-bis(trimethylsilyl)guanidine) is hereinafter referred to as Ir(ppy)$_2$dip-dtmsg.

[Chem. 18]

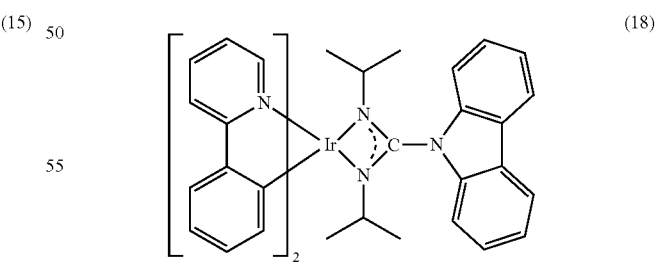

(18)

A novel compound represented by the chemical formula (18), i.e., bis(2-phenylpyridine)iridium(III)(N,N'-diisopropyl carbazolyl amidine) is hereinafter referred to as Ir(ppy)$_2$dip-cbzg,

[Chem. 19]

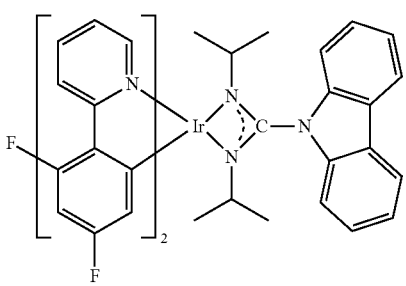

(19)

A novel compound represented by the chemical formula (19), i.e., bis(2-(2,4-difluorophenyl)pyridine)iridium(III)(N,N'-diisopropyl carbazolyl amidine) is hereinafter referred to as Ir(ppy)$_2$dip-cbzg.

[Chem. 20]

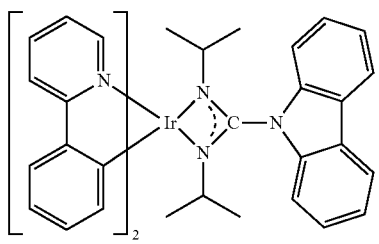

(20)

A novel compound represented by the chemical formula (20), i.e., bis(2-phenylpyridine)iridium(III)(N,N'-diisopropyl fluorenyl amidine) is hereinafter referred to as Ir(ppy)$_2$dip-fla.

[Chem. 21]

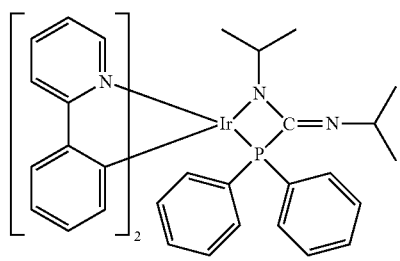

(21)

A novel compound represented by the chemical formula (21), i.e., bis(2-phenylpyridine)iridium(III)(N,N'-diisopropyl diphenyl phosphidine) is hereinafter referred to as Ir(ppy)$_2$dip-dpp.

Alternatively, the novel compound represented by the general formula (1) is preferably a compound represented by the following general formula (3):

[Chem. 22]

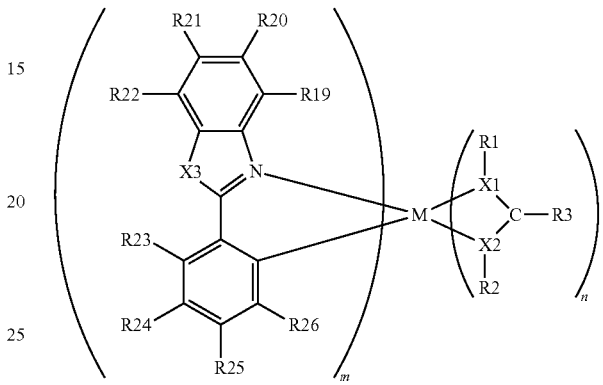

(3)

In the general formula (3), R19, R20, R21, R22, R23, R24, R25, and R26 (hereinafter collectively referred to as R19 to R26) each independently represent a hydrogen atom; a halogen atom; or a C1 to C10 hydrocarbon group. The number of carbons included in the hydrocarbon group is preferably 1 to 5. Further, at least one hydrogen atom included in the hydrocarbon group may be substituted with a halogen atom such as fluorine, chlorine, bromine, iodine or the like. Further, in a case where the hydrocarbon group includes at least two carbon atoms, the at least two carbon atoms may be partially substituted with at least either a sulfur atom or a nitrogen atom. Moreover, hydrocarbon groups (more preferably, adjacent hydrocarbon groups, i.e., at least one selected from pairs of R19 and R20, R20 and R21, R21 and R22, R23 and R24, R24 and R25, and R25 and R26) may be bound to each other, so as to form an aromatic ring, a saturated or unsaturated hydrocarbon ring (except for an aromatic ring), or a heterocyclic ring having a sulfur atom and/or a nitrogen atom (heteroatom).

In the general formula (3), X3 represents a sulfur atom or an oxygen atom.

Further, in the general formula (2), the definitions of M, m, n, R1, R2, R3, X1, and X2 are the same as those explained in connection with the general formula (1).

The novel compound represented by the general formula (3) is more preferably a compound in which: 1) R19 to R26 each independently represent a hydrogen atom, a halogen atom, or a C1 to C5 hydrocarbon group; 2) M is iridium; 3) m is 2 and n is 1; 4) both X1 and X2 represent a nitrogen atom so as to form an amidinate structure; 5) R1 and R2 each independently represent (a) an isobutyl group or isopropyl group which may be halogenated, (b) a cyclohexyl group which may have a substituent, (c) an aryl group which may have a substituent, or (d) an ether group; 6) R3 represents a phenyl group which may have a substituent; and 7) X3 represents a sulfur atom.

The novel compound represented by the general formula (3) is not especially limited to any particular compound. A concrete example of the novel compound represented by the general formula (3) is a compound represented by the following chemical formula (6). The novel compound represented by the chemical formula (6), i.e., bis(phenylbenzothiozolato)iridium(III)(N,N'-diisopropylbenzamidine) is hereinafter referred to as (bt)$_2$Ir(dipba). The (bt)$_2$Ir(dipba) uses phenylbenzothiazole as a cyclometalating ligand, and N,N'-diisopropylbenzamidine as an ancillary ligand. The compound represented by the chemical formula (6) is as follows:

[Chem. 23]

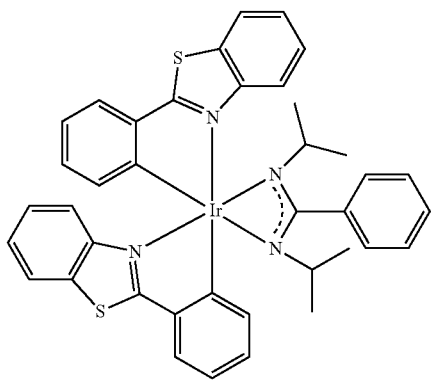

(6)

[Production Method]

The compound according to the present invention is produced by a method including the steps of: (1) preparing a primary metal complex by causing a cyclometalating ligand to coordinate with a central metal M; and (2) causing an ancillary ligand to coordinate with the primary metal complex. This method performs such a simple reaction as a two-step coordination formation, and uses an ancillary ligand having a simple chemical structure. This method accordingly has an advantage that a compound having an excellent light-emitting property can be synthesized more easily than a conventional technique.

The step (1) of preparing a primary metal complex may be performed, for example, in such a manner that a halide (metal chloride or the like) of the central metal M and a cyclometalating ligand are caused to coexist with each other for long enough under conditions to such a degree that they sufficiently coordinate with each other. For example, the step (1) can be performed by referring to a well-known method such as a method disclosed in M. Nonoyama, Bull. Chem. Soc. Jpn. 1974, 47, 767., or the like method.

In the step (1), an excessive amount of the cyclometalating ligand may be caused to coexist with 1 equivalent of the halide of the central metal M. More specifically, the cyclometalating ligand in at least an equivalent amount corresponding to m in the general formula (1) may be caused to coexist with 1 equivalent of the halide. For example, in a case where the central metal M is iridium, the cyclometalating ligand to be caused to coexist with the iridium may be not less than 2 equivalents, more preferably 2.5 to 3 equivalents with respect to 1 equivalent of a halide of the iridium.

The step (1) can be performed in a solvent that does not have reactivity with respect to the halide of the central metal M and the cyclometalating ligand. Such a solvent may be, for example, 2-methoxyethanol, tetrahydrofuran (THF), ethoxyethanol, or the like. Further, a mixture of such a solvent and water can be also used as the solvent as needed. Further, the solvent may be refluxed as needed.

A reaction temperature and a reaction pressure in the step (1) may be a room temperature and a normal pressure. In a case where the solvent is refluxed, the step (1) may be performed, for example, at a temperature and a pressure at which the solvent can vaporize.

The step (2) may be performed, for example, in such a manner that the primary metal complex prepared in the step (1) and an ancillary ligand are caused to coexist with each other for long enough under conditions to such a degree that they sufficiently coordinate with each other. The ancillary ligand indicates a ligand represented by R1-X1-C(R3)-X2-R2 in the general formula (1). The ancillary ligand is easily available, and may be one that is commercially available or one that is synthesized by a publicly-known synthetic method.

In the step (2), an excessive amount of the ancillary ligand may be caused to coexist with 1 equivalent of the halide of the central metal M. More specifically, the ancillary ligand in at least an equivalent amount corresponding to n in the general formula (1) may be caused to coexist with 1 equivalent of the halide of the central metal M. For example, in a case where the central metal M is iridium, at least 1 equivalent, more preferably 1.5 to 2 equivalents of the ancillary ligand may be caused to coexist with 1 equivalent of the iridium.

The step (2) can be performed in a solvent having no reactivity with respect to the halide of the central metal M and the ancillary ligand. Examples of such a solvent may be 2-methoxyethanol, tetrahydrofuran, ethoxyethanol, or the like. Further, a mixture of such a solvent and water can be also used as the solvent as needed. Further, the solvent may be refluxed as needed.

A reaction temperature and a reaction pressure in the step (2) may be a room temperature and a normal pressure. In a case where the solvent is refluxed, the step (2) may be performed, for example, at a temperature and a pressure at which the solvent can vaporize. Further, in order to prevent oxidation of a resultant product, it is preferable that the step (2) be performed in inactive gas atmosphere such as argon or the like.

In addition to the steps (1) and (2), a step of purifying a reactant product and the like step may be performed as appropriate.

An overview of a synthesis scheme in which the central metal M is iridium and the ancillary ligand is N,N'-diisopropylbenzamidine may be shown by the following general formula (7), as an example. The after-mentioned examples can be also referred to for understanding the synthesis scheme.

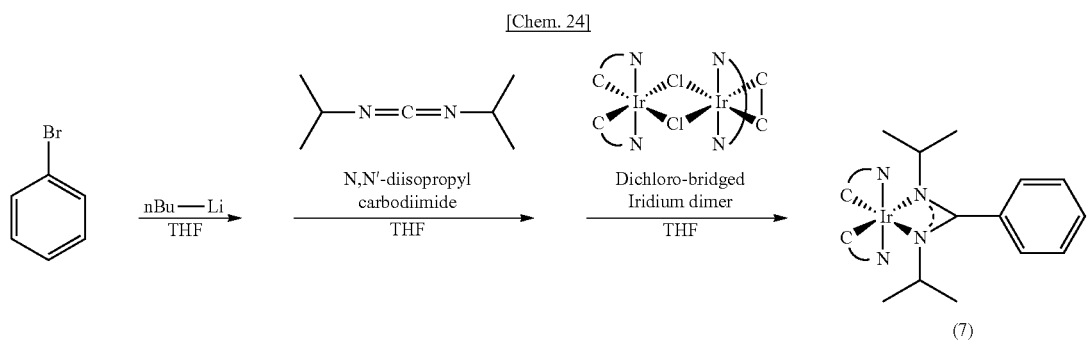

[Use of Novel Compound]

One example of the use of the novel compound according to the present invention is a luminescent material for organic light-emitting devices (OLEDs). Further, another example of the use of the novel compound according to the present invention is a detection marker by taking advantage of a property of generating light of the novel compound. The novel compound has the following advantageous characteristics as the luminescent material, for example: 1) the novel compound presumably has a potential hole-transport capability due to lone-electron pairs included in X1 and X2 in the ancillary ligand; and 2) stereocontrol due to the ancillary ligand presumably reduces a mutual action between light-emission moieties (cyclometalating ligands) in the novel compound or between the novel compounds.

Further, as explained in the after-mentioned examples, the novel compound according to the present invention exhibits the following characteristics: 1) the novel compound emits practically sufficient phosphorescence by voltage application at a room temperature; 2) an emission lifetime of the phosphorescence is quite short, so that self-quenching is minimized; 3) light is generated by application of a relatively low voltage (that is, luminous efficiency is good); and 4) luminous efficiency is hardly decreased even under relatively high current density so that the novel compound is excellent in durability and the like property. That is, the novel compound according to the present invention is especially suitable as the luminescent material that emits light by voltage application. More specifically, the novel compound according to the present invention is particularly suitable as a luminescent material for organic electroluminescence (EL) devices and the like, a detection marker for detecting an object based on whether or not light is generated by voltage application, and the like.

An organic EL display panel (one example of the organic EL devices) has such a feature that it can be suitably used to reproduce moving images due to its high-speed response and it can be more reduced in thickness, as compared with a liquid crystal display panel. On the other hand, the organic EL display panel has such a big problem that voltage application causes deterioration of a luminescent material, and further the organic EL display panel has a problem with luminous efficiency and the like. Particularly, when a display panel is produced with high resolution, each pixel is small in size. On this account, in order to ensure a practically sufficient luminance, it is necessary to apply a higher voltage to the luminescent material. In view of this, with the use of the novel compound according to the present invention as the luminescent material, it is possible, for example, to provide an organic EL display panel which has a long product age, which is excellent in luminous efficiency and has a low power consumption, and which has high resolution (for example, more than VGA).

Further, the present invention also provide a light-emitting device (organic EL device) including a pair of electrodes, and an emitting layer provided between the electrodes and containing a luminescent material, which emitting layer includes the compound according to the present invention. The following deals with the organic EL device, more specifically.

The electrodes provided in the organic EL device include at least an anode and a cathode. The anode is not especially limited. However, as the anode, a transparent electrode made from ITO (Indium-Tin Oxide) or the like is normally used so as to allow light emitted from the emitting layer to go outside.

The cathode is not especially limited, but may be an aluminum electrode, for example. Thicknesses of the anode and the cathode are not especially limited, but may be, for example, not less than 50 nm but not more than 400 nm, preferably not less than 100 nm but not more than 300 nm. Resistance values of the anode and the cathode may be, for example, not less than 5Ω but not more than 50Ω, preferably not less than 10Ω but not more than 30Ω.

The emitting layer includes the compound according to the present invention as the luminescent material. The emitting layer can be formed by a well-known method for forming a thin film, such as an evaporation method, a cast-film method, or the like. Among these methods, the evaporation method is preferable. A thickness of the emitting layer is not especially limited, but may be, for example, not less than 20 nm but not more than 40 nm, preferably not less than 30 nm but not more than 40 nm.

The emitting layer may include only the compound according to the present invention as the luminescent material. Alternatively, the emitting layer may further include other compounds as the luminescent material, in addition to the compound according to the present invention. For example, the compound according to the present invention may be used as a luminescent dopant, so that the compound may be doped in a luminescent host.

In a case where the compound according to the present invention is used as the luminescent dopant, a content ratio between the luminescent dopant and the luminescent host may be set as appropriate depending on an intended light-emitting property. A content ratio of the luminescent dopant in the luminescent material is not especially limited, but preferably not less than 10% by weight but not more than 80% by weight, more preferably not less than 20% by weight but not more than 40% by weight. As the luminescent host, 4,4'-N,N'-dicarbazole-biphenyl (CBP) or the like substance, which is publicly known, can be used as appropriate.

In such an arrangement that the compound (luminescent dopant) according to the present invention is doped in the luminescent host, the light-emitting property (emission wavelength or the like) can be changed depending on what type of luminescent host is used or how much amount of the compound is doped.

On the other hand, in a case where only the compound according to the present invention is used as the luminescent material, there are advantages as follows: 1) the emitting layer can be formed easily, and 2) phase separation between a luminescent dopant and a luminescent host does not occur (that is, quality deterioration is less likely to happen). Further, as shown in the following Examples, non-doped OLEDs exhibit characteristics comparable to those of doped OLEDs. Note that OLEDs in which a luminescent dopant is doped in a luminescent host are referred to as "doped OLEDs", while OLEDs that contains only one type of a luminescent material (that is, OLEDs that do not have a doping structure) are referred to as non-doped OLEDs.

In a case of such a non-doped structure, types of cyclometalating ligands to be contained in the compound according to the present invention may be changed so as to appropriately change the light-emitting property (emission wavelength, or the like). For example, $(ppy)_2Ir(dipba)$, $(bzq)_2Ir(dipba)$, and $(bt)_2Ir(dipba)$ exemplified in the following Examples respectively exhibit yellow electroluminescence (EL), orange electroluminescence (EL), and red electroluminescence (EL), which are the most excellent electroluminescence as the non-doped OLEDs.

In order to enhance recoupling between holes and electrons in the emitting layer, the organic EL device may further include a hole-injection layer, a hole-transport layer, a hole-blocking layer, an electron-transport layer, an electron-injection layer, and the like, which are made from well-known materials, as needed. In a case where the organic EL device includes all of these layers, they are provided in layers in the order of a substrate, an electrode (anode), the hole-injection layer, the hole-transport layer, the emitting layer, the hole-blocking layer, the electron-transport layer, the electron-injection layer, and an electrode (cathode).

The present invention is not limited to the description of the embodiments above, but may be altered by a skilled person within the scope of the claims. An embodiment based on a proper combination of technical means altered within the scope of the claims is encompassed in the technical scope of the present invention.

EXAMPLES

The following explains the present invention more specifically in accordance with Examples. However, the present invention is not limited to the following Examples.

Example 1

Synthesis of $(ppy)_2Ir(dipba)$ and $(bzq)_2Ir(dipba)$, and Analysis of Structures Thereof (Overall of Synthetic Reaction)

Unless otherwise stated, commercially available materials were used without purification. Hexane to be used as a solvent for washing or synthesis was obtained in such a manner that sodium and benzophenone were caused to coexist with each other in nitrogen atmosphere, and anhydrous hexane was distilled. Glass apparatuses, syringes, magnetic stirrers and the like to be used in synthetic reaction were dried in a convection oven for at least four hours.

Monitoring of the synthetic reaction was performed by use of a thin-layer chromatography (TLC). More specifically, with the use of a commercially-available TLC plate (Silica gel 60 F254, made by Merck), a spot was observed under ultraviolet light at wavelengths of 254 nm and 365 nm. Purification of an iridium complex obtained by the synthetic reaction was performed by use of silica column chromatography in which silica gel 60G (silica gel 60G, particle diameter of 5 to 40 μm, made by Merck) was filled.

(Synthesis of Cyclometalated Ir(III)μ-Chloro-Bridged Precursor)

A cyclometalated Ir(III)μ-chloro-bridged dimer (primary metal complex) represented by a general formula, $C^\wedge N_2Ir(\mu-Cl)_2IrC^\wedge N_2$, was synthesized by a method obtained by improving a method according to Nonoyama et al. (see M. Nonoyama, Bull. Chem. Soc. Jpn. 1974, 47, 767.).

More specifically, in a solvent containing 2-methoxyethanol and water by a ratio of 3:1, $IrCl_3.nH_2O$ (7 mmol, 2.5 g) and 2.5 equivalents of cyclometalating ligands (2.8 g of phenylpyridine, or 3.2 g of benzoquinoline) were caused to coexist with each other, and then refluxed for 6 to 7 hours or 24 hours. Subsequently, a reactant mixture was cooled down to a room temperature and water was added thereto, so that a reactant product was precipitated.

After that, the reactant mixture containing a precipitate (the reactant product) was filtered by use of a Buchner funnel. Subsequently, a residue obtained by the filtering was washed with hexane and ethyl ether several times, so as to obtain a crude product. A yield of a μ-chloro-bridged dimer including a phenylpyridine ligand was 85%, and a yield of a μ-chloro-bridged dimer including a benzoquinoline ligand was 82% or 80%.

(Synthesis of $(ppy)_2Ir(dipba)$ and $(bzq)_2Ir(dipba)$)

A hexane solvent (10 ml) was poured into a 50-ml flask, and 1-bromobenzene (65 mg, 0.4 mmol) and 2.6 mol/l of n-BuLi were caused to coexist with each other in the solvent. A mixture was stirred for about one hour, so as to lithiate 1-bromobenzene. Then, obtained phenyllithium was dropped into N,N'-diisopropyl carbodiimide (50 mg, 0.4 mmol). During the dropping, a solution was quickly stirred for 30 minutes or more, so as to prepare a transparent and colorless solution. The solution includes lithium N,N'-diisopropylbenzamidinato (ancillary ligand) as a reactant product.

Into another 50-ml flask, the μ-chloro-bridged dimmer obtained above, i.e., tetrakis(2-phenylpyridine-$C^2$,N')(μ-dichloro)-diiridium or tetrakis(7,8-benzoquinolinato-$C^2$,N')(μ-dichloro)-diiridium was added, and the obtained transparent and colorless solution was dropped thereinto. They were reacted with each other at 80° C. for 8 hours in argon atmosphere. A use amount of the μ-chloro-bridged dimer was 0.2 mmol in either case, which corresponds to 220 mg of the bridged dimer containing phenylpyridine, and 230 mg of the bridged dimer containing benzoquinoline.

Subsequently, a reactant was cooled down to a room temperature, and then, the solvent was vaporized under a reduced pressure. Thereafter, a residue was washed with heated diethylether three times. In this manner, novel iridium complexes, $(ppy)_2Ir(dipba)$ and $(bzq)_2Ir(dipba)$, according to the present invention were obtained. Respective yields thereof were 74% and 68%. The obtained novel iridium complexes were subjected to mass analysis and NMR analysis, so as to confirm that they were intended compounds. The following shows results of the analyses.

$(ppy)_2Ir(dipba)$:

MS: m/z 705 ($M^+$). Anal. Calcd for $C_{35}H_{36}IrN_4$: C, 59.64; H, 5.15; N, 7.95. Found: C, 59.76; H, 5.09; N, 7.88.

¹H NMR (300 MHz, CDCl₃, δ): 9.36 (d, J=5.70, 2H), 7.87 (d, J=8.1 Hz, 2H), 7.72 (t, J=7.2 Hz, 2H), 7.56 (d, J=8.1, 2H), 7.39 (t, J=7.2 Hz, 2H), 7.26-7.20 (m, 5H), 6.77 (t, J=7.2 Hz, 2H), 6.66 (t, J=7.2 Hz, 2H), 6.36 (d, J=7.8 Hz, 2H), 3.24-3.16 (m, 2H), 0.67 (d, J=6.3, 2H), −0.09 (d, J=6.3, 2H); ¹³C NMR (CDCl₃, δ): 24.39, 24.66, 47, 94, 117.83, 119.29, 121.13, 123.51, 127.90, 128.16, 128.86, 131.98, 135.24, 137.07, 144.11, 150.92, 156.05, 169.75, 174.63.
(bzq)₂Ir(dipba):
MS: m/z 753 (M⁺). Anal. Calcd for C₃₉H₃₆IrN₄: C, 62.21; H, 4.82; N, 7.44. Found: C, 62.12; H, 4.78; N, 7.55.
¹H NMR (300 MHz, CDCl₃, δ); 9.63 (d, J=5.10, 2H), 8.19 (d, J=8.1 Hz, 2H), 7.74 (d, J=9.0 Hz, 2H), 7.62 (t, J=7.2, 2H), 7.60 (d, J=9.0 Hz, 2H), 7.44-7.33 (m, 5H), 7.30 (d, J=8.1 Hz, 2H), 6.91 (t, J=7.2 Hz, 2H), 6.38 (d, J=7.2 Hz, 2H), 3.23-3.16 (m, 2H), 0.65 (d, J=6.0 Hz, 2H), −0.47 (d, J=6.0 Hz, 2H); ¹³C NMR (CDCl₃, δ): 24.04, 24.86, 48.05, 117.01, 120.50, 122.89, 126.01, 128.01, 128.19, 128.62, 129.07, 129.37, 133.76, 134.30, 136.92, 142.04, 149.74, 152.54, 159.66, 175.13.

(Single-Crystal X-Ray Diffraction Analysis)

Single crystals of the (ppy)₂Ir(dipba) and (bzq)₂Ir(dipba), which are suitable for X-ray structure analysis, were obtained so that their structures were examined by single-crystal X-ray diffraction analysis. X-ray diffraction data was obtained in ψ-rotation scan mode with the use of R-Axis Rapid diffractometer (Mo Kα radiation, graphite monochromator) (product name, produced by Rigaku. Corporation). Structure determination was made by a direct process using SHELXTL5.01v, and then refined by a full-matrix least-square method on F².

(a) of FIG. 1 schematically shows crystal packing of the (ppy)₂Ir(dipba). (b) of FIG. 1 schematically shows crystal packing of the (bzq)₂Ir(dipba). In either of these two types of indium complexes, stereocontrol occurs due to amidinate (ancillary ligand) so that intermolecular interaction occurs to such an extent that it can be ignored in a solid-phase state.

That is, as shown in (a) and (b) of FIG. 1, in the crystal of the (bzq)₂Ir(dipba), only slight overlap between respective benzoquinoline aromatic rings of adjacent molecules, is observed, and a distance between planes of the adjacent aromatic rings is about 3.3 Å. On the other hand, in the crystal of the (ppy)₂Ir(dipba), no overlap between respective phenylpyridine ligands of adjacent molecules, is observed. Further, in the (ppy)₂Ir(dipba), a vertical distance between planes of phenylpyridines of the adjacent molecules is 3.9 Å, which is relatively longer than that in the (bzq)₂Ir(dipba). In either of the iridium complexes, undesirable triplet-triplet annihilation tends to be avoided or reduced due to mutual interaction between the adjacent molecules, which can be more markedly observed especially in the (ppy)₂Ir(dipba) in a solid-phase state. This will be described later.

Example 2

Absorption, Photoluminescence (PL), and Electrochemical Measurement of (ppy)₂Ir(dipba) and (bzq)₂Ir(dipba)

(Methods of Absorption, PL, and Electrochemical Measurement)

(1) Electrochemical Measurement

The electrochemical measurement was conducted by use of BAS 100W Bioanalytical electrochemical work station (Bioanalytical Systems Inc, U.S). More specifically, the electrochemical measurement was conducted by cyclic voltammetry under such conditions that a platinum stick was employed as a working electrode, a platinum wire was employed as an auxiliary electrode, an Ag/Ag⁺ electrode having a core made of porous glass was employed as a reference electrode, a ferrocene/ferrocenium couple was used as a reference, and a scan rate was set to 100 mV/s. The measurement was performed in a CH₂Cl₂ solvent containing Bu₄NPF₆, which is an electrolyte, at a concentration of 0.1 mol/l.

(2) Absorption Spectrum and PL Spectrum

The absorption spectrum was obtained by use of UV-2550 UV-vis spectrometer (product name, made by Shimadzu Corporation). The PL spectrum was recorded by use of LS-55 Fluorescence Spectrometer (product name, made by Perkin-Elmer) that is provided with a xenon arc lamp as an excitation source. All solvents used were subjected to a freeze-pump-thaw cycle three times, so as to be degassed.

(3) Quantum Yield of Photoluminescence

A quantum yield of PL was measured based on quinine sulfate (Φ=0.546) in 1 mol/l of sulfuric acid.

(4) Emission Lifetime

An emission lifetime at a low temperature was measured in vacuum at a temperature of 77 K with the use of frozen glass emission samples. The frozen glass emission samples were prepared in such a manner that in a Dewar flask having a quartz window filled with liquid nitrogen, a quartz tube in which an iridium complex solution having a concentration of about 10⁻⁵ mol/l (a solvent was a mixture of degassed ethanol and methanol (volume ratio 4:1)) was contained was inserted.

Emission lifetimes under other conditions were measured in terms of a micro second unit by use of Quanta Ray DCR-3 pulsed Nd:YAG Laser System (pulse output 355 nm, 6 ns: product name, made by Newport).

(Results of Absorption, PL, and Electrochemical Measurement)

TABLE 1

|  | HOMO [eV] | LUMO [eV] | $E_g$ [eV] | $E^{ox}$ [V] |
|---|---|---|---|---|
| NPB | −5.4 | −2.4 | 3.0 | — |
| CBP | −6.1 | −3.0 | 3.1 | — |
| (ppy)₂Ir(dipba) | −4.8 | −2.5 | 2.3 | 0.2 |
| (bzq)₂Ir(dipba) | −4.8 | −2.6 | 2.2 | 0.3 |
| BCP | −6.7 | −3.2 | 3.5 | — |
| AlQ | −6.0 | −3.3 | 2.7 | — |

$E_g$ = Reduction Potential,
$E^{ox}$ = Oxidation Potential
HOMO = Highest Occupied Molecular Orbital Energy Level
LUMO (Lowest Unoccupied Molecular Orbital Energy Level) = HOMO + $E_g$ (1) Electrochemical Measurement Results of the electrochemical measurement are shown in Table 1. In Table 1, the reduction potential was estimated from an onset wavelength, which indicates optimal absorption. Further, just for reference, in regard to materials, NPB, CBP, BCP, and AlQ, which were used in Example 3 as described later, literature-based values thereof are also shown in Table 1.

There was such a limitation that in a CH₂Cl₂ solvent, the reduction potential could be only measured between −2.7 V and −3.5V. Therefore, only the oxidation potentials were obtained in regard to the iridium complexes according to the present invention.

The oxidation potential of the (ppy)₂Ir(dipba) was 0.23 V, and the oxidation potential of the (bzq)₂Ir(dipba) was 0.26 V. Either of the iridium complexes has a lower oxidation potential than those of conventional complexes ((ppy)₂Ir(acac) and (bzq)₂Ir(acac)) having acac as an ancillary ligand, or other Ir (C^N)₃ complexes (CAN is a cyclometalating ligand) having acac as an ancillary ligand. This indicates that either of the iridium complexes according to the present invention is relatively easy to oxidize (see the following documents: S. Jung et al., Eur. J. Inorg. Chem. 2004, 17, 3415.; A. B. Tamayo et al., J. Am. Chem. Soc. 2003, 125, 7377.; S. Lamansky et al., Inorg, Chem. 2001, 40, 1704). The amidinato ligand has a characteristic that its electron-donating capability is very high, which presumably results in that the oxidation potential is decreased largely.

In view of this, these novel iridium complexes according to the present invention have a very small energy gap, and the HOMO energy levels (hereinafter just referred to as "HOMO") of these complexes are higher than those of the $(ppy)_2Ir(acac)$, the $(bzq)_2Ir(acac)$, or the other Ir $(C^\wedge N)_3$ complexes having acac as an ancillary ligand. For example, the HOMO of the $(ppy)_2Ir(dipba)$ in vacuum is −4.78 eV, which is higher than that of the $(ppy)_2Ir(acac)$ (HOMO=−5.0 eV (literature-based value)) or $Ir(ppy)_3$ (HOMO=−5.2 eV (literature-based value)). That is, the novel iridium complexes according to the present invention exhibit a hole-transport capability more excellent than those of their analogues.

(2) Absorption Spectrum and PL Spectrum

Figure 2:
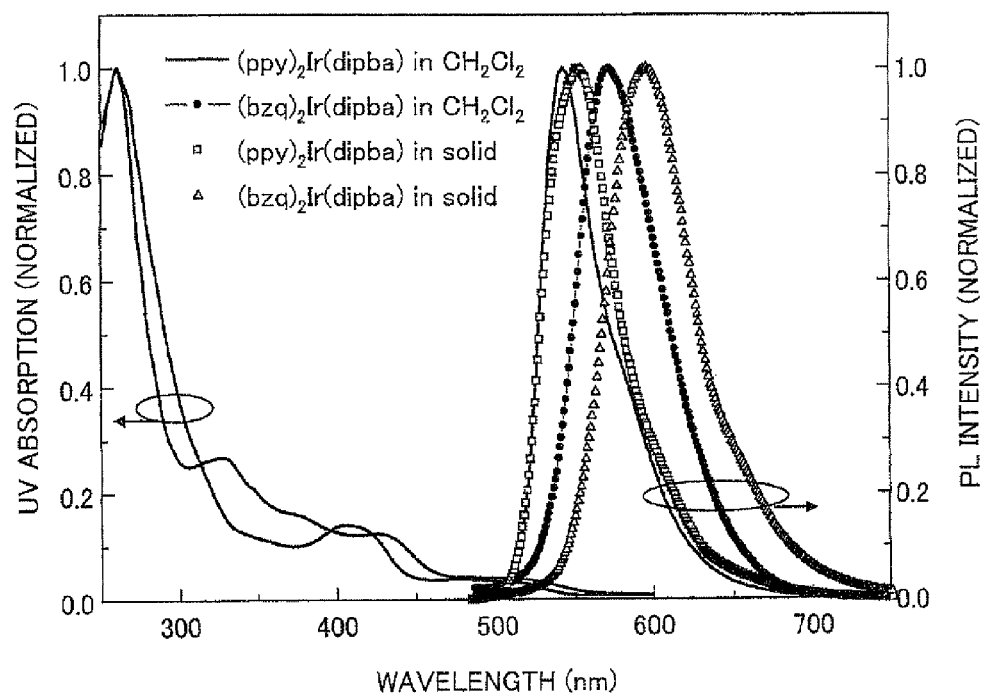
FIG. 2 shows graphs of UV-vis absorption spectra and PL spectra of the compounds according to the present invention observed in degassed dichloromethane and in a solid-phase state.

FIG. 2 shows UV-vis absorption spectra and PL spectra of the novel iridium complexes observed in degassed dichloromethane and in a solid-phase state. A strong absorption band under 360 nm is related to π-π* transition that is allowed to spin on the cyclometalating ligand. A broad absorption band at a low energy is unique to a metal-ligand charge transfer (MLCT). Either of the novel iridium complexes exhibits strong photoluminescence (PL) in a range from yellow or orange to red. Photoluminescence of the $(ppy)_2Ir(dipba)$ in dichloromethane and photoluminescence of the $(bzq)_2Ir(dipba)$ in dichloromethane exhibited maximum values at a wavelength of 543 nm and at a wavelength of 572 nm, respectively.

On the other hand, photoluminescence of these iridium complexes in a powdery state (one aspect of a solid-phase state) was shifted to red as compared with the spectra of the iridium complexes in a solution state (that is, in dichloromethane). More specifically, the photoluminescence of the powdery $(ppy)_2Ir(dipba)$ and the photoluminescence of the powdery $(bzq)_2Ir(dipba)$ exhibited maximum values at a wavelength of 553 nm and at a wavelength of 596 nm, respectively.

It is assumed that this phenomenon is related to intermolecular interaction between ligands as chromophores. A degree of the red-shift is larger in the $(bzq)_2Ir(dipba)$ than in the $(ppy)_2Ir(dipba)$. This is presumably because in the $(bzq)_2Ir(dipba)$, there is slight overlap between n electrons in a dimer unit.

(3) Quantum Yield of Photoluminescence

A quantum yield of phosphorescence represented by $\Phi_p$ in a $CH_2Cl_2$ solution of the $(ppy)_2Ir(dipba)$ was 0.30 and that of the $(bzq)_2Ir(dipba)$ was 0.41. These values are comparable to $\Phi_p$ (0.4) of $Ir(ppy)_3$, which is a conventional iridium complex.

However, the $Ir(ppy)_3$ in a powdery state hardly exhibits PL. In contrast, the novel iridium complexes in a powdery state exhibit bright yellow or orange PL even in air. That is, it is demonstrated that self-quenching of luminescence of the novel iridium complexes in a solid-phase state hardly occurs.

(4) Emission Lifetime

An emission lifetime of phosphorescence is one of important factors of triplet-triplet annihilation. It is known that the longer the emission lifetime of phosphorescence is, the more triplet-triplet annihilation a material potentially has. The emission lifetimes of phosphorescence of the $(ppy)_2Ir(dipba)$ and the $(bzq)_2Ir(dipba)$ in a solid-phase state are 0.14 μs and 0.12 μs, respectively, which are extremely short. That is, it was demonstrated that either of these novel iridium complexes exhibits very high phosphorescence, has a relatively short emission lifetime, and causes very slight self-quenching even in a solid-phase state.

In addition, the emission lifetimes of the $(ppy)_2Ir(dipba)$ and the $(bzq)_2Ir(dipba)$ at a low temperature (77 K) were respectively 0.28 μs and 0.60 μs. These values are shorter than respective emission lifetimes of the $(ppy)_2Ir(acac)$ and the $(bzq)_2Ir(acac)$ (3.2 and 23.3 μs, respectively) (see S. Lamansky et al: Inorg. Chem. 2001, 40, 1704). This result suggests that an amidinato spacer plays a very important role to decrease (i) mutual interaction between luminous moieties of molecules of the $(ppy)_2Ir(dipba)$ and (ii) mutual interaction between luminous moieties of molecules of the $(bzq)_2Ir(dipba)$.

Example 3

Production of OLEDs Using $(ppy)_2Ir(dipba)$ or $(bzq)_2Ir(dipba)$ and Measurement of Electroluminescence (EL)

(Production of Non-Doped OLEDs)

In order to understand the light-emitting property of these iridium complexes according to the present invention, non-doped OLEDs (diodes in this example) I and III were produced by use of these complexes in the following manner. Initially, a glass substrate (sheet resistor: 20 Ω/cm²) of which one surface was covered with ITO (formed into an anode) was subjected to ultrasonic cleaning with ethanol, acetone, and detergent. Then, on the ITO film were thermally evaporated organic materials, i.e., (a) N,N'-diphenyl-N,N'-bis(1-naphthyl)-1,1'-diphenyl-4,4'-diamine (NPB), (b) an iridium complex (the $(ppy)_2Ir(dipba)$ for the OLEDs I, and the $(bzq)_2Ir(dipba)$ for the OLEDs III), (c) 2,9-dimethyl-4,7-diphenyl-1,10-phenanthroline (BCP), and (d) tris(8-hydroxyquinoline) aluminum (AlQ) in this order under a pressure of about 3.5×10⁻⁴ Pa and a rate of 1.0 Å/s. Respective thicknesses of the NPB, the iridium complex, the BCP, and the AlQ are 30 nm, 35 nm, 10 nm, and 25 nm.

Subsequently, on the AlQ film, a lithium fluoride (LiF) layer having a thickness of 0.5 nm was vacuum-evaporated at a rate of 0.2 Å/s. Finally, the resultant was put into another vacuum chamber, and an aluminum electrode (to become a cathode) was vacuum-evaporated thereon at a rate of 10 Å/s. Thus, the diodes were produced.

Figure 3:
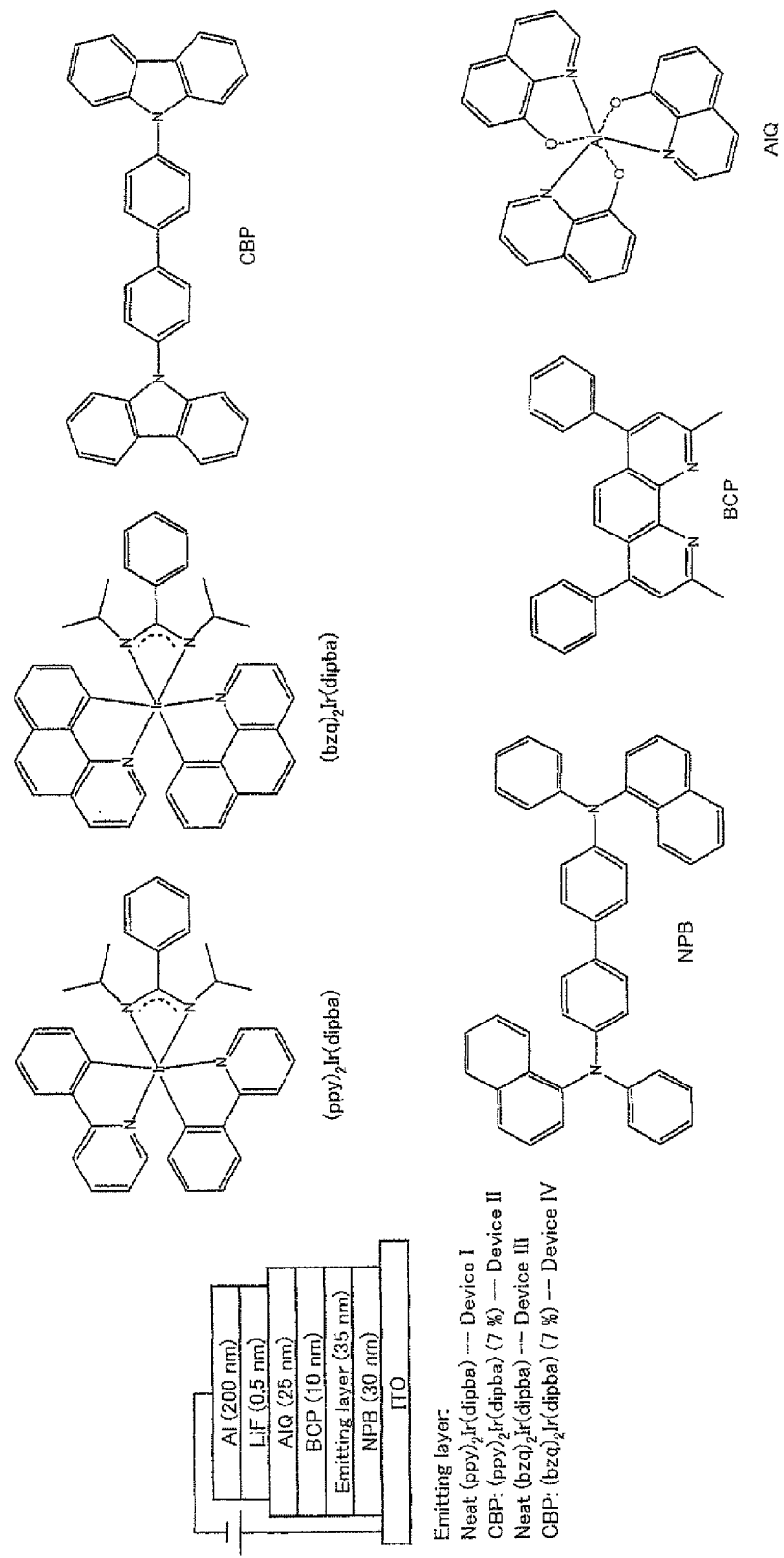
FIG. 3 is an explanatory diagram showing structures of organic light-emitting devices (OLEDs I to IV) according to the present invention and chemical structures of materials constituting the organic light-emitting devices.

An area of an active region of each diode was 2×3 mm². Note that the NPB layer functions as a hole-transport layer, the iridium complex layer functions as an emitting layer, the BCP layer functions as a hole-blocking layer, the AlQ layer functions as an electron-transport layer, and the LW layer functions as an electron-injection layer. Chemical structures of these materials and a structure of each of the OLEDs are shown in FIG. 3.

(Production of Doped OLEDs)

On the other hand, doped OLEDs II and IV were produced such that the iridium complexes according to the present invention were used as a luminescent dopant and doped on CBP, which is a luminescent host. Emitting layers of the doped OLEDs II and IV had a thickness of 35 nm, and contained, as a luminescent dopant, $(ppy)_2Ir(dipba)$ and $(bzq)_2Ir(dipba)$, respectively. In either case, a content ratio of the luminescent dopant to the luminescent host was 7% by weight to 93% by weight. Each of the emitting layers was formed by thermally evaporating a material under a pressure of about 3.5×10⁻⁴ Pa and at a rate of 1.0 Å/s. Further, how to arrange and form the other layers except for the emitting layer is the same as that of the non-doped OLEDs I and III.

(Measurement of Electroluminescence (EL) of OLEDs I to IV)

The OLEDs I to IV thus produced were examined to measure their EL spectra and luminance-current density-voltage characteristics at a room temperature by use of a combination of Spectrascan PR-650 Spectrophotometer (production name, made by PHOTO RESEARCH) and a computer-controlled direct-current power supply Keithley model 2400 voltage-current source.

(Results)

The OLEDs I to IV exhibited yellow or orange luminescence regardless of how much driving voltage (3 V to 16 V) was applied.

Figure 4:
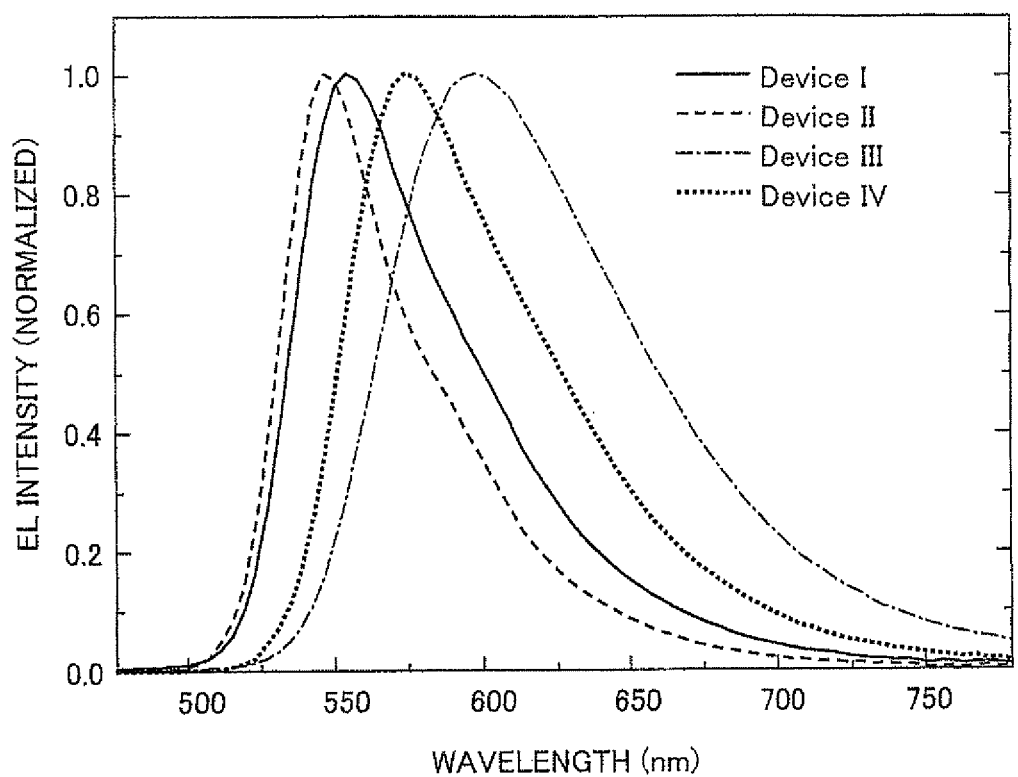
FIG. 4 shows graphs of EL spectra of the OLEDs I to IV to which a driving voltage of 6V is applied.

FIG. 4 shows EL spectra of the OLEDs I to IV to which a driving voltage of 6 V was applied. The OLEDs I and III, in which the emitting layers were made from only the respective iridium complexes, generated light of yellow and light of orange, respectively, and had respective emission peaks at 552 nm and 596 nm. The resultant spectra of the OLEDs I and III are approximate to the PL spectra of the respective iridium complexes in a solid-phase state (see FIG. 2). This indicates that no chemical change of the respective iridium complexes occurred during the production and driving of the OLEDs. Further, CIE chromaticity coordinates (x, y) of the OLEDs I and III to which a driving voltage of 6 V was applied were (0.44, 0.55) and (0.58, 0.42), respectively.

Maximums of the EL spectra of the doped OLEDs II and IV were exhibited at 544 nm and 572 nm, respectively. That is, the EL spectra of the doped OLEDs II and IV were shifted to blue as compared with those of the non-doped OLEDs I and III, respectively. This is presumably because introduction of a luminescent dopant into a luminescent host base material causes the luminescent dopant to be localized. In terms of spectrographic characteristics, CIE chromaticity coordinates of the OLEDs II were (0.40, 0.58) and CIE chromaticity coordinates of the OLEDs IV were (0.51, 0.47). In any of the OLEDs I to IV, no characteristic light emission was observed from the NPB, CSP, and AlQ. This suggests that light emission from the OLEDs I to IV is mainly derived from triplet excited state of the iridium complexes.

Figure 5:
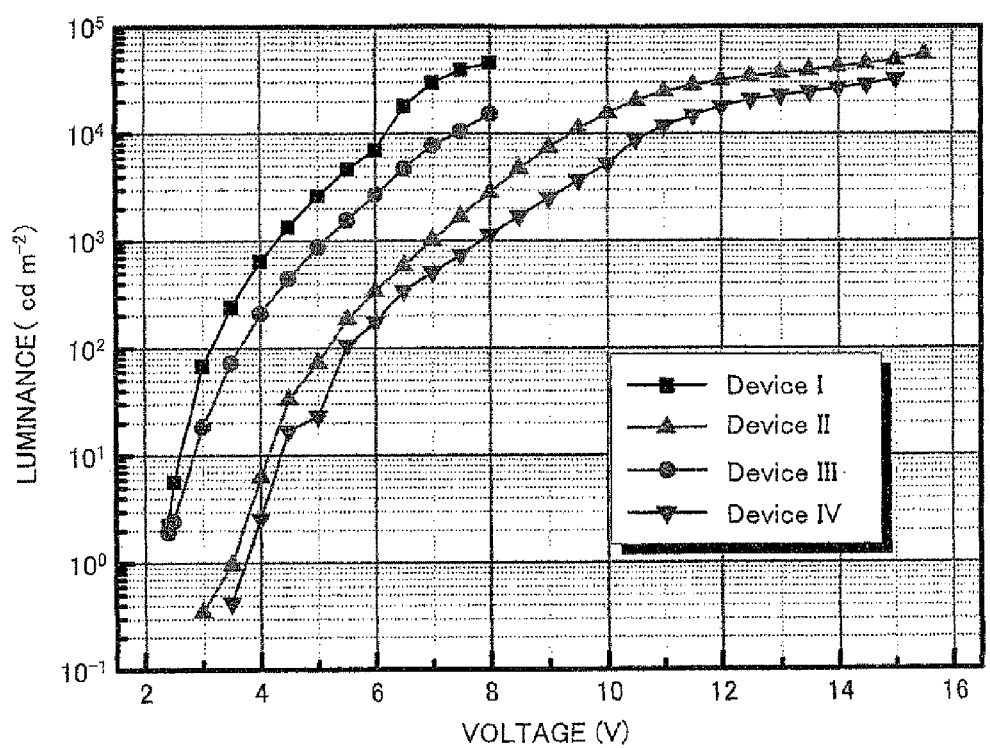
FIG. 5 shows graphs of measurement results of respective luminance-voltage characteristics of the OLEDs I to IV.

FIG. 5 shows measurement results of the luminance-voltage characteristics of the OLEDs I to IV. As compared with the doped OLEDs II and IV, the non-doped OLEDs I and III require a lower driving voltage. More specifically, in order to attain a luminance of 1 cd/m$^2$, the OLEDs I and III require just a turn-on voltage of 2.4 V or below to be applied thereto, and EL intensities of the OLEDs I and III rapidly increase after application of an onset voltage. That is, the OLEDs I and III can attain high luminescence at a low applied voltage. Thus, the OLEDs I and III are excellent in luminous efficiency.

The OLEDs I attain a luminance of 100 cd/m$^2$ at an applied voltage of 3.2 V, and the OLEDs III attain a luminance of 100 cd/m$^2$ at an applied voltage of 3.7 V. This satisfies a typical condition required for a display device with a low power driving.

The OLEDs I and III reach respective peak luminance at an applied voltage of 8.0 V. The respective peak luminances of the OLEDs I and III are 45770 cd/m$^2$ and 15240 cd/m$^2$. On the other hand, in order to attain luminances equivalent to the peak luminances of the OLEDs I and III, the OLEDs II and IV require higher applied-voltages (14.5 V and 11.5 V, respectively).

One of the reasons why the OLEDs I and III requires lower driving voltages is presumably because the (ppy)$_2$Ir(dipba) and the (bzq)$_2$Ir(dipba) have narrow $E_g$ (see Table 1). The HOMO levels of the (ppy)$_2$Ir(dipba) and the (bzq)$_2$Ir(dipba) are higher than that of the CBP, which suggests that the configuration (the OLEDs I and III) in which holes are directly injected from the NPB into the iridium complex is more preferable than the configuration (the OLEDs II and IV) in which holes are injected from the NPB into the CBP, from the viewpoint of energy. That is, direct hole transport between the iridium complex and the NPB that constitutes the hole-transport layer is important for efficient hole-electron transport in an emitter.

Figure 6:
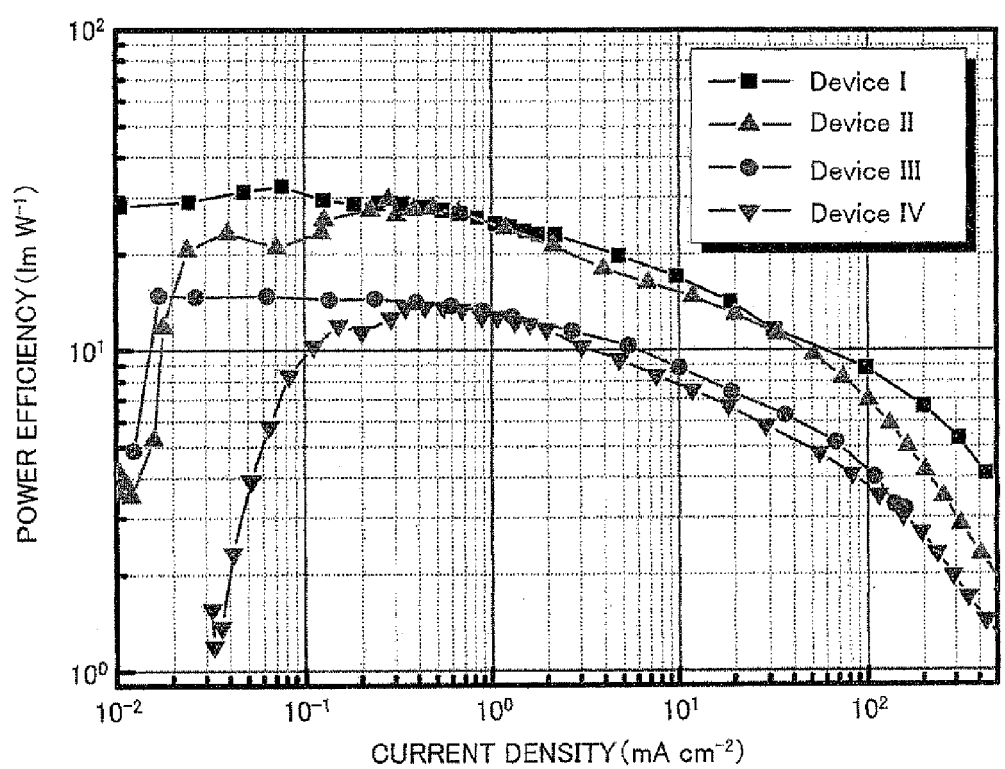
FIG. 6 shows graphs of respective current density-luminous efficiency relations of the OLEDs I to IV.

FIG. 6 shows current density-luminous efficiency relations of the OLEDs I to IV. All of the OLEDs exhibit excellent EL characteristics. Especially, the OLEDs I and III exhibit more excellent EL characteristics. Respective maximum power efficiencies of the OLEDs I and III are 32.5 lm/W and 14.8 lm/W. Further, the non-doped OLEDs I and III exhibit higher power efficiencies than corresponding doped OLEDs in a range of all current densities.

As far as the inventors know, the OLEDs I and III exhibit the best efficiencies as non-doped OLEDs (see the following documents: (1) Y. Wang et al.: Appl. Phys. Lett. 2001, 79, 449-451.; (2) R. J. Holmes et al.: Appl. Phys. Lett 2003, 83, 3818-3820.; (3) Y. H. Song et al.: Adv. Func. Mater. 2004, 14, 1221-1226.; and (4) Z. W. Liu et al.: Adv. Func. Mater. 2006, 16, 1441-1448).

Moreover, the power efficiency (max: 32.5 μm/W) of the OLEDs I is comparable to the best efficiency among Ir(ppy)$_3$ or (ppy)$_2$Ir(acac)-doped OLEDs that have been reported so far (see the following documents: (1) Baldo, M. A. et al.: Appl. Phys. Lett. 1999, 75, 4-6.: (2) Adachi et al.: J. Appl. Phys. 2001, 90, 5048-5051.; (3) Lamansky, S. et al.: J. Am. Chem. Soc. 2001, 123, 4304-4312.; and (4) Nazeeruddin, M. K. et al.: J. Am. Chem. Soc. 2003, 125, 8790-8797). Further, the power efficiency of the OLEDs I exhibits an excellent characteristic that the power efficiency is always maintained at a value over 10 μm/W, in a range of the current density from 10 mA/cm$^2$ to 100 mA/cm$^2$.

Further, in wide ranges of the current density (0.1 mA/cm$^2$ to 100 mA/cm$^2$) and of the luminance (20 cd/m$^2$ to 20000 cd/m$^2$ for the OLEDs 1 and 20 cd/m$^2$ to 10000 cd/m$^2$ for the OLEDs III), decreases in the luminous efficiencies of the OLEDs I and III relatively less occur. More specifically, the luminous efficiency of the OLEDs I exceeds 20 cd/A, and the luminous efficiency of the OLEDs III exceeds 10 cd/A. As such, in either case, the luminous efficiency is kept at a high level.

That a decrease in the luminous efficiency is moderate at a high current density and a high luminance suggests that the OLEDs I and III have very excellent durability. Some of the reasons thereof are as follows: (1) they have a stable charge-carrier balance and have an effect of efficient containment of triplet excitons occurring in the emitting layer, and (2) amidinato (ancillary ligand) introduced into the iridium complexes causes centers of emitters to be separated from each other so that efficiency of triplet-triplet annihilation is decreased.

Due to such an excellent EL performance, these two types of novel iridium complexes are usable, for example, as emitters for use in an active matrix display and an illumination system.

Further, the power efficiencies of the non-doped OLEDs I and III according to the present invention were maintained at a high level equivalent to those of the corresponding doped OLEDs II and IV at a current density of more than 1 mA/cm$^2$ (see FIG. 6).

One of the reasons why the OLEDs I and III have such excellent power efficiencies is that their driving voltages are quite low. Further another reason is such that when the novel iridium complexes according to the present invention are singularly used as an emitter, they exhibit an excellent hole-transport capability and a retrained self-quenching characteristic. Moreover, either of the iridium complexes has a very short life duration of a triplet state, which is an advantage for high-efficient production of the OLEDs.

Example 4

Synthesis of (bt)$_2$Ir(dipba), and Analysis of Structure Thereof

The explanation in Example 1 can be generally applied to synthetic reaction in this example.
(Synthesis of Cyclometalated Ir(III)μ-Chloro-Bridged Precursor)

In accordance with a method obtained by improving the aforementioned method of Nonoyama et al., [(bt)$_2$Ir(μ-Cl)]$_2$, which is a cyclometalated Ir(III)μ-chloro-bridged dimer (primary metal complex) was synthesized.

More specifically, in a solvent containing 2-methoxyethanol and water by a ratio of 3:1, IrCl$_3$.nH$_2$O (7 mmol, 2.5 g) and 2.5 equivalents of cyclometalating ligands (3.8 g of phenyl-2-benzothiozolato) were caused to coexist with each other, and then refluxed for 6 to 7 hours. Subsequently, an obtained reactant mixture was cooled down to a room temperature, and water was added thereto so that a reactant product was precipitated.

After that, the reactant mixture containing a precipitate (the reactant product) was filtered by use of a Buchner funnel. Subsequently, a residue obtained by the filtering was washed with hexane and ethyl ether several times, so as to obtain a crude product. A yield of [(bt)$_2$Ir(μ-Cl)]$_2$ was 95%.

(Synthesis of (bt)$_2$Ir(dipba))

A hexane solvent (10 ml) was poured into a 50-ml flask, and 1-bromobenzene (65 mg, 0.4 mmol) and 2.6 mol/l of n-BuLi (0.15 ml) were caused to coexist with each other in the solvent in argon atmosphere. A mixture was stirred for about one hour, so as to lithiate 1-bromobenzene. Then, obtained phenyllithium was dropped into N,N'-diisopropyl carbodiimide (50 mg, 0.4 mmol). During the dropping, a solution was quickly stirred for 30 minutes or more, so as to prepare a transparent and colorless solution. The solution includes lithium N,N'-diisopropylbenzamidinato (ancillary ligands) as a reactant product.

Into another 50-ml flask, a hexane solvent (15 ml) containing the μ-chloro-bridged dimer, i.e., [(bt)$_2$Ir(μ-Cl)]$_2$ (0.2 mmol, 235 mg) was added, and the obtained transparent and colorless solution was dropped thereinto. They were reacted with each other at 80° C. for 8 hours.

Subsequently, a reactant was cooled down to a room temperature, and then, the solvent was vaporized under a reduced pressure. Thereafter, a residual reactant was washed with diethylether (20 ml) three times. In this manner, a novel iridium complex (bt)$_2$Ir(dipba) according to the present invention were obtained. A yield thereof was 46%. The obtained novel iridium complex was subjected to mass analysis and NMR analysis, so as to confirm that it was an intended compound. The following shows results of the analyses.

MS: m/z 816 (M$^+$). Anal. Calcd for C$_{39}$H$_{35}$IrN$_4$S$_2$: C, 57.40; H, 4.32; N, 6.87. Found: C, 57.47; H, 4.35; N, 6.98. $^1$H NMR (300 MHz, CDCl$_3$) δ 9.20 (d, J=8.1 Hz, 2H), 7.94 (d, J=7.8 Hz, 2H), 7.62-7.67 (m, 4H), 7.52 (t, J=7.8 Hz, 2H), 7.29-7.36 (m, 3H), 7.18 (d, J=6.9 Hz, 2H), 6.78 (t, J=7.8 Hz, 2H), 6.60 (t, J=7.5 Hz, 2H), 6.47 (d, J=7.8 Hz, 2H), 3.36 (m, 2H), 0.58 (d, J=6.3 Hz, 6H), −0.17 (d, J=6.3 Hz, 6H).

(Single-Crystal X-Ray Diffraction Analysis)

A single crystal of the (bt)$_2$Ir(dipba), which is suitable for X-ray structure analysis, was obtained so that its structure was examined by single-crystal X-ray diffraction analysis. X-ray diffraction data was obtained in ψ-rotation scan mode with the use of R-AXIS RAPID diffractometer (Mo Kα radiation, graphite monochromator). Structure determination was made by a direct process using SHELXTL5.01v, and then refined by a full-matrix least-square method on F$^2$. A position of a hydrogen atom was refined by calculation in an isotropic manner.

Figure 7:
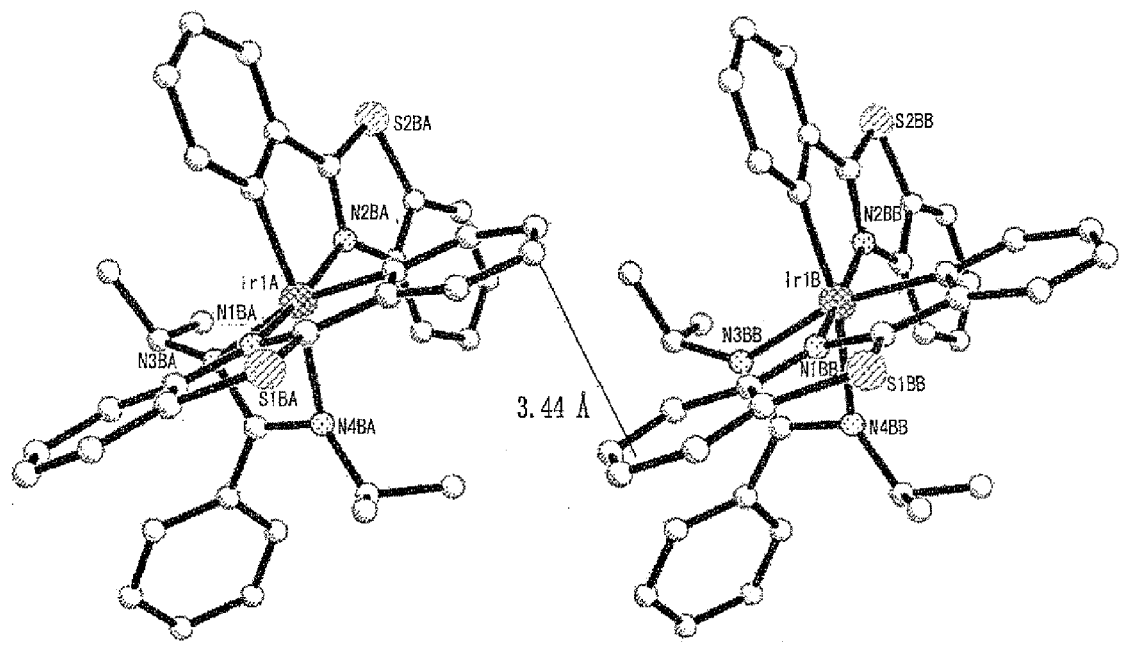
FIG. 7 is a schematic view illustrating crystal packing of another compound according to the present invention.

FIG. 7 schematically shows crystal packing of the (bt)$_2$Ir (dipba). As shown in FIG. 7, in a crystal of the (bt)$_2$Ir(dipba), only slight overlap was observed between π orbitals of adjacent molecules, and a distance between π orbitals of the adjacent molecules is about 3.44 Å. As such, in the (bt)$_2$Ir (dipba) in a solid-phase state, undesired self-quenching less occurs because no strong intermolecular interaction exists between amidinatos (ancillary ligands).

Example 5

Absorption, Photoluminescence (PL), and Electrochemical Measurement of (bt)$_2$Ir(dipba)

Electrochemical measurement, measurement of an absorption spectrum and a PL spectrum, and measurement of a quantum yield of photoluminescence were carried out in the same manner as in Example 2.

(Measurement of Absorption, PL, and Electrochemical Measurement)

TABLE 2

|  | HOMO [eV] | LUMO [eV] | $E_g$ [eV] | $E^{ox}$ [V] |
| --- | --- | --- | --- | --- |
| (bt)$_2$Ir(dipba) | −4.88 | −2.81 | 2.07 | 0.21 |
| (bt)$_2$Ir(acac) | −5.32 | −3.09 | 2.23 | 0.61 |

$E_g$, $E^{ox}$, HOMO, and LUMO are the same as in Table 1

(1) Electrochemical Measurement

Results of the electrochemical measurement are shown in Table 2. For comparison, data about (bt)$_2$Ir(acac) measured under the same conditions is also shown.

The novel iridium complex, (bt)$_2$Ir(dipba), exhibited a single oxidation wavelength in a CH$_2$Cl$_2$ solvent, and no reduction wavelength was detected.

Both of the complexes exhibited similar LUMO levels. However, as compared with the conventional complex, (bt)$_2$Ir(acac), having acac as an ancillary ligand, the novel complex, (bt)$_2$Ir(dipba), exhibits higher HOMO, and has a smaller HOMO-LUMO energy gap ($E_g$). That is, the HOMO of the (bt)$_2$Ir(dipba) in vacuum is −4.88 eV, which is higher than the HOMO (−5.32 eV) of the (bt)$_2$Ir(acac). Further, the energy gap of the (bt)$_2$Ir(dipba) in vacuum is 2.07 V, which is smaller than the energy gap (2.23 V) of the (bt)$_2$Ir(acac). In view of this, the novel iridium complex, (bt)$_2$Ir(dipba), emits light in a saturated red fluorescent region.

The oxidation potential of the (bt)$_2$Ir(dipba) was 0.21V. The oxidation potential of the (bt)$_2$Ir(acac) was 0.61V. That is, the (bt)$_2$Ir(dipba) has a lower oxidation potential than the (bt)$_2$Ir(acac), which indicates that the (bt)$_2$Ir(dipba) is relatively easy to oxidize. The amidinato ligand has a characteristic that its electron-donating capability is very high. This presumably contributes to a large decrease in oxidation potential.

(2) Absorption Spectrum and PL Spectrum

Figure 8:
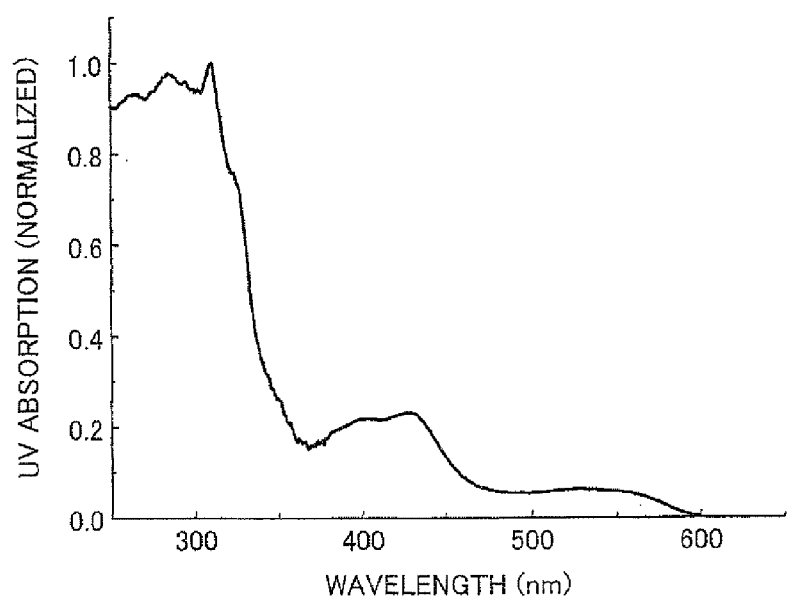
FIG. 8 shows a graph of a UV-vis absorption spectrum of the another compound of the present invention.

FIG. 8 shows a UV-vis absorption spectrum of the novel iridium complex, $(bt)_2Ir(dipba)$, observed in degassed dichloromethane. A strong absorption band under 360 nm is related to π-π* transition that is allowed to spin on the cyclometalating ligand. A broad absorption band at a low energy is unique to a metal-ligand charge transfer (MLCT).

Figure 9:
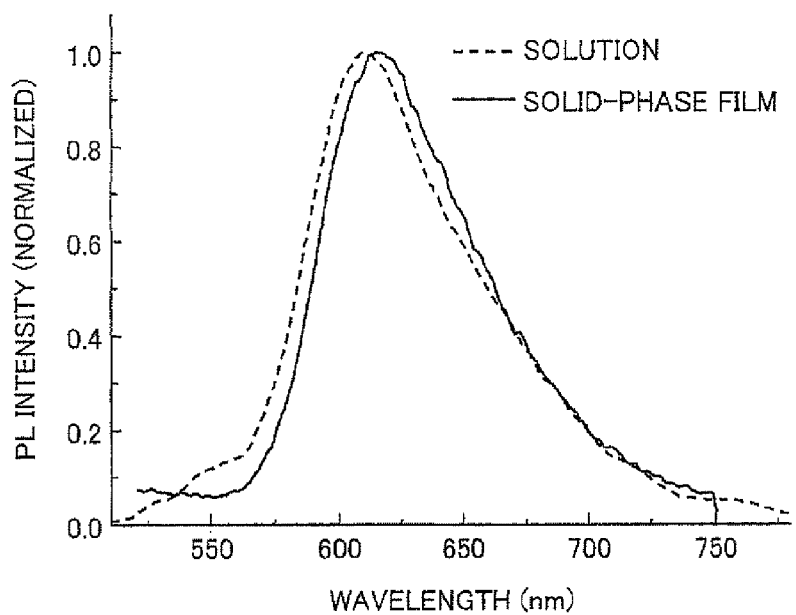
FIG. 9 shows graphs of PL spectra of the another compound according to the present invention.

FIG. 9 shows PL spectra of the $(bt)_2Ir(dipba)$ observed in degassed dichloromethane and in a solid film. The $(bt)_2Ir(dipba)$ exhibits strong red photoluminescence (PL) regardless of whether it is in the dichloromethane or in the solid film. The $(bt)_2Ir(dipba)$ exhibits a maximum value of photoluminescence in a range from 609 nm to 616 nm.

(3) Quantum Yield of Photoluminescence

A quantum yield of phosphorescence represented by $\Phi_p$ in a $CH_2Cl_2$ solution was about 0.10.

The $(bt)_2Ir(dipba)$ in a clean thin-film state exhibits bright red (616 nm) PL even in air. This indicates that this novel iridium complex in a solid-phase state hardly causes self-quenching of photoluminescence.

Example 6

Production of OLEDs Using $(bt)_2Ir(dipba)$ and Measurement of Electroluminescence (EL)

(Production of Non-Doped OLEDs)

In order to understand the light-emitting property of the iridium complex according to the present invention, non-doped OLEDs (diodes in this example) VIII using $(bt)_2Ir$(dipba) were produced. The production method of the OLEDs VIII are the same as the production method of the non-doped OLEDs described in Example 3 except that $(bt)_2Ir(dipba)$ was used as the iridium complex. Note that all organics were purified by gradient sublimation.

An area of an active region of each diode was 2×3 mm². Note that an NPB layer functions as a hole-transport layer, an iridium complex layer functions as an emitting layer, a BCP layer functions as a hole-blocking layer, an AlQ layer functions as an electron-transport layer, and a LiF layer functions as an electron-injection layer.

(Production of Doped OLEDs)

On the other hand, doped OLEDs V, VI, and VII were produced such that the iridium complex, $(bt)_2Ir(dipba)$, according to the present invention was used as a luminescent dopant and doped on CBP, which is a luminescent host. The structure of the doped OLEDs V, VI, and VII is the same as that of the non-doped OLEDs VIII except that emitting layers used in the dope OLEDs V, VI, and VII are CBP on which $(bt)_2Ir(dipba)$ (7 mol % for the OLEDs V, 15 mol % for the OLEDs VI, and 30 mol % for the OLEDs VII) is doped.

(Measurement of Electroluminescence (EL) of OLEDs V to VIII)

The OLEDs V to VIII thus produced were examined to measure their EL spectra, luminance-current density-voltage characteristics in the same manner as in Example 3.

(Results)

The OLEDs V to VIII exhibited bright red luminescence regardless of how much driving voltage was applied.

Figure 10:
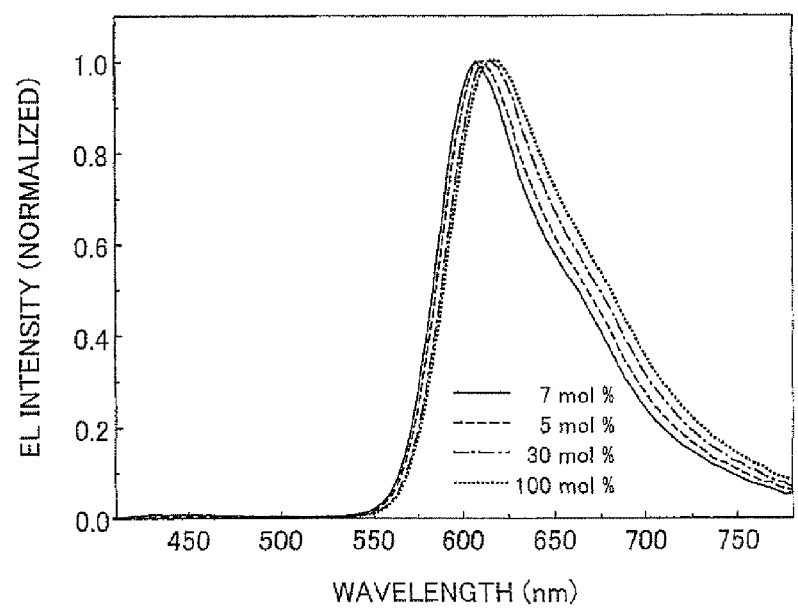
FIG. 10 shows graphs of EL spectra of organic light-emitting devices (OLEDs V to VIII) at a luminance of 10000 cd/m$^2$.

FIG. 10 shows EL spectra of the OLEDs V to VIII at a luminance of 10000 cd/m². Emission peaks and CIE chromaticity coordinates thereof at this time are shown in Table 3. The doped OLEDs V and IV having a low dopant concentration (respectively, 7 mol % and 15 mol %) generated orangey red light, and had respective emission peaks at 608 nm and 610 nm. On the other hand, the doped OLEDs VII having a high dopant concentration (30 mol %) generated pure red light. The non-doped OLEDs VIII generated almost similar pure red light. Emission peaks of the doped OLEDs VII and the non-doped OLEDs VIII were observed at 615 nm and 617 nm, respectively. Further, CIE chromaticity coordinates (x, y) of the OLEDs VII and VIII were, respectively, (0.64, 0.36) and (0.65, 0.35). These values are very approximate to the standard red (0.67, 0.33), which the National Television System Committee requires.

TABLE 3

| Light Emitting Diode | | V | VI | VII | VIII |
|---|---|---|---|---|---|
| Turn-On Voltage (V) | V (V) [a] | 3.3 | 2.7 | 2.5 | 2.5 |
| Max- | L (cd/m²) | 41060 | 32080 | 30160 | 15701 |
| | [b] | (11) | (10.5) | (9) | (8.5) |
| | LE (cd/A) | 23.1 | 21.4 | 18.1 | 8.4 |
| | [c] | (28, 4) | (186, 4.8) | (227, 3.8) | (171, 4.5) |
| | PE (lm/W) | 18.2 | 18.4 | 18.4 | 6.9 |
| | [c] | (28, 4) | (3, 2.8) | (21, 2.8) | (2, 2.6) |
| | QE (%) | 12 | 12.8 | 15.4 | 7.5 |
| | [c] | (28, 4) | (186, 4.8) | (227, 3.8) | (171, 4.5) |
| L = 100 cd/m² | V (V) | 4.9 | 4.4 | 3.3 | 4.2 |
| | LE (cd/A) | 21.5 | 20.8 | 17.8 | 8.1 |
| | PE (lm/W) | 14.5 | 15.1 | 16.9 | 6 |
| | QE (%) | 11.5 | 12.2 | 15.1 | 7.3 |
| L = 10000 cd/m² | EL $\lambda_{max}$ (nm) | 608 | 610 | 615 | 617 |
| | CIE | 0.62, 0.38 | 0.63, 0.37 | 0.64, 0.36 | 0.65, 0.35 |

[a] Recorded based on 1 cd/m².
[b] A value in parentheses is a corresponding voltage (V).
[c] Values in parentheses are a corresponding EL luminance (cd/m²) and a corresponding voltage (V).

Figure 11:
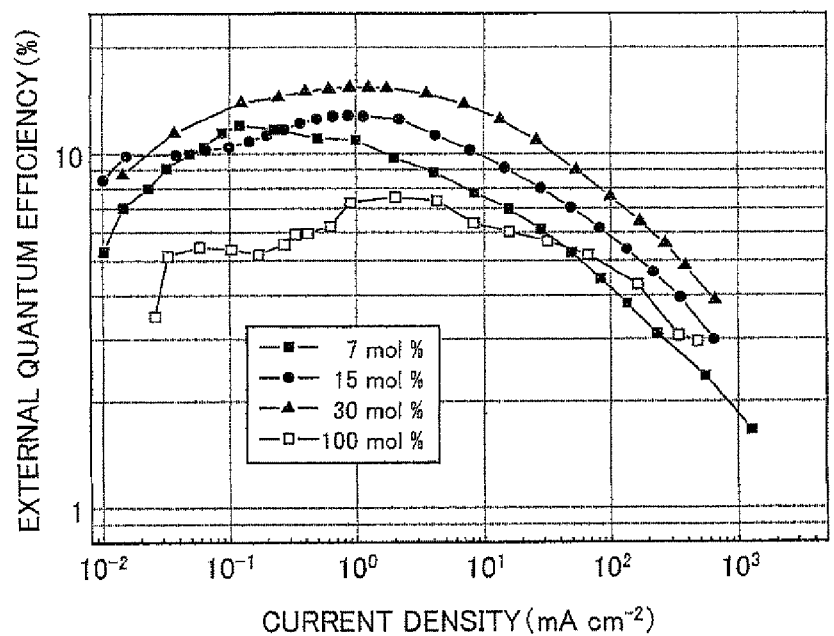
FIG. 11 shows graphs of respective current density-external quantum efficiency relations of the OLEDs V to VIII.
Figure 12:
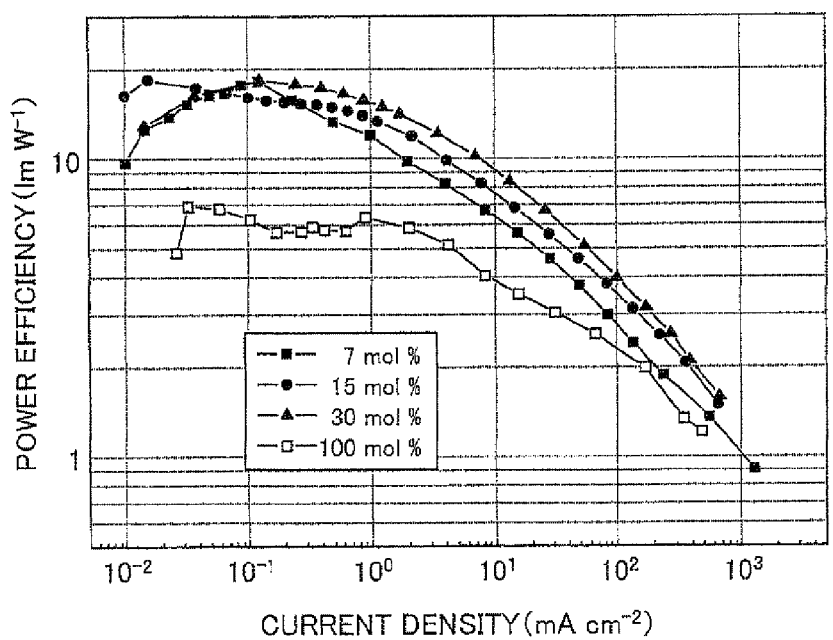
FIG. 12 shows graphs of respective current density-luminous efficiency relations of the OLEDs V to VIII.

FIG. 11 shows measurement results of external quantum efficiencies of the OLEDs V to VIII. FIG. 12 shows measurement results of power efficiencies of the OLEDs V to VIII.

The OLEDs V to VIII require a relatively low turn-on voltage of not more than 3.3 V to attain an emission luminance of 1 cd/m², and EL intensities of the OLEDs V to VIII rapidly rise after application of an On-voltage. That is, the OLEDs V to VIII can generate light with a high luminance at a low application voltage, and therefore they have excellent luminous efficiency.

Among them, the OLEDs VII having a doping concentration of 30 mol % is most excellent in terms of property. The OLEDs VII required a turn-on voltage of merely 2.5%, and a voltage application of 9V allowed the OLEDs VII to reach its maximum luminance of 30160 cd/m². Further, a voltage application of 3.8 V allowed the OLEDs VII to attain the largest external quantum efficiency of 15.4%. At this time, the OLEDs VII had a luminance of 227 cd/m$^2$. Further, the OLEDs VII attained a power efficiency of 18.4 μm/W at an application voltage of 2.8 V. This efficiency is the best efficiency among the saturated-type red OLEDs, as far as the inventors know (see the following documents: (1) J. P. Duan et al.: Adv. Mater. 2003, 15, 224.; and (2) C.-H. Chien et al.: Adv. Func. Mater. 2008, 18, 1430).

Further, it should be noted that these OLEDs are relatively less affected by the doping concentration of the emitting layer. For example, the OLEDs V (a doping concentration of 7 mol %) and VI (a doping concentration of 15 mol %) exhibited no decrease in EL performance at all, and maintained peak-efficiency values at equivalent high levels. More specifically, the OLEDs V and VI had respective power efficiencies of 18.2 lm/W and 18.4 lm/W and respective external quantum efficiencies of 12% and 12.8%.

As the concentration of the (bt)$_2$Ir(dipba) further increases (>30 mol %), the efficiency decreases. This is because a self-quenching effect in an emission center with a high doping concentration increases. Nonetheless, the non-doped OLEDs VIII exhibit a notable performance. That is, application of a driving voltage of 4.2 V allows the OLEDs VIII to successfully have a sufficient red luminance of 100 cd/m$^2$ and excellent efficiencies (a luminance efficiency of 8.1 cd/A, an external quantum efficiency of 7.3%, and a power efficiency of 6 lm/W). The peak efficiencies (the largest luminance efficiency of 8.4 cd/A, the largest external quantum efficiency of 7.5%, and the largest power efficiency of 6.1 lm/W) of the OLEDs VIII are best among the non-doped low-molecular phosphors that have been reported so far (see the following documents: (1) Y. H. Song et al.: Adv. Func. Mater, 2004, 14, 1221.; (2) Z. W. Liu et al.: Adv. Func. Mater. 2006, 16, 1441.; and (3) J. Q. Ding et al.: Wang, Adv. Func. Mater. 2008, 18, 2754). Such an notable enhancement of the EL performance of the non-doped OLEDs VIII suggests that the luminescent iridium complex, (bt)$_2$Ir(dipba), can efficiently transport charges without using any luminescent host.

Figure 13:
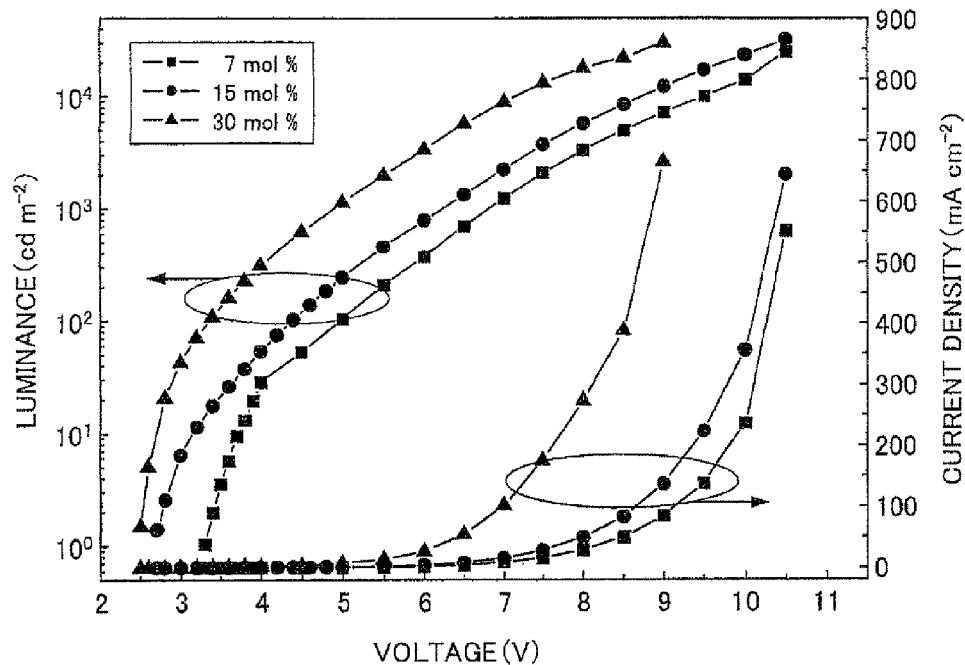
FIG. 13 shows respective relations of luminance-current density-voltage characteristics of the OLEDs V to VIII.

FIG. 13 shows graphs obtained by plotting respective current density-luminance-voltage characteristics of the OLEDs V to VII. As shown in FIG. 13, as a doping level increases, a driving voltage tends to be low. Further, it is assumed that the (bt)$_2$Ir(dipba) functions to transport charges.

As described above, with the use of the luminescent iridium complex, (bt)$_2$Ir(dipba), it is possible to produce high-efficiency pure red OLEDs that require a low driving voltage, either as doped OLEDs with a wide range of a doping concentration or as non-doped OLEDs.

(Production of Single-Carrier Device)

A significant improvement in EL performance of the (bt)$_2$Ir(dipba) is presumably attributable to a stable charge-carrier balance and an efficient recoupling in the emitting layer. In view of this, in order to further promote a better understanding of charge injection and carrier transport in the emitting layer, single-carrier devices were produced. Each of these devices had either a structure of Al/active molecular layer/Al or a structure of ITO/active molecular layer/Au. A metal (Al) having a small work function was used as an electrode in a device (electron-only) in which the carriers were only electrons. Further, a metal (Au) having a large work function or a metal oxide (ITO) having a large work function was used as an electrode in a device (hole-only) in which the carriers were only holes. For comparison, two types of devices, i.e., (a) a device using (bt)$_2$Ir(dipba) as an active molecular layer and (b) a device using (bt)$_2$Ir(acac) as an active molecular layer were also prepared for each of the electron-only device and the hole-only device.

(Measurement of Current Density and Luminance of Single-Carrier Device)

Figure 14:
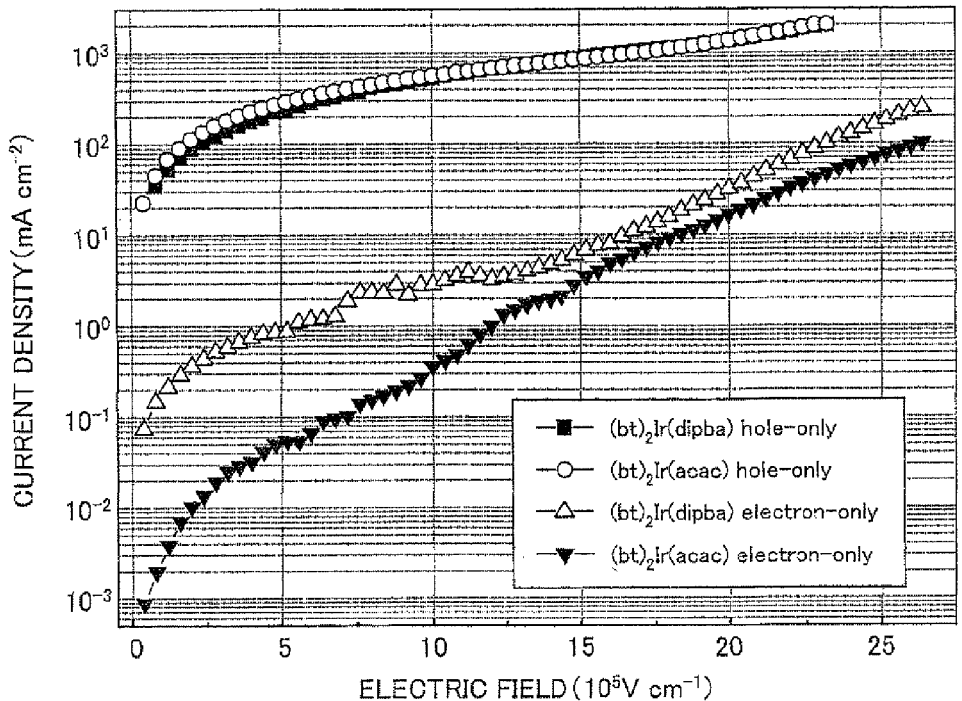
FIG. 14 shows graphs of respective current density-electric field relations of further other devices.

FIG. 14 shows graphs of measurement results of respective current density-electric field characteristics of the devices. In regard to the hole-only devices in which the carriers were only holes, there was not a big difference between the device using (bt)$_2$Ir(dipba) and the device using (bt)$_2$Ir(acac). However, in regard to the electron-only devices in which the carriers were only electrons, the current density of the device using (bt)$_2$Ir(dipba) was far larger than the current density of the device using (bt)$_2$Ir(acac). This is presumably because the (bt)$_2$Ir(dipba) has a stronger n bond capability due to the dipba ligand. This presumably allows electron hopping between adjacent molecules to be more easily caused.

Normally, the mobility of electrons in an organic EL material is a few orders of magnitude lower than the mobility of holes. Therefore, a further improvement in the performances of the OLEDs largely depends on efficient transfer of electrons in an EL device and efficient injection of electrons into the EL device such as the device using the (bt)$_2$Ir(dipba). The devices using the (bt)$_2$Ir(dipba) can reduce wide-range quantitative contrast between holes and electrons, thereby resulting in an excellent carrier balance in the emitting layer.

As described above, the oxidation potential (0.21 V) of the (bt)$_2$Ir(dipba) is far smaller than the oxidation potential (0.61 V) of the (bt)$_2$Ir(acac), and the HOMO of the (bt)$_2$Ir(dipba) is larger than the HOMO of the (bt)$_2$Ir(acac). In view of this, it is assumed that the iridium complex, (bt)$_2$Ir(dipba), having an amidinato ligand has an excellent ability of directly receiving holes. The significant increase in the EL performance of the devices using the (bt)$_2$Ir(dipba) partially depends on this excellent ability. This results in that more holes and electrons are efficiently recoupled in an emitting layer of OLEDs using the (bt)$_2$Ir(dipba) so as to cause triplet excitons.

Example 7

Synthesis of Ir(ppy)$_2$didpg and Measurement of Absorption and Photoluminescence of Ir(ppy)$_2$didpg The explanation in Example 1 can be generally applied to how synthesis reaction is performed in this example. This is applicable to Examples 8 to 20, which will be described later.

(Synthesis of Ir(ppy)$_2$didpg)

Into a 100-ml flask in argon atmosphere, 10 ml of THF containing diphenylamine (67 mg, 0.4 mmol), and a hexane solution of n-BuLi (2.77 M, 0.4 mmol, 0.14 ml) were added and stirred at a room temperature for about 2 hours. Then, N,N'-diisopropyl carbodiimide (50 mg, 0.4 mmol) was dropped into a resultant reactant solution. The reactant solution was quickly stirred for 2 hours, and then dropped into 15 ml of THF containing [(ppy)$_2$Ir(μ-Cl)]$_2$ (0.2 mmol, 220 mg) and stirred at 80° C. for 12 hours.

Subsequently, an obtained reactant was cooled down to a room temperature, and then, the solvent was vaporized under a reduced pressure. Thereafter, the reactant was added to 5 ml of toluene, and then the toluene was vaporized. A resultant product was washed with diethyl ether, thereby preparing a novel iridium complex, Ir(ppy)$_2$didpg, according to the present invention. A yield thereof was 80%. The novel iridium complex thus obtained was subjected to NMR analysis, so as to confirm that it was an intended compound. The following shows a result of the analysis.

$^1$H NMR (300 MHz, CDCl$_3$, rt) δ=9.20 (d, 2H, py-H), 7.86 (d, py-H, 2H), 7.75 (t, 4H, dph-o), 7.54 (d, 2H, Ph-H), 7.25 (m, 4H, dph-m), 7.00 (m, 4H, py-H and Ph-H), 6.76 (t, 2H, dph-p), 6.64 (t, 2H, Ph-H), 6.31 (d, 2H, Ph-H), 3.58 (b, 2H, C—H), 0.42 (d, 6H, —CH$_3$), 0.086 (d, 6H, —CH$_3$).

(Measurement of Absorption Spectrum and PL Spectrum)

The measurement of an absorption spectrum and a PL spectrum of the obtained novel iridium complex was carried out in the same manner as in Example 2.

Figure 15:
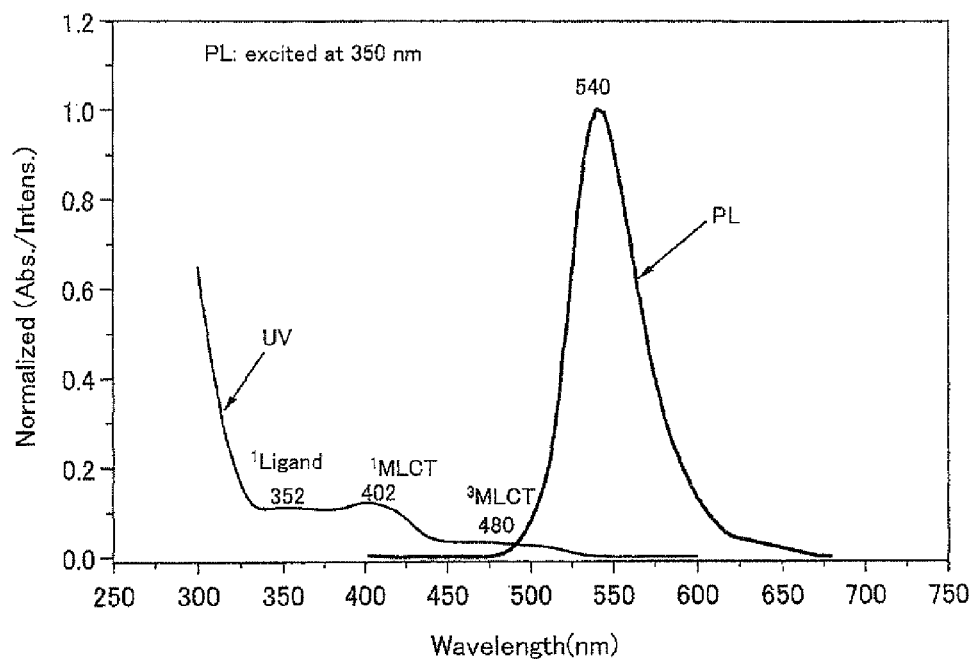
FIG. 15 shows graphs of a UV-vis absorption spectrum and a PL spectrum of another compound according to the present invention observed in degassed dichloromethane.

FIG. 15 shows a UV-vis absorption spectrum and a PL spectrum of the Ir(ppy)$_2$didpg observed in degassed dichloromethane. Photoluminescence of the Ir(ppy)$_2$didpg in dichloromethane exhibited a maximum value at a wavelength of 540 nm.

Figure 16:
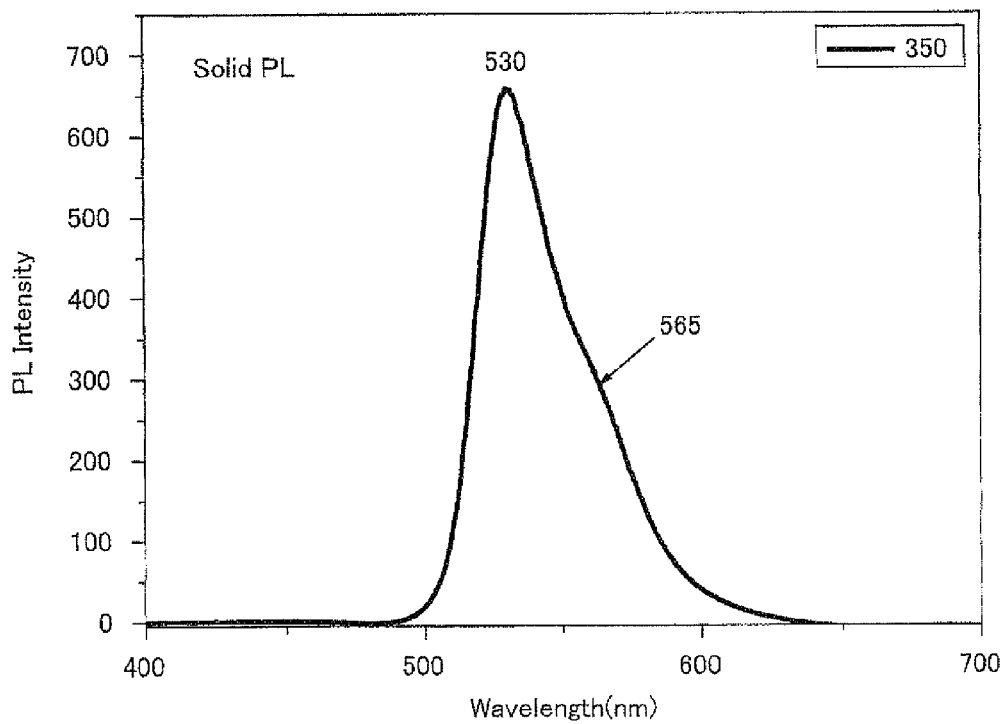
FIG. 16 shows a graph of a PL spectrum of the compound of FIG. 15 observed in a solid-phase state.

FIG. 16 shows a PL spectrum of the Ir(ppy)$_2$didpg observed in a solid-phase state. Photoluminescence of the Ir(ppy)$_2$didpg in a solid-phase state exhibited a maximum value at a wavelength of 530 nm.

Example 8

Synthesis of Ir(dfppy)$_2$didpg, and Measurement of Absorption and Photoluminescence of Ir(dfppy)$_2$didpg (Synthesis of Cyclometalated Ir(III)μ-Chloro-Bridged Precursor)

A cyclometalated Ir(III)$_p$-chloro-bridged dimer (primary metal complex), i.e., [(dfppy)$_2$Ir(μ-Cl)]$_2$, was synthesized in the following manner.

Initially, in a solvent containing 2-ethoxyethanol and water by a ratio of 3:1, IrCl$_3$.H$_2$O (2.35 mmol, 0.702 g) and 2-(2,4-difluorophenyl)pyridine (10.5 mmol, 2.00 g) were caused to coexist with each other, and refluxed at 140° C. for 24 hours. Subsequently, an obtained reactant mixture was cooled down, and a reactant product was precipitated.

After that, the reactant mixture containing a precipitate (the reactant product) was filtered. Subsequently, a residue obtained by the filtering was washed with a solution containing acetone (60 ml):ethanol (60 ml), so as to obtain a crude product. The crude product was recrystallized by a solution of n-hexane (10 ml):toluene (25 ml), so as to obtain yellow crystals. A yield of the μ-chloro-bridged dimer was 70%. The obtained product was subjected to NMR analysis, so as to confirm that the product was an intended compound. The following shows a result of the analysis.

$^1$H NMR (300 MHz in CDCl$_3$, rt) δ=9.15 (d, 2H), 8.32 (d, 2H), 7.86 (dd, 2H), 6.84 (dd, 2H), 6.36 (dd, 2H), 5.34 (dd, 2H).

(Synthesis of Ir(dfppy)$_2$didpg)

In a 100-ml flask in argon atmosphere, 10 ml of THF containing diphenylamine (67 mg, 0.4 mmol), and a hexane solution of n-BuLi (2.77 M, 0.4 mmol, 0.14 ml) were added, and stirred at a room temperature for about 2 hours. Then, N,N'-diisopropyl carbodiimide (50 mg, 0.4 mmol) was dropped into an obtained reactant solution. The reactant solution was quickly stirred for 2 hours, and then dropped into 15 ml of THF containing [(dfppy)$_2$Ir(μ-Cl)]$_2$ (0.2 mmol, 220 mg), and stirred at 80° C. for 12 hours.

Subsequently, an obtained reactant was cooled down to a room temperature, and then, the solvent was vaporized under a reduced pressure. A resultant product was washed with diethyl ether, thereby preparing a novel iridium complex, Ir(dfppy)$_2$didpg, according to the present invention. A yield thereof was 65%. The novel iridium complex thus obtained was subjected to NMR analysis, so as to confirm that it was an intended compound. The following shows a result of the analysis.

$^1$H NMR (300 MHz, CDCl$_3$, rt): δ=9.15 (d, 2H), 8.30 (d, 2H), 7.87 (t, 2H), 7.30 (m, 5H), 7.14 (m, 5H), 7.08 (t, 2H), 6.33-6.25 (m, 2H), 5.70 (dd, 2H), 3.61-3.53 (m, 2H), 0.42 (d, 6H), 0.11 (d, 6H).

(Measurement of Absorption Spectrum and PL Spectrum)

The measurement of an absorption spectrum and a PL spectrum of the obtained novel iridium complex was carried out in the same manner as in Example 2.

Figure 17:
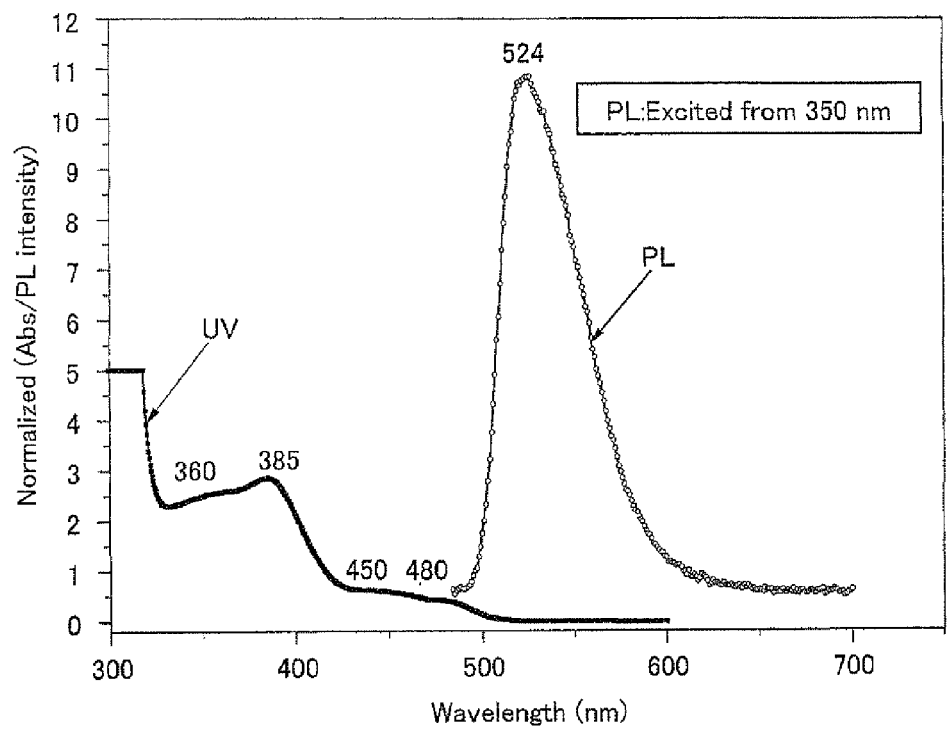
FIG. 17 shows graphs of a UV-vis absorption spectrum and a PL spectrum of another compound according to the present invention observed in degassed dichloromethane.

FIG. 17 shows a UV-vis absorption spectrum and a PL spectrum of the Ir(ppy)$_2$dipba. Photoluminescence of the Ir(ppy)$_2$dipba exhibited a maximum value at a wavelength of 524 nm.

Example 9

Synthesis of Ir(dfppy)$_2$dipba, and Measurement of Absorption and Photoluminescence of Ir(dfppy)$_2$dipba (Synthesis of Ir(dfppy)$_2$dipba)

In a 100-ml flask, 10 ml of THF containing N,N'-diisopropyl carbodiimide (50 mg, 0.4 mmol) was added, and a hexane solution of phenyllithium (Ph-Li: 0.21 ml, 0.4 mmol) was dropped thereto. An obtained reactant solution was quickly stirred at a room temperature for two hours. Then, the reactant solution was dropped into 15 ml of THF containing [(dfppy)$_2$Ir(μ-Cl)]$_2$ (0.2 mmol, 229 mg), and stirred at 80° C. for 12 hours.

Subsequently, an obtained reactant was cooled down to a room temperature, and the solvent was vaporized under a reduced pressure. Then, a resultant product was washed with diethyl ether, thereby preparing a novel iridium complex, Ir(dfppy)$_2$dipba, according to the present invention. A yield thereof was 70%. The novel iridium complex thus obtained was subjected to NMR analysis, so as to confirm that it was an intended compound. The following shows a result of the analysis.

$^1$H NMR (300 MHz, CDCl$_3$, rt): δ=9.32 (d, 2H), 8.29 (d, 2H), 7.81 (t, 2H), 7.44 (m, 2H), 7.29 (m, 5H), 6.32 (dtd, 2H), 5.75 (dd, 2H), 3.23-3.16 (m, 2H), 0.67 (d, 6H), −0.08 (d, 6H).

(Measurement of Absorption Spectrum and PL Spectrum)

The measurement of an absorption spectrum and a PL spectrum of the obtained novel iridium complex was carried out in the same manner as in Example 2.

Figure 18:
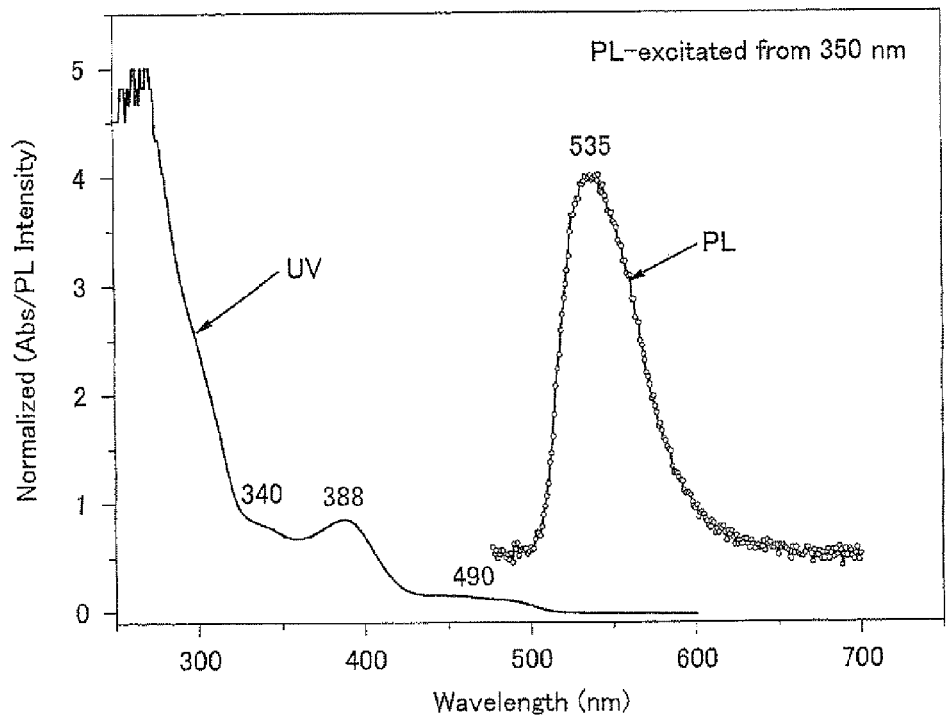
FIG. 18 shows graphs of a UV-vis absorption spectrum and a PL spectrum of another compound according to the present invention observed in degassed dichloromethane.

FIG. 18 shows a UV-vis absorption spectrum and a PL spectrum of the Ir(dfppy)$_2$dipba observed in degassed dichloromethane. Photoluminescence of the Ir(dfppy)$_2$dipba in degassed dichloromethane exhibited a maximum value at a wavelength of 535 nm.

Figure 19:
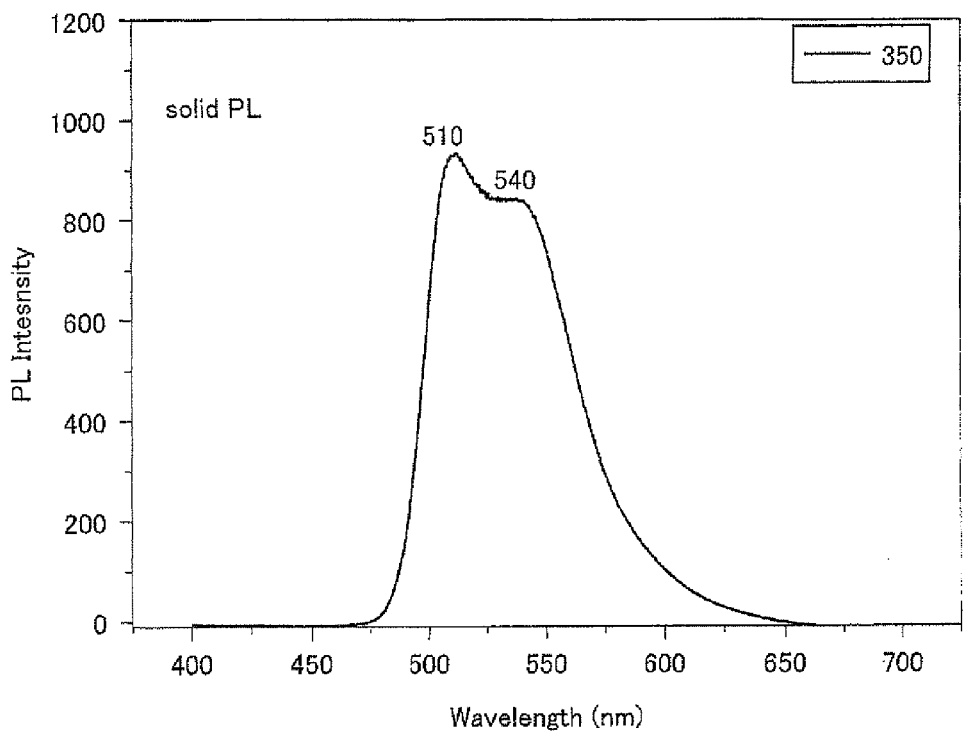
FIG. 19 shows a graph of a PL spectrum of the compound of FIG. 18 observed in a solid-phase state.

FIG. 19 shows a PL spectrum of the Ir(dfppy)$_2$dipba observed in a solid-phase state. Photoluminescence of the Ir(dfppy)$_2$dipba in a solid-phase state exhibited a first maximum value at a wavelength of 510 nm and a second maximum value at a wavelength of 540 nm. The intensity of photoluminescence was larger at the first maximum value than at the second maximum value.

Example 10

Synthesis of Ir(ppy)₂tbu-ba, and Measurement of Absorption and Photoluminescence of Ir(ppy)₂tbu-ba (Synthesis of Ir(ppy)₂tbu-ba)

Into a 100-ml flask, 10 ml of THF containing N,N'-di-tert-butyl carbodiimide (62 mg, 0.4 mmol) was added, and a hexane solution of phenyllithium (Ph-Li: 0.21 ml, 0.4 mmol) was dropped thereto. An obtained reactant solution was quickly stirred at a room temperature for two hours. Then, the reactant solution was dropped into 15 ml of THF containing [(ppy)₂Ir(μ-Cl)]₂ (0.2 mmol, 220 mg), and stirred at 80° C. for 12 hours.

Subsequently, an obtained reactant was cooled down to a room temperature, and the solvent was vaporized under a reduced pressure. Then, a resultant product was washed with diethyl ether, thereby preparing a novel iridium complex, Ir(ppy)₂tbu-ba, according to the present invention. A yield thereof was 70%. The novel iridium complex thus obtained was subjected to NMR analysis, so as to confirm that it was an intended compound. The following shows a result of the analysis.

$^1$H NMR (300 MHz, C$_6$D$_6$, rt): δ=9.65 (d, 2H), 7.53-7.46 (m, 4H), 7.38 (t, 2H), 7.11-7.02 (m, 6H), 6.81-6.72 (m, 5H), 6.66 (d, 2H), 0.73 (s, 18H).

(Measurement of Absorption Spectrum and PL Spectrum)

The measurement of an absorption spectrum and a PL spectrum of the obtained novel iridium complex was carried out in the same manner as in Example 2.

Figure 20:
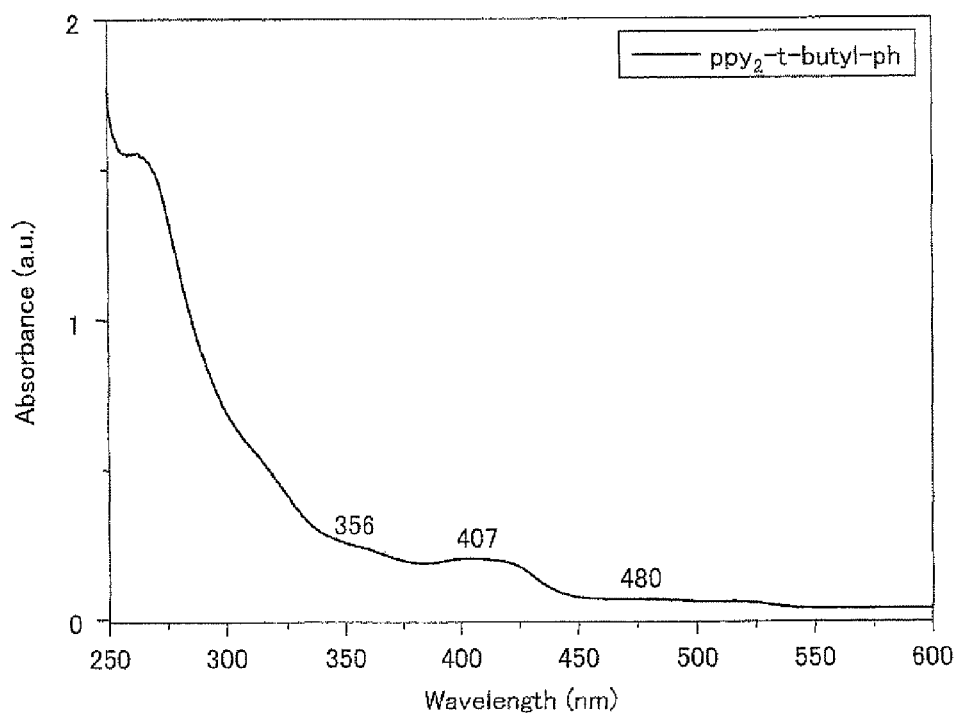
FIG. 20 shows a graph of a UV-vis absorption spectrum of another compound according to the present invention observed in chloroform.

FIG. 20 shows a UV-vis absorption spectrum of the Ir(ppy)₂tbu-ba observed in a chloroform solution.

Figure 21:
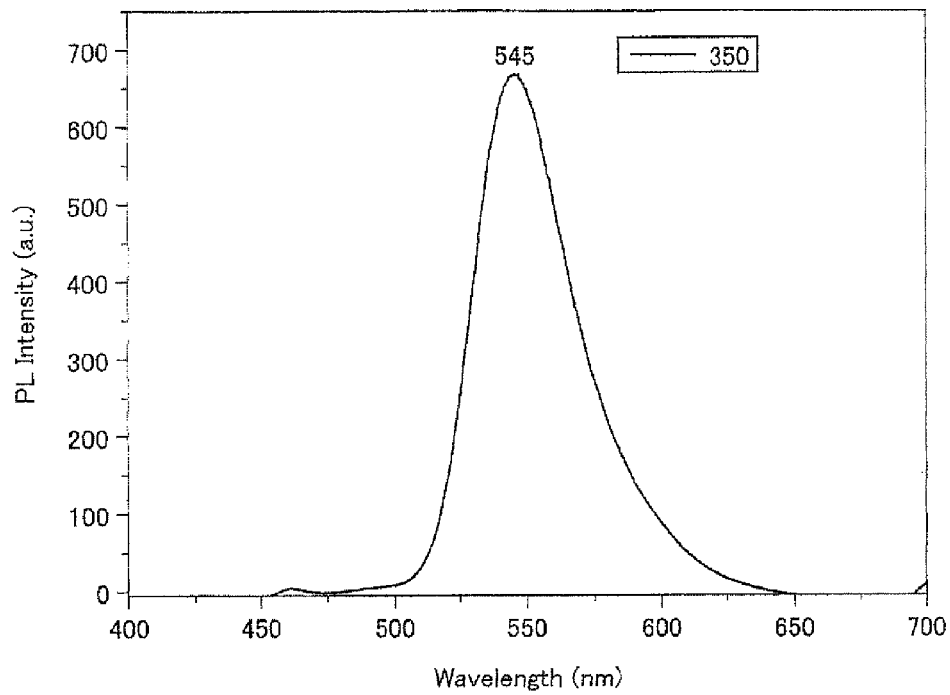
FIG. 21 shows a graph of a PL spectrum of the compound of FIG. 20 observed in chloroform.

FIG. 21 shows a PL spectrum of the Ir(ppy)₂tbu-ba observed in a chloroform solution. Photoluminescence of the Ir(ppy)₂tbu-ba in a chloroform solution exhibited a maximum value at a wavelength of 545 nm.

Figure 22:
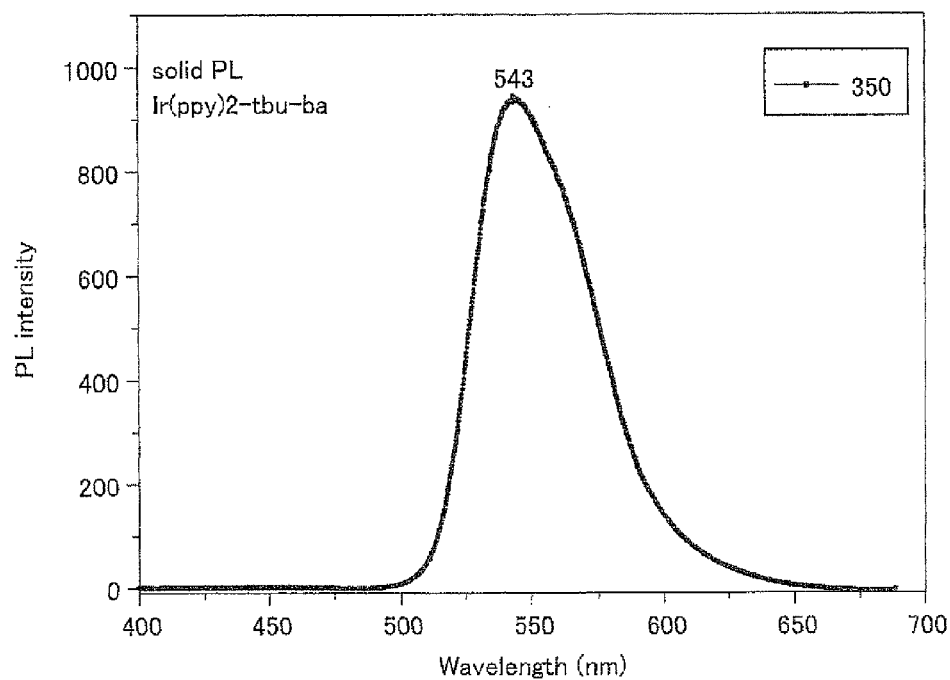
FIG. 22 shows a graph of a PL spectrum of the compound of FIG. 20 observed in a solid-phase state.

FIG. 22 shows a PL spectrum of the Ir(ppy)₂tbu-ba observed in a solid-phase state. Photoluminescence of the Ir(ppy)₂tbu-ba in a solid-phase state exhibited a maximum value at a wavelength of 543 nm.

Example 11

Synthesis of Ir(bzq)₂dip-dpg, and Measurement of Absorption and Photoluminescence of Ir(bzq)₂dip-dpg (Synthesis of Ir(bzq)₂dip-dpg)

In a 100-ml flask, 10 ml of THF containing diphenylamine (67 mg, 0.4 mmol), and a hexane solution of n-BuLi (2.77 M, 0.4 mmol, 0.14 ml) were added and stirred in argon atmosphere at a room temperature for 2 hours. Then, N,N'-diisopropyl carbodiimide (50 mg, 0.4 mmol) was dropped into an obtained reactant solution. The reactant solution was quickly stirred for two hours. Then, the reactant solution was dropped into 15 ml of THF containing [(bzq)₂Ir(μ-Cl)]₂ (0.2 mmol, 230 mg), and stirred at 80° C. for 12 hours.

Subsequently, an obtained reactant was cooled down to a room temperature, and the solvent was vaporized under a reduced pressure. Then, a resultant product was washed with diethyl ether, thereby preparing a novel iridium complex, Ir(bzq)₂dip-dpg, according to the present invention. A yield thereof was 80%. The novel iridium complex thus obtained was subjected to NMR analysis, so as to confirm that it was an intended compound. The following shows a result of the analysis.

$^1$H NMR (300 MHz, CDCl$_3$, rt): δ=9.50 (d, 2H), 8.28 (d, 2H), 7.76-7.61 (m, 5H), 7.29 (t, 5H), 7.21 (t, 5H), 7.03-6.92 (tt, 5H), 6.36 (d, 2H), 3.56 (m, 2H), 0.44 (d, 6H), −0.31 (d, 6H).

(Measurement of Absorption Spectrum and PL Spectrum)

The measurement of an absorption spectrum and a PL spectrum of the obtained novel iridium complex was carried out in the same manner as in Example 2.

Figure 23:
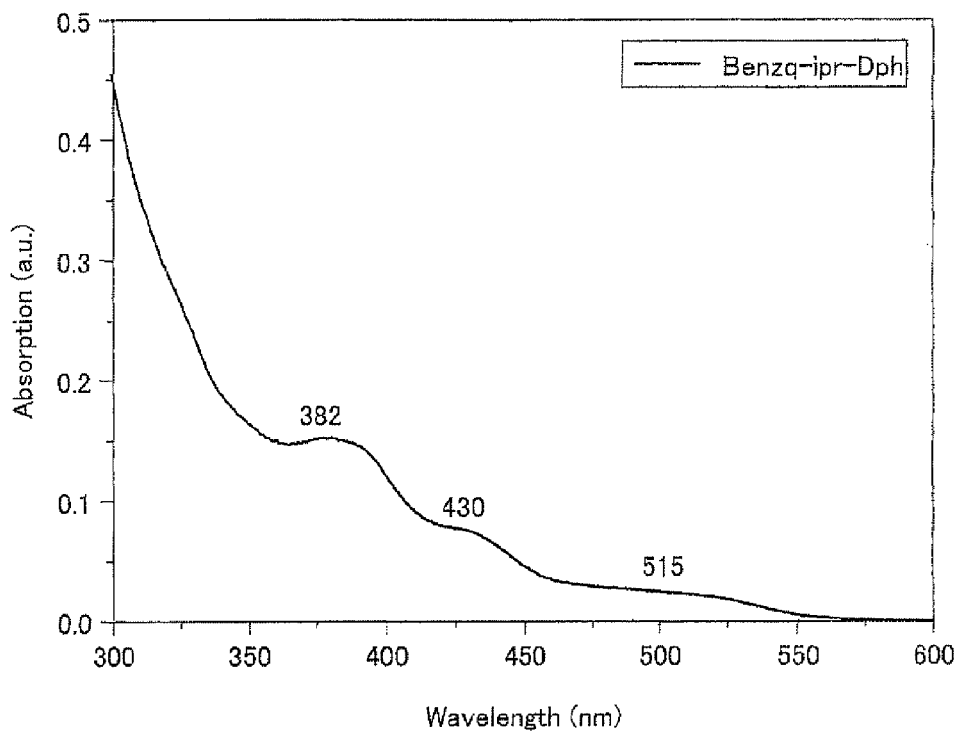
FIG. 23 shows a graph of a UV-vis absorption spectrum of another compound according to the present invention observed in chloroform.

FIG. 23 shows a UV-vis absorption spectrum of the Ir(bzq)₂dip-dpg observed in a chloroform solution.

Figure 24:
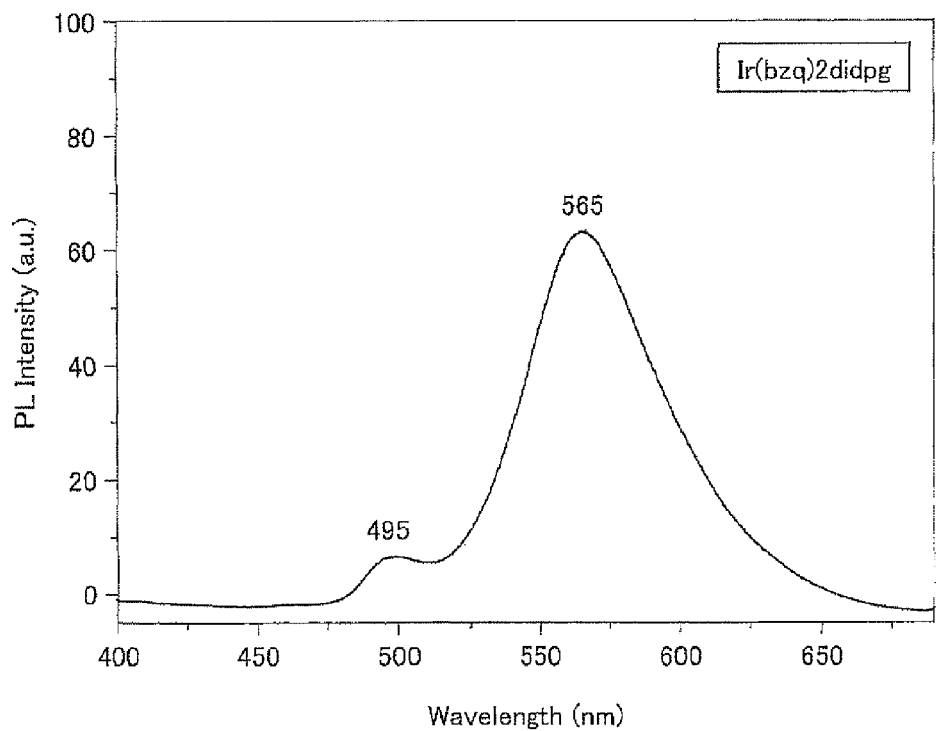
FIG. 24 shows a graph of a PL spectrum of the compound of FIG. 23 observed in chloroform.

FIG. 24 shows a PL spectrum of the Ir(bzq)₂dip-dpg observed in a chloroform solution. Photoluminescence of the Ir(bzq)₂dip-dpg in a chloroform solution exhibited a maximum value at a wavelength of 565 nm.

Figure 25:
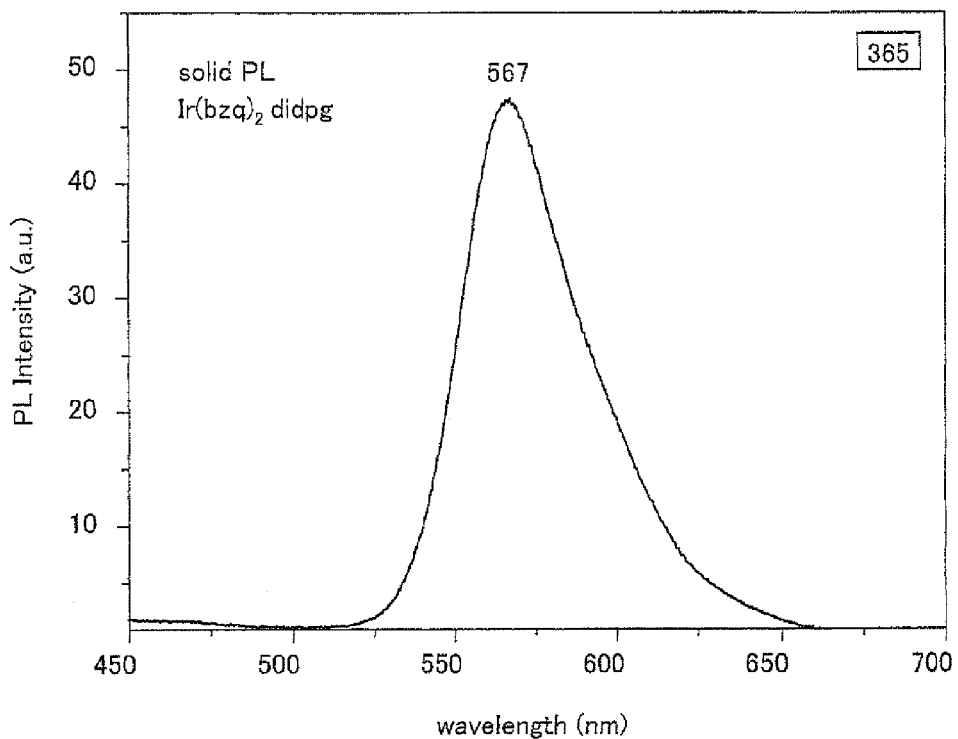
FIG. 25 shows a graph of a PL spectrum of the compound of FIG. 23 observed in a solid-phase state.

FIG. 25 shows a PL spectrum of the Ir(bzq)₂dip-dpg observed in a solid-phase state. Photoluminescence of the Ir(bzq)₂dip-dpg in a solid-phase state exhibited a maximum value at a wavelength of 567 nm.

Example 12

Synthesis of Ir(ppy)₂(dipdg), and Measurement of Absorption and Photoluminescence of Ir(ppy)₂(dipdg)

(Synthesis of Ir(ppy)₂(dipdg))

Synthesis was carried out in the same manner as in Example 7 except that THF containing diallylamine (39 mg, 0.4 mmol) was used instead of the THF containing diphenylamine (67 mg, 0.4 mmol).

After toluene was vaporized, an obtained product was washed with diethyl ether, thereby preparing a novel iridium complex, Ir(ppy)₂(dipdg), according to the present invention. A yield thereof was 50%. The novel iridium complex thus obtained was subjected to NMR analysis, so as to confirm that it was an intended compound. The following shows a result of the analysis.

$^1$H NMR (300 MHz, C$_4$D$_8$O, rt): δ=9.20 (d, 2H), 7.95 (t, 2H), 7.80 (t, 2H), 7.60 (t, 2H), 7.20 (m, 2H), 6.70 (t, 2H), 6.50 (t, 2H), 6.30 (d, 2H), 6.15 (d, 2H), 4.95 (m, 2H), 3.65 (m, 2H), 1.65 (d, 4H), 0.72 (d, 6H), 0.61 (d, 6H).

(Measurement of Absorption Spectrum and PL Spectrum)

The measurement of an absorption spectrum and a PL spectrum of the obtained novel iridium complex was carried out in the same manner as in Example 2.

Figure 26:
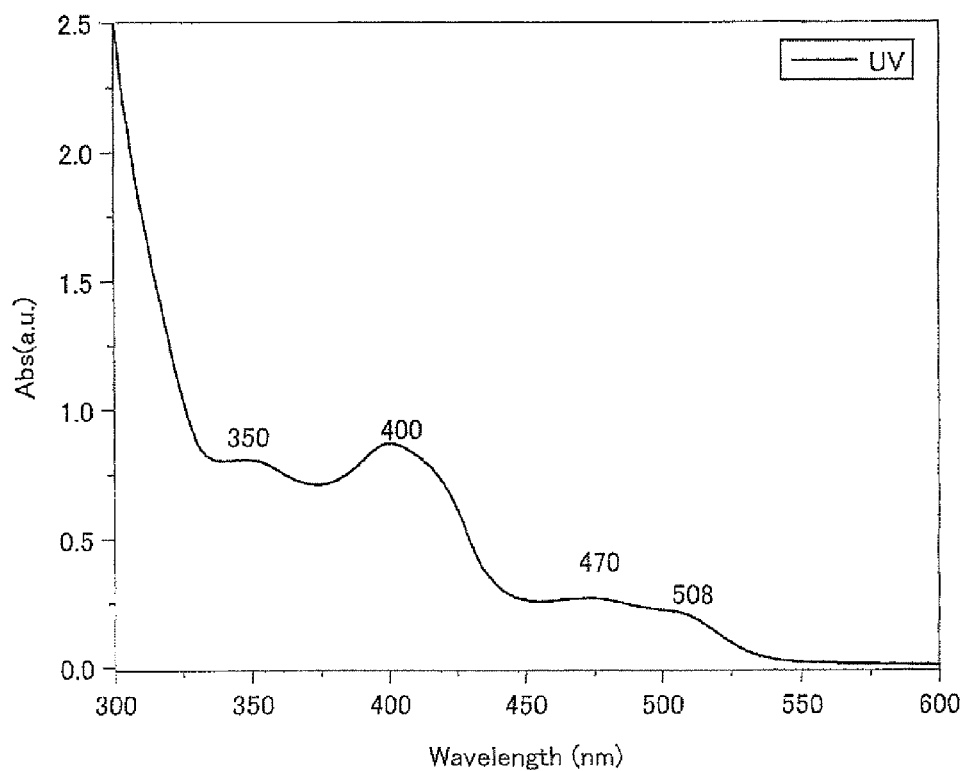
FIG. 26 shows a graph of a UV-vis absorption spectrum of another compound according to the present invention observed in chloroform.

FIG. 26 shows a UV-vis absorption spectrum of the Ir(ppy)₂(dipdg) observed in a chloroform solution.

Figure 27:
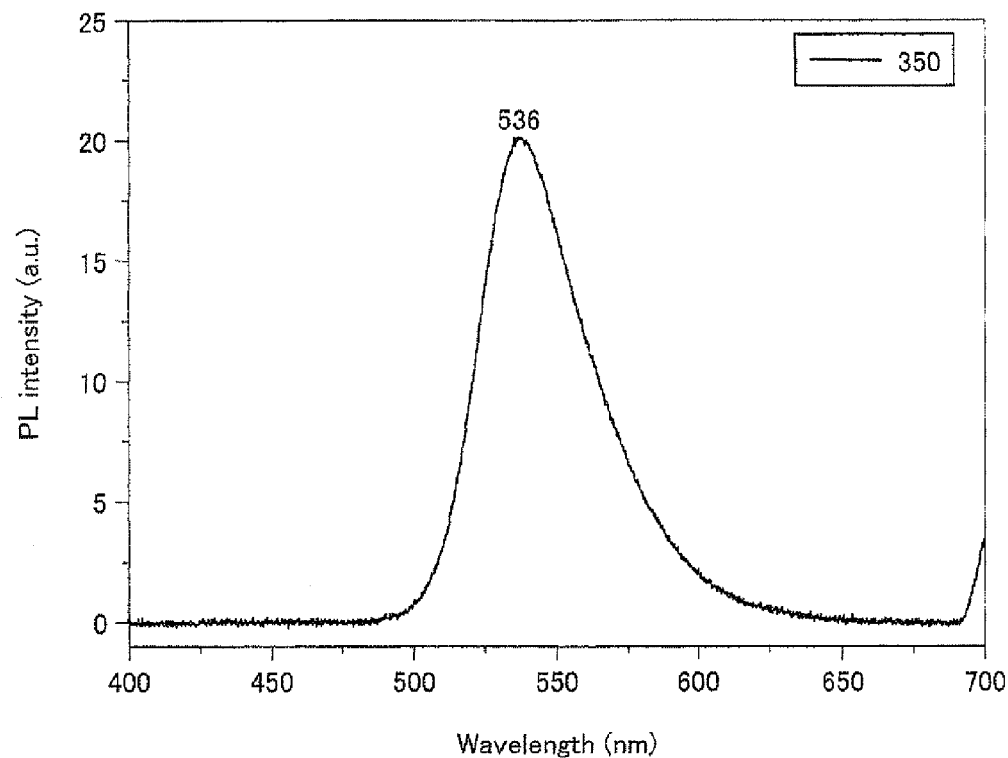
FIG. 27 shows a graph of a PL spectrum of the compound of FIG. 26 observed in chloroform.

FIG. 27 shows a PL spectrum of the Ir(ppy)₂(dipdg) observed in a chloroform solution. Photoluminescence of the Ir(ppy)₂(dipdg) in a chloroform solution exhibited a maximum value at a wavelength of 536 nm.

Figure 28:
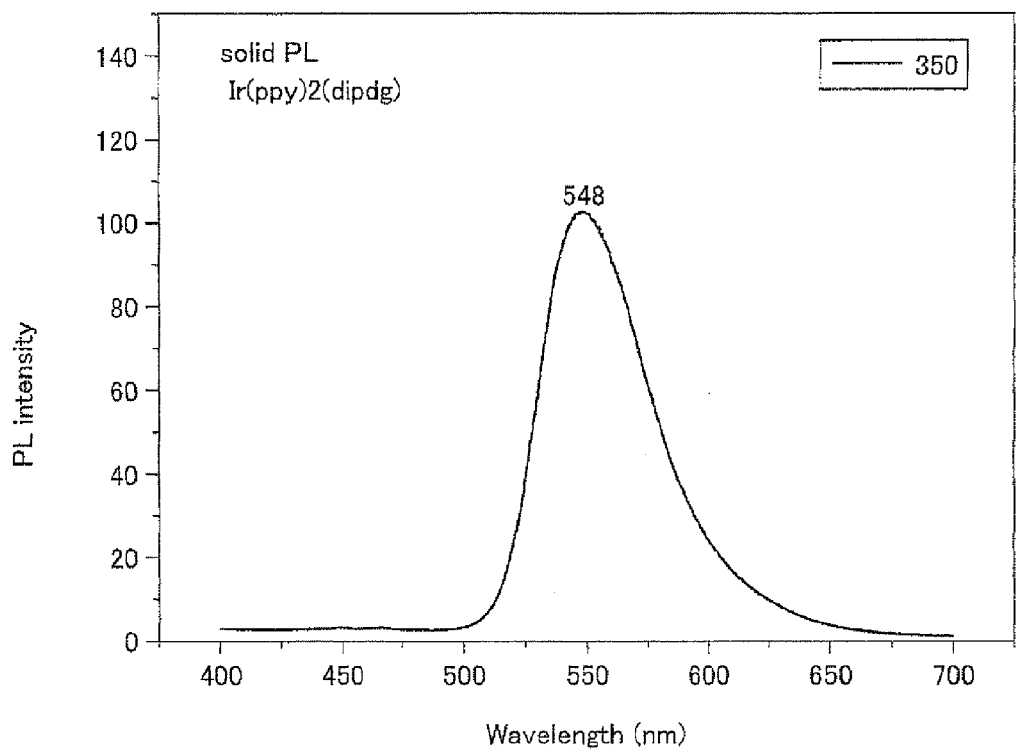
FIG. 28 shows a graph of a PL spectrum of the compound of FIG. 26 observed in a solid-phase state.

FIG. 28 shows a PL spectrum of the Ir(ppy)₂(dipdg) observed in a solid-phase state. Photoluminescence of the Ir(ppy)₂(dipdg) in a solid-phase state exhibited a maximum value at a wavelength of 548 nm.

Example 13

Synthesis of Ir(ppy)₂(dipdeg), and Measurement of Absorption and Photoluminescence of Ir(ppy)₂(dipdeg)

(Synthesis of Ir(ppy)₂(dipdeg))

Synthesis was carried out in the same manner as in Example 7 except that THF containing diethylamine (29 mg, 0.4 mmol) was used instead of the THF containing diphenylamine (67 mg, 0.4 mmol).

After toluene was vaporized, an obtained product was washed with diethyl ether, thereby preparing a novel iridium complex, Ir(ppy)$_2$(dipdeg), according to the present invention. A yield thereof was 60%. The novel iridium complex thus obtained was subjected to NMR analysis, so as to confirm that it was an intended compound. The following shows a result of the analysis.

$^1$H NMR (300 MHz, CDCl$_3$, rt): δ=9.25 (d, 2H), 7.95 (d, 2H), 7.75 (t, 2H), 7.56 (d, 2H), 7.20 (t, 2H), 6.66 (t, 2H), 6.49 (t, 2H), 6.23 (d, 2H), 3.75-3.67 (m, 2H), 3.23-3.02 (m, 4H), 1.11 (t, 6H), 0.77 (d, 6H), −0.012 (d, 6H).

(Measurement of Absorption Spectrum and PL Spectrum)

The measurement of an absorption spectrum and a PL spectrum of the obtained novel iridium complex was carried out in the same manner as in Example 2.

Figure 29:
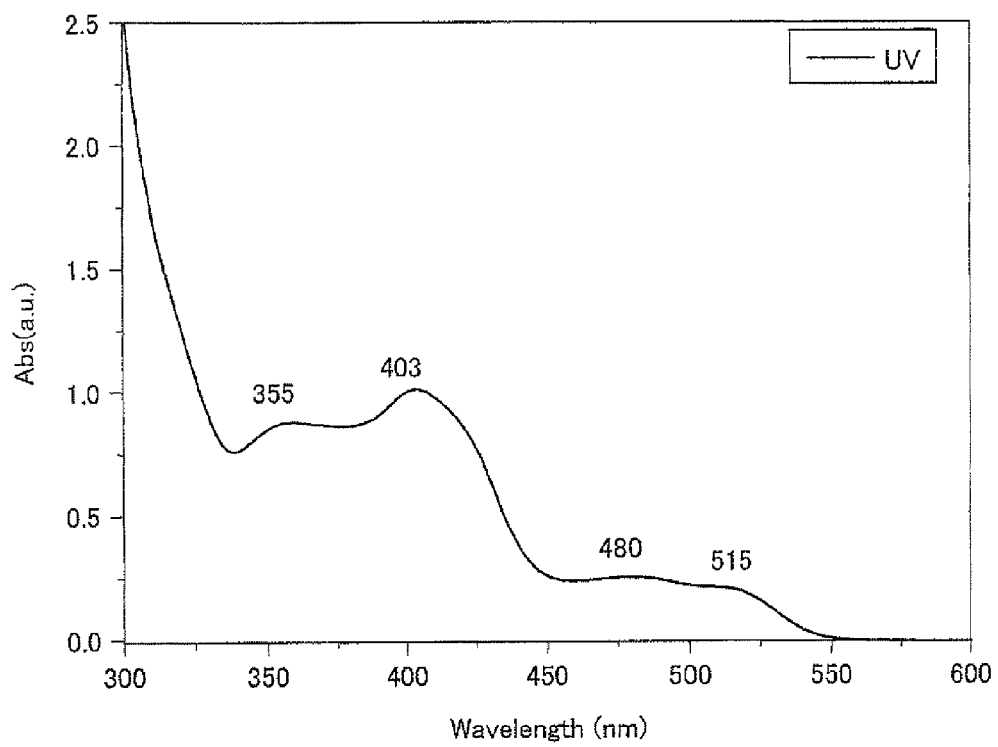
FIG. 29 shows a graph of a UV-vis absorption spectrum of another compound according to the present invention observed in chloroform.

FIG. 29 shows a UV-vis absorption spectrum of the Ir(ppy)$_2$(dipdeg) observed in a chloroform solution.

Figure 30:
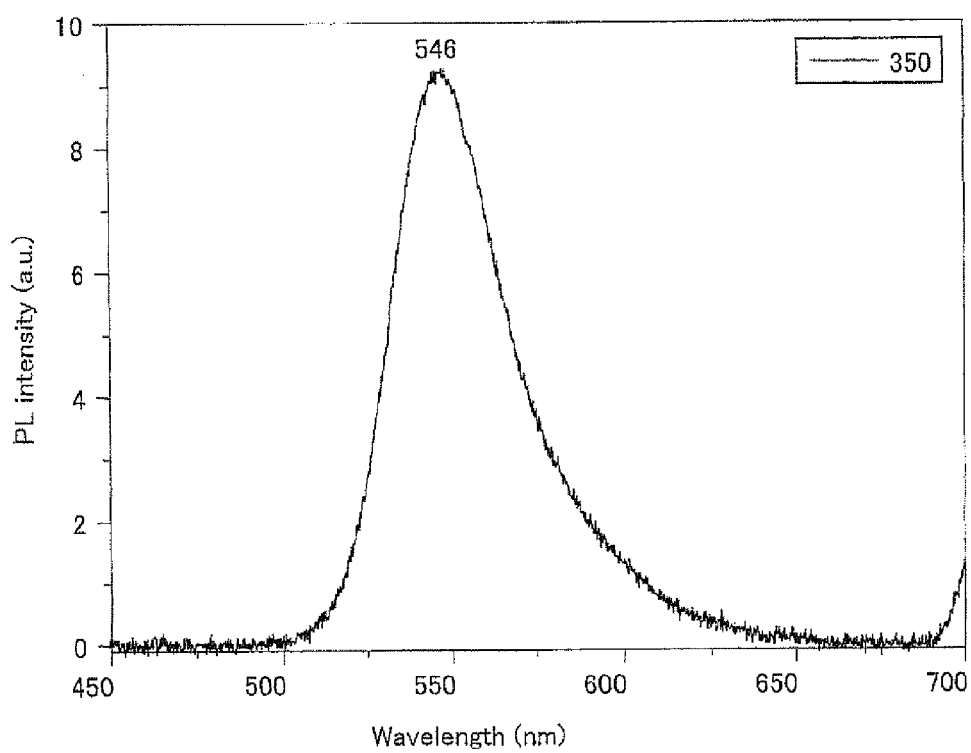
FIG. 30 shows a graph of a PL spectrum of the compound of FIG. 29 observed in chloroform.

FIG. 30 shows a PL spectrum of the Ir(ppy)$_2$(dipdeg) observed in a chloroform solution. Photoluminescence of the Ir(ppy)$_2$(dipdeg) in a chloroform solution exhibited a maximum value at a wavelength of 546 nm.

Figure 31:
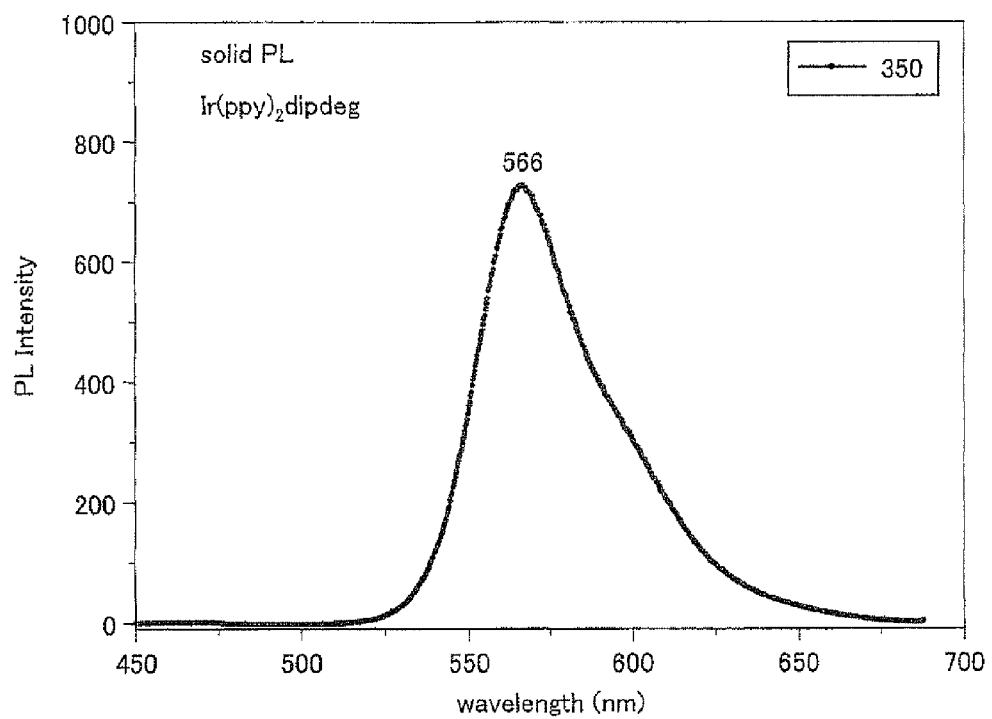
FIG. 31 shows a graph of a PL spectrum of the compound of FIG. 29 observed in a solid-phase state.

FIG. 31 shows a PL spectrum of the Ir(ppy)$_2$(dipdeg) observed in a solid-phase state. Photoluminescence of the Ir(ppy)$_2$(dipdeg) in a solid-phase state exhibited a maximum value at a wavelength of 566 nm.

Example 14

Synthesis of Ir(ppy)$_2$(dipdbg), Measurement of Absorption and Photoluminescence of Ir(ppy)$_2$(dipdbg)

(Synthesis of Ir(ppy)$_2$(dipdbg))

Synthesis was carried out in the same manner as in Example 7 except that THF containing diisobutyl amine (52 mg, 0.4 mmol) was used instead of the THF containing diphenylamine (67 mg, 0.4 mmol).

After toluene was vaporized, an obtained product was washed with diethyl ether, thereby preparing a novel iridium complex, Ir(ppy)$_2$(dipdbg), according to the present invention. A yield thereof was 65%. The novel iridium complex thus obtained was subjected to NMR analysis, so as to confirm that it was an intended compound. The following shows a result of the analysis.

$^1$H NMR (300 MHz, C$_4$D$_8$O, rt): δ=9.25 (d, 2H), 7.92 (d, 2H), 7.74 (t, 2H), 7.54 (d, 2H), 7.20-7.16 (m, 2H), 6.64 (t, 6.51 (t, 2H), 6.22 (d, 2H), 3.84 (m, 2H), 2.96-2.85 (m, 4H), 1.93-1.85 (m, 2H), 0.94 (dd, 12H), 0.85 (d, 12H).

(Measurement of Absorption Spectrum and PL Spectrum)

The measurement of an absorption spectrum and a PL spectrum of the obtained novel iridium complex was carried out in the same manner as in Example 2.

Figure 32:
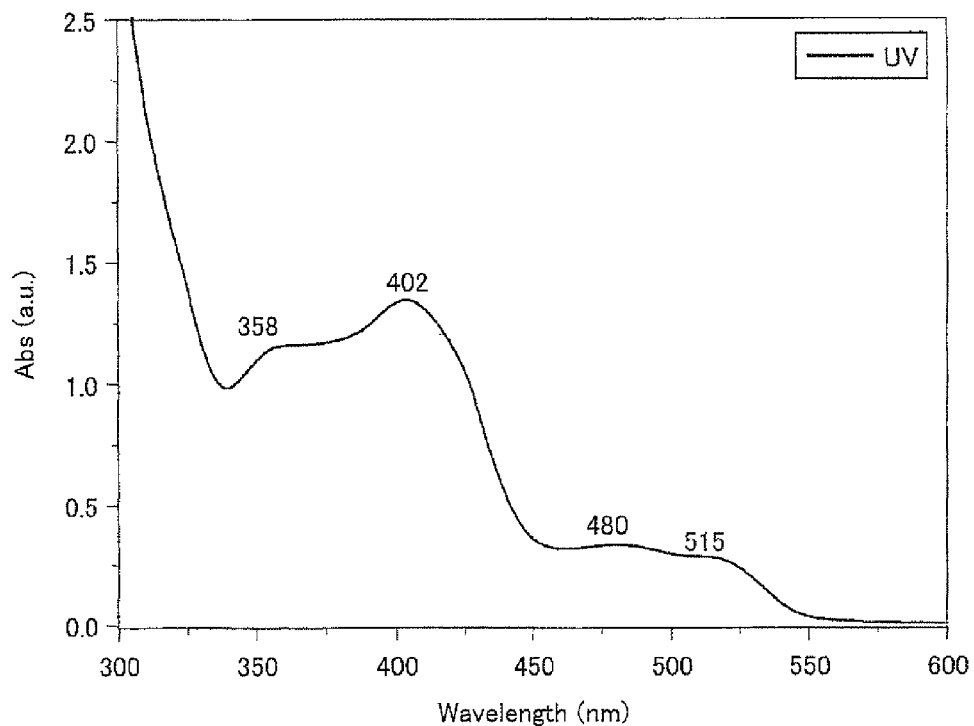
FIG. 32 shows a graph of a UV-vis absorption spectrum of another compound according to the present invention observed in chloroform.

FIG. 32 shows a UV-vis absorption spectrum of the Ir(ppy)$_2$(dipdbg) observed in a chloroform solution.

Figure 33:
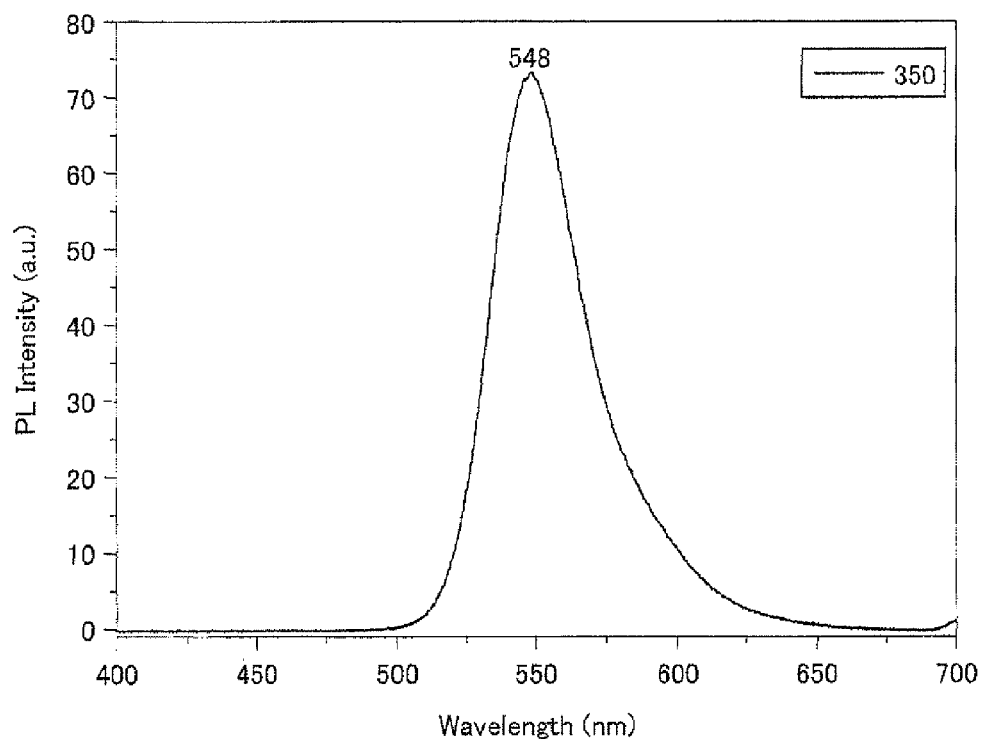
FIG. 33 shows a graph of a PL spectrum of the compound of FIG. 32 observed in chloroform.

FIG. 33 shows a PL spectrum of the Ir(ppy)$_2$(dipdbg) observed in a chloroform solution. Photoluminescence of the Ir(ppy)$_2$(dipdbg) in a chloroform solution exhibited a maximum value at a wavelength of 548 nm.

Figure 34:
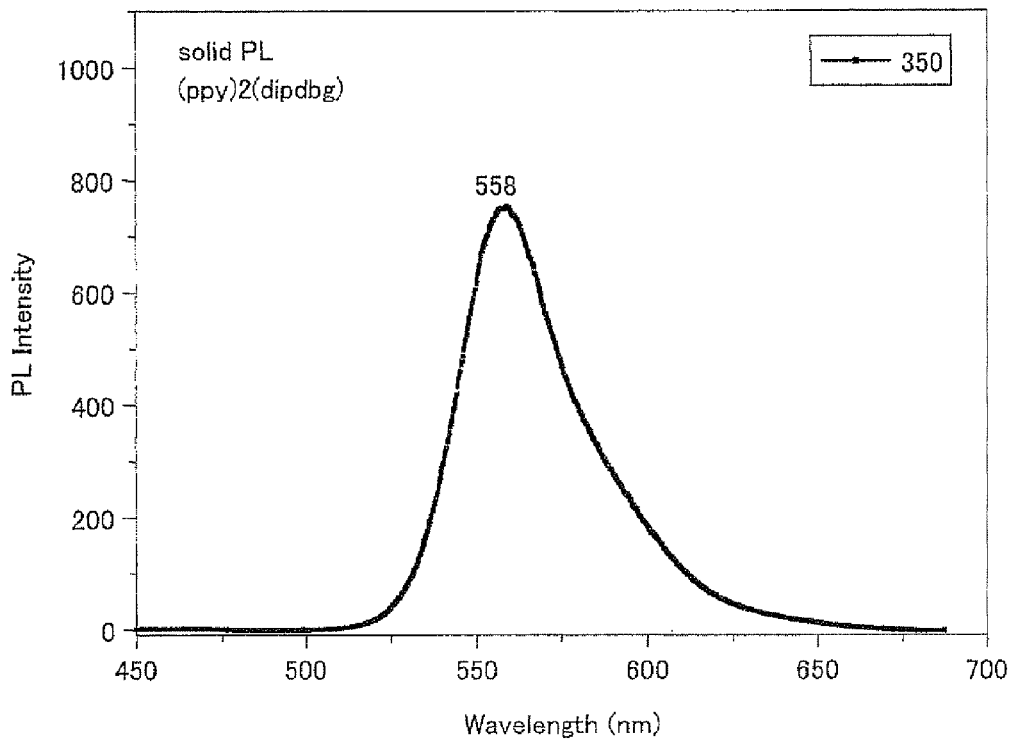
FIG. 34 shows a graph of a PL spectrum of the compound of FIG. 32 observed in a solid-phase state.

FIG. 34 shows a PL spectrum of the Ir(ppy)$_2$(dipdbg) observed in a solid-phase state. Photoluminescence of the Ir(ppy)$_2$(dipdbg) in a solid-phase state exhibited a maximum value at a wavelength of 558 nm.

Example 15

Synthesis of Ir(ppy)$_2$(dipgdip), Measurement of Absorption and Photoluminescence of Ir(ppy)$_2$(dipdbg)

(Synthesis of Ir(ppy)$_2$(dipgdip))

Synthesis was carried out in the same manner as in Example 7 except that THF containing diisopropylamine (40 mg, 0.4 mmol) was used instead of the THF containing diphenylamine (67 mg, 0.4 mmol).

After toluene was vaporized, an obtained product was washed with diethyl ether, thereby preparing a novel iridium complex, Ir(ppy)$_2$(dipgdip), according to the present invention. A yield thereof was 70%. The novel iridium complex thus obtained was subjected to NMR analysis, so as to confirm that it was an intended compound. The following shows a result of the analysis.

$^1$H NMR (300 MHz, C$_6$D$_6$, rt): δ=9.35 (d, 2H), 7.52 (d, 2H), 7.41 (d, 2H), 7.02 (t, 2H), 6.87-6.73 (m, 6H), 6.67 (t, 2H), 3.93-3.88 (m, 2H), 3.48-3.44 (m, 2H), 1.20 (t, 12H), 1.10 (d, 6H), 0.25 (d, 6H).

(Measurement of Absorption Spectrum and PL Spectrum)

The measurement of an absorption spectrum and a PL spectrum of the obtained novel iridium complex was carried out in the same manner as in Example 2.

Figure 35:
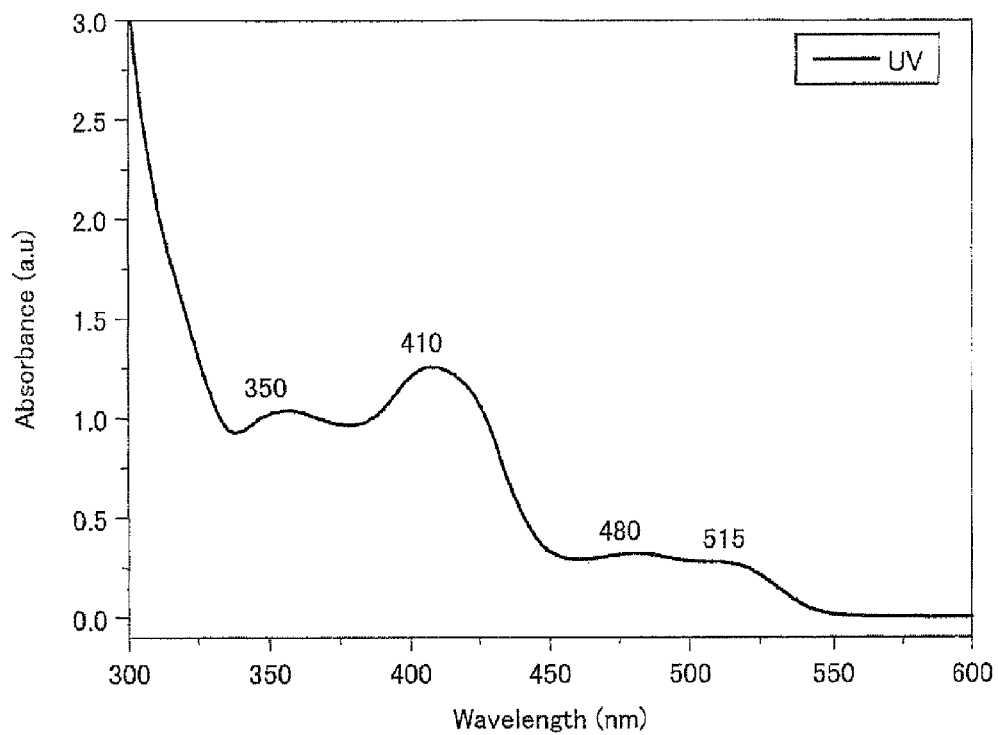
FIG. 35 shows a graph of a UV-vis absorption spectrum of another compound according to the present invention observed in chloroform.

FIG. 35 shows a UV-vis absorption spectrum of the Ir(ppy)$_2$(dipgdip) observed in a chloroform solution.

Figure 36:
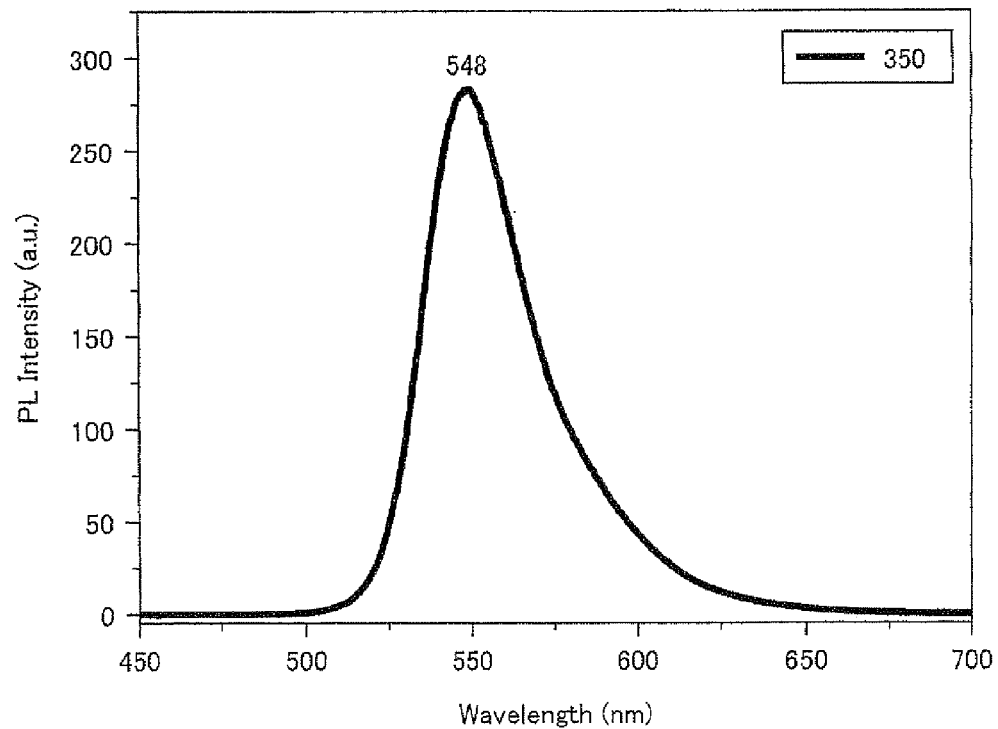
FIG. 36 shows a graph of a PL spectrum of the compound of FIG. 35 observed in chloroform.

FIG. 36 shows a PL spectrum of the Ir(ppy)$_2$(dipgdip) observed in a chloroform solution. Photoluminescence of the Ir(ppy)$_2$(dipgdip) in a chloroform solution exhibited a maximum value at a wavelength of 548 nm.

Figure 37:
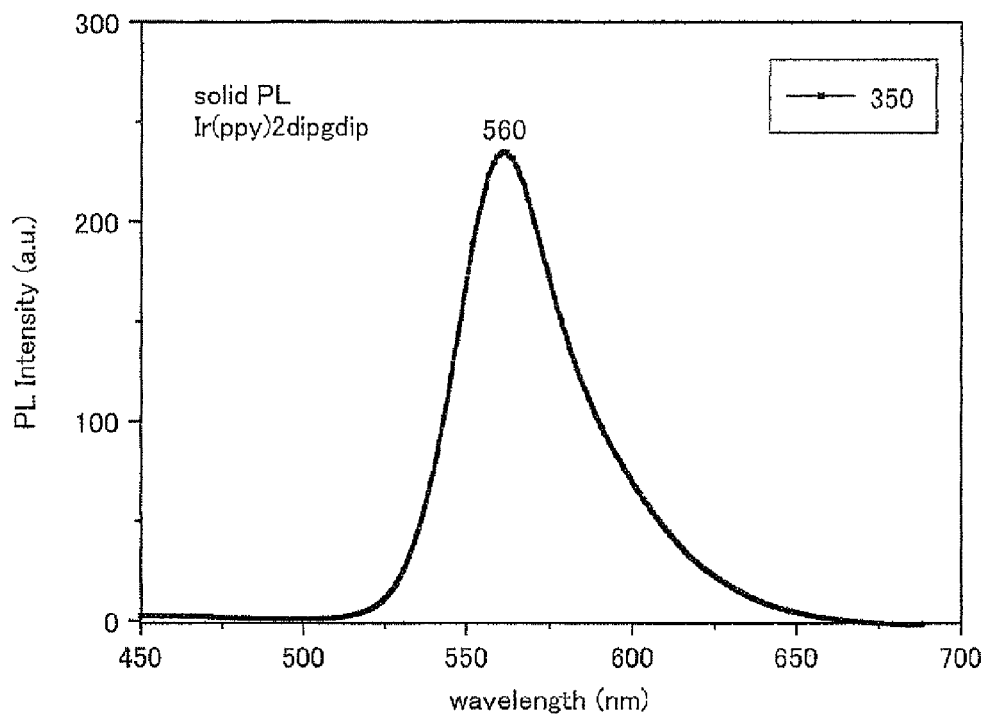
FIG. 37 shows a graph of a PL spectrum of the compound of FIG. 35 observed in a solid-phase state.

FIG. 37 shows a PL spectrum of the Ir(ppy)$_2$(dipgdip) observed in a solid-phase state. Photoluminescence of the Ir(ppy)$_2$(dipgdip) in a solid-phase state exhibited a maximum value at a wavelength of 560 nm.

Example 16

Synthesis of Ir(ppy)$_2$dip-dtmsg, and Measurement of Absorption and Photoluminescence of Ir(ppy)$_2$dip-dtmsg (Synthesis of Ir(ppy)$_2$dip-dtmsg)

In a 100-ml flask, 10 ml of THF containing lithium(bis-trimethylsilyl)amide (67 mg, 0.4 mmol) was added and stirred for 30 minutes. Subsequently, N,N'-diisopropyl carbodiimide (50 mg, 0.4 mmol) was dropped into an obtained reactant solution. The reactant solution was quickly stirred for two hours. Then, the reactant solution was dropped into 15 ml of THF containing [(ppy)$_2$Ir(μ-Cl)]$_2$ (0.2 mmol, 220 mg), and stirred at 80° C. for 12 hours.

Subsequently, an obtained reactant was cooled down to a room temperature, and the solvent was vaporized under a reduced pressure. The reactant was then added into 5 ml of toluene, and the toluene was vaporized. After that, a resultant product was washed with diethyl ether, thereby preparing a novel iridium complex, Ir(ppy)$_2$dip-dtmsg, according to the present invention. A yield thereof was 70%. The novel iridium complex thus obtained was subjected to NMR analysis, SP as to confirm that it was an intended compound. The following shows a result of the analysis.

$^1$H NMR (300 MHz, C$_6$D$_6$, rt): δ=9.45 (d, 2H), 7.50 (d, 2H), 7.43 (d, 2H), 7.09 (t, 2H), 6.85-6.71 (m, 6H), 6.64 (d, 2H), 3.93-3.88 (m, 2H), 1.09 (d, 6H), 0.34 (d, 6H), 0.28 (s, 18H).

(Measurement of Absorption Spectrum and PL Spectrum)

The measurement of an absorption spectrum and a PL spectrum of the obtained novel iridium complex was carried out in the same manner as in Example 2.

Figure 38:
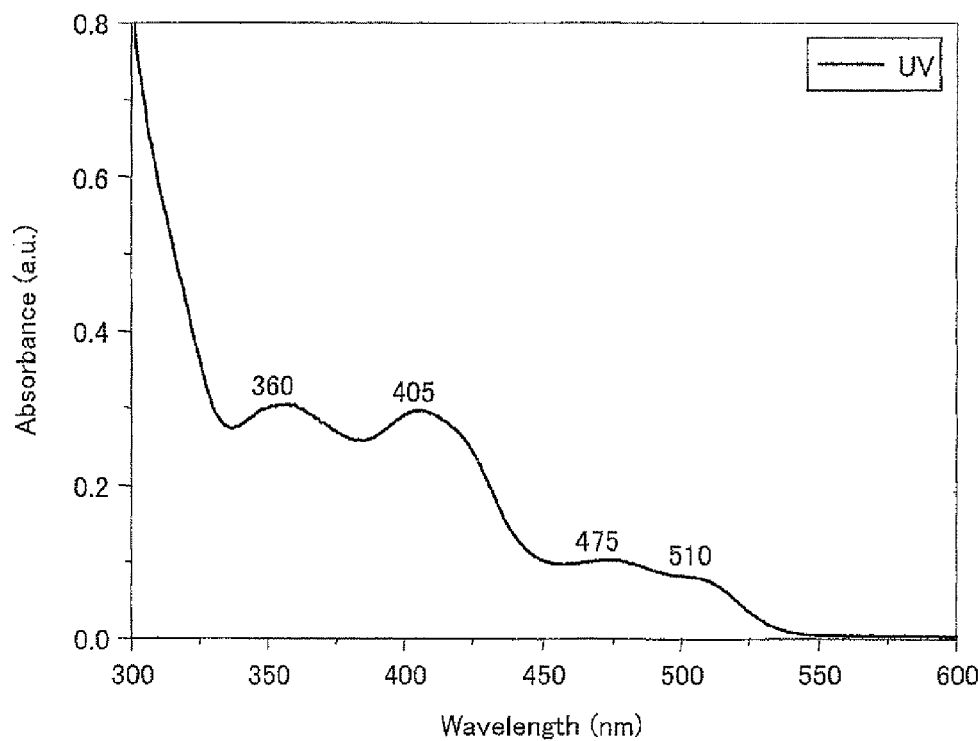
FIG. 38 shows a graph of a UV-vis absorption spectrum of another compound according to the present invention observed in chloroform.

FIG. 38 shows a UV-vis absorption spectrum of the Ir(ppy)$_2$dip-dtmsg observed in a chloroform solution.

Figure 39:
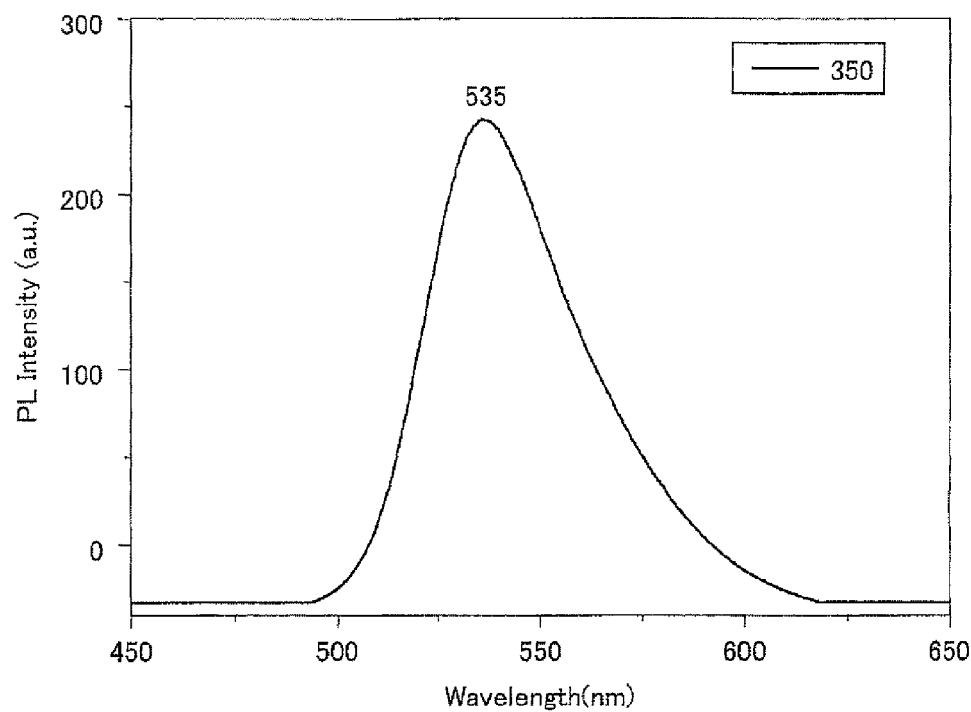
FIG. 39 shows a graph of a PL spectrum of the compound of FIG. 38 observed in chloroform.

FIG. 39 shows a PL spectrum of the Ir(ppy)$_2$dip-dtmsg observed in a chloroform solution. Photoluminescence of the Ir(ppy)$_2$dip-dtmsg in a chloroform solution exhibited a maximum value at a wavelength of 535 nm.

Figure 40:
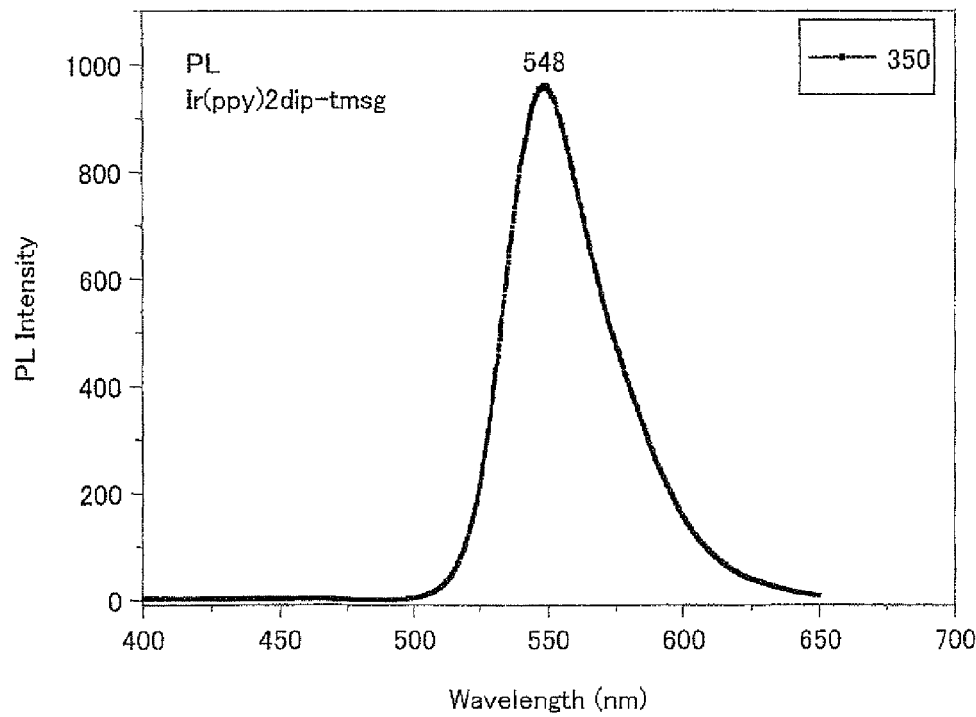
FIG. 40 shows a graph of a PL spectrum of the compound of FIG. 38 observed in a solid-phase state.

FIG. 40 shows a PL spectrum of the Ir(ppy)$_2$dip-dtmsg observed in a solid-phase state. Photoluminescence of the Ir(ppy)$_2$dip-dtmsg in a solid-phase state exhibited a maximum value at a wavelength of 548 nm.

Example 17

Synthesis of Ir(ppy)$_2$dip-cbzg, and Measurement of Absorption and Photoluminescence of Ir(ppy)$_2$dip-cbzg (Synthesis of Ir(ppy)$_2$dip-cbzg)

Synthesis was carried out in the same manner as in Example 7 except that THF containing carbazole (67 mg, 0.4 mmol) was used instead of the THF containing diphenylamine (67 mg, 0.4 mmol).

After toluene was vaporized, an obtained product was washed with diethyl ether, thereby preparing a novel iridium complex, Ir(ppy)$_2$dip-cbzg, according to the present invention. A yield thereof was 75%. The novel iridium complex thus obtained was subjected to NMR analysis, so as to confirm that it was an intended compound. The following shows a result of the analysis.

$^1$H NMR (300 MHz, CDCl$_3$, rt): δ=9.59 (d, 2H), 8.09 (d, 2H), 7.94 (d, 2H), 7.84 (t, 2H). 7.62 (dd, 4H), 7.50-7.38 (m, 6H), 6.84 (t, 2H), 6.73 (t, 2H), 6.42 (d, 2H), 3.06-3.02 (m, 2H), 0.64 (d, 6H), −0.06 (d, 6H).

(Measurement of Absorption Spectrum and PL Spectrum)

The measurement of an absorption spectrum and a PL spectrum of the obtained novel iridium complex was carried out in the same manner as in Example 2.

Figure 41:
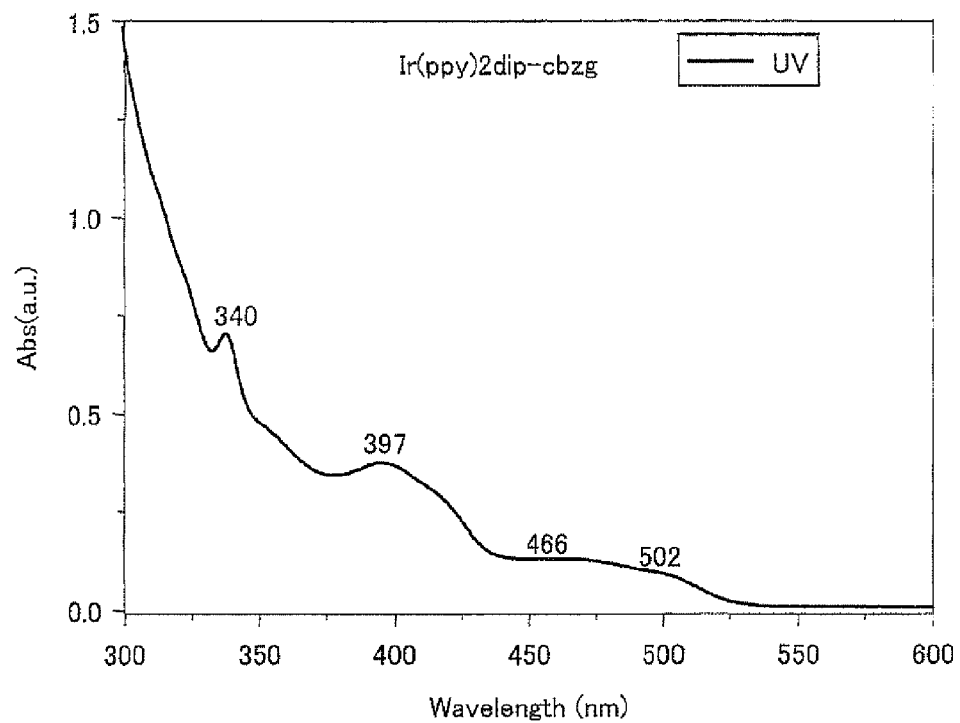
FIG. 41 shows a graph of a UV-vis absorption spectrum of another compound according to the present invention observed in chloroform.

FIG. 41 shows a UV-vis absorption spectrum of the Ir(ppy)$_2$dip-cbzg observed in a chloroform solution.

Figure 42:
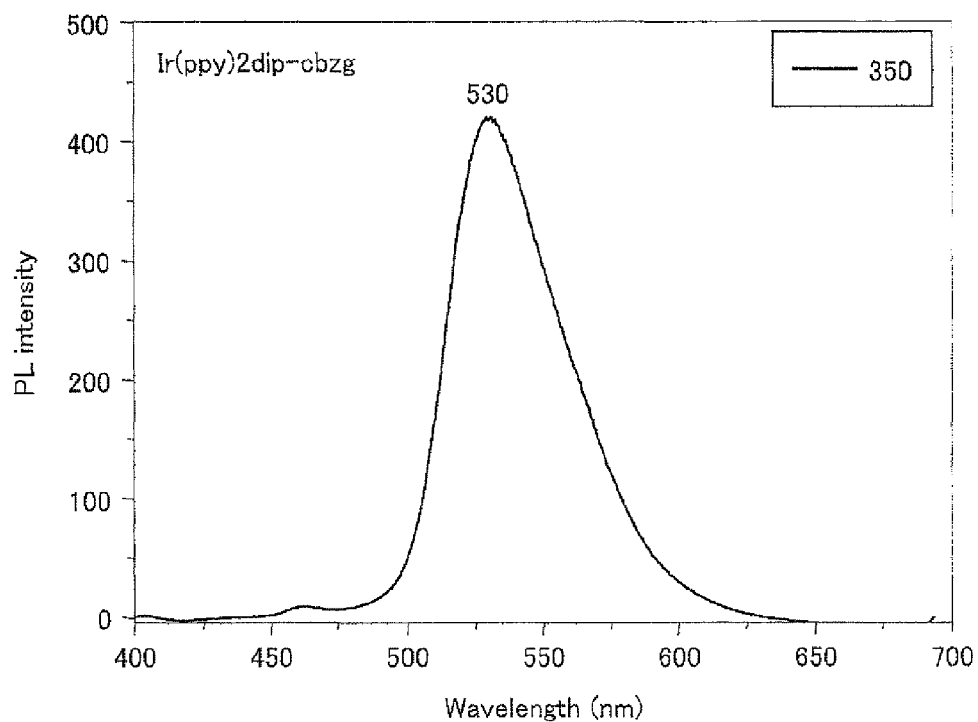
FIG. 42 shows a graph of a PL spectrum of the compound of FIG. 41 observed in chloroform.

FIG. 42 shows a PL spectrum of the Ir(ppy)$_2$dip-cbzg observed in a chloroform solution. Photoluminescence of the Ir(ppy)$_2$dip-cbzg in a chloroform solution exhibited a maximum value at a wavelength of 530 nm.

Figure 43:
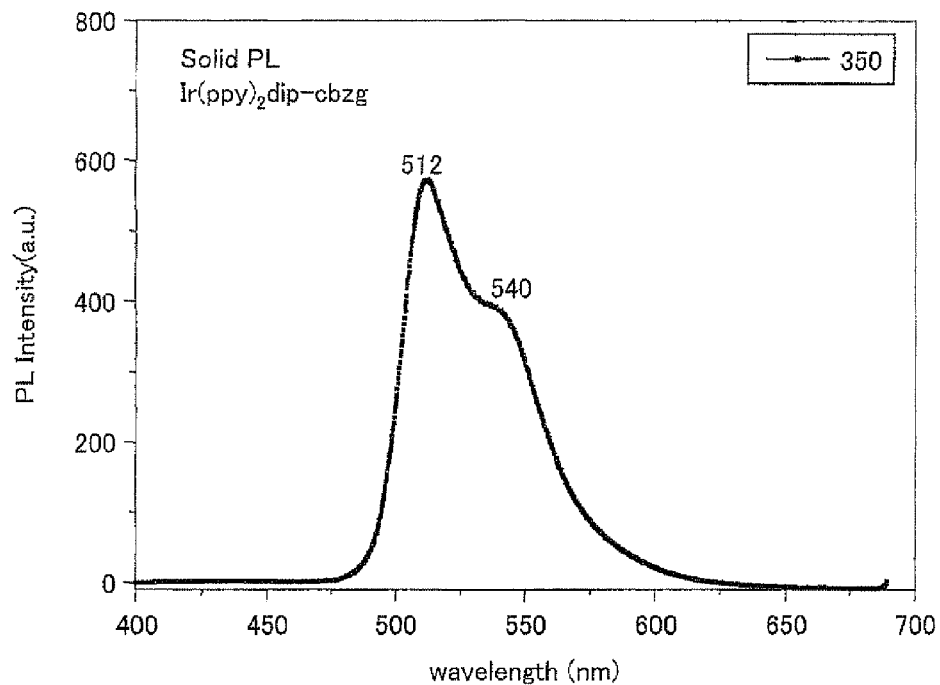
FIG. 43 shows a graph of a PL spectrum of the compound of FIG. 41 observed in a solid-phase state.

FIG. 43 shows a PL spectrum of the Ir(ppy)$_2$dip-cbzg observed in a solid-phase state. Photoluminescence of the Ir(ppy)$_2$dip-cbzg in a solid-phase state exhibited a maximum value at a wavelength of 512 nm.

Example 18

Synthesis of Ir(dfppy)$_2$dip-cbzg, and Measurement of Absorption and Photoluminescence of Ir(dfppy)$_2$dip-cbzg (Synthesis of Ir(dfppy)$_2$dip-cbzg)

In a 100-ml flask, 10 ml of THF containing carbazol (67 mg, 0.4 mmol), and a hexane solution of n-BuLi (2.77 M, 0.4 mmol, 0.14 ml) were added and stirred in argon atmosphere at a room temperature for about 2 hours. Then, N,N'-diisopropyl carbodiimide (50 mg, 0.4 mmol) was dropped into an obtained reactant solution. The reactant solution was quickly stirred for 2 hours, and then dropped into 15 ml of THF containing [(dfppy)$_2$Ir(μ-Cl)]$_2$ (0.2 mmol, 220 mg), and stirred at 80° C. for 12 hours.

Subsequently, an obtained reactant was cooled down to a room temperature, and then, the solvent was vaporized under a reduced pressure. A resultant product was washed with diethyl ether, thereby preparing a novel iridium complex, Ir(dfppy)$_2$dip-cbzg, according to the present invention. A yield thereof was 70%. The novel iridium complex thus obtained was subjected to NMR analysis, so as to confirm that it was an intended compound. The following shows a result of the analysis.

$^1$H NMR (300 MHz, CD$_2$Cl$_2$, rt): δ=9.45 (d, 2H), 8.25 (d, 2H), 7.99 (d, 2H), 7.84 (t, 2H), 7.49-7.37 (m, 6H), 7.20 (dt, 2H), 6.29 (t, 2H), 5.71 (dd, 2H), 2.95-2.89 (m, 2H), 0.54 (d, 6H), −0.17 (d, 6H).

(Measurement of Absorption Spectrum and PL Spectrum)

The measurement of an absorption spectrum and a PL spectrum of the obtained novel iridium complex was carried out in the same manner as in Example 2.

Figure 44:
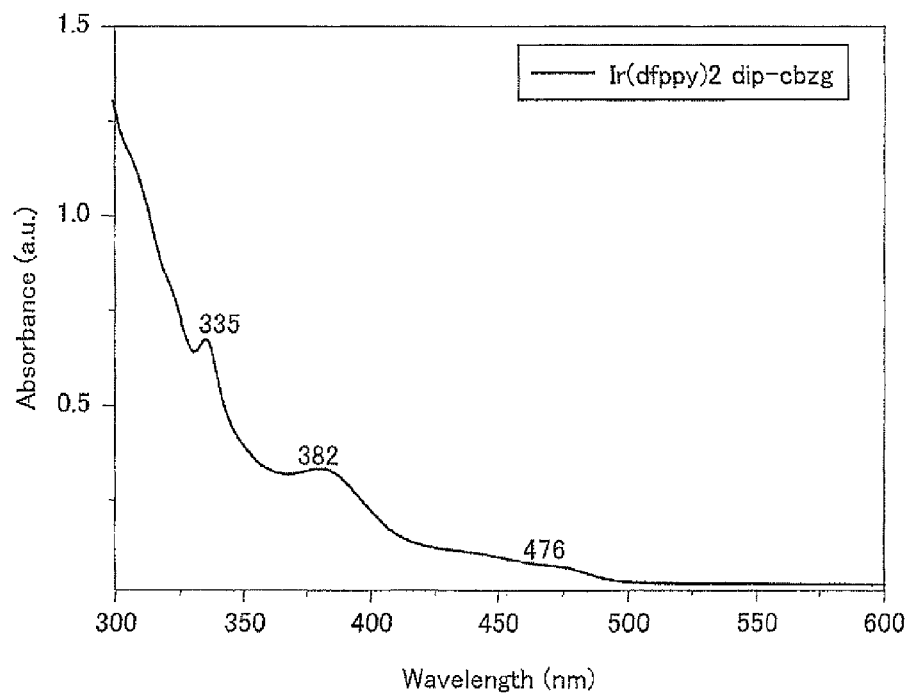
FIG. 44 shows a graph of a UV-vis absorption spectrum of another compound according to the present invention observed in chloroform.

FIG. 44 shows a UV-vis absorption spectrum of the Ir(dfppy)$_2$dip-cbzg observed in a chloroform solution.

Figure 45:
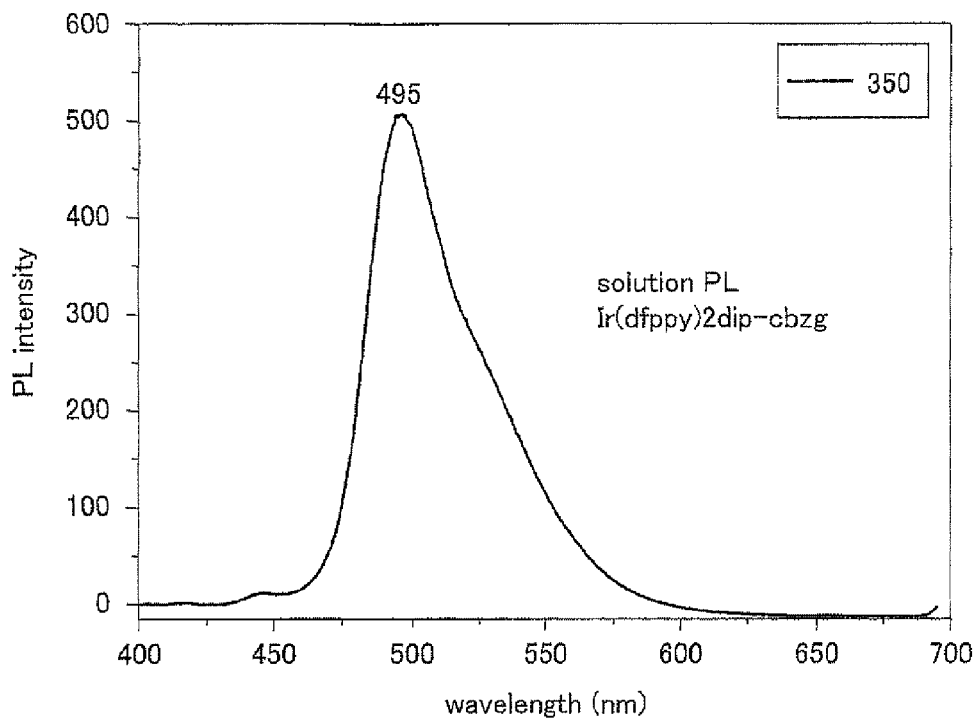
FIG. 45 shows a graph of a PL spectrum of the compound of FIG. 44 observed in chloroform.

FIG. 45 shows a PL spectrum of the Ir(dfppy)$_2$dip-cbzg observed in a chloroform solution. Photoluminescence of the Ir(dfppy)$_2$dip-cbzg in a chloroform solution exhibited a maximum value at a wavelength of 495 nm.

Figure 46:
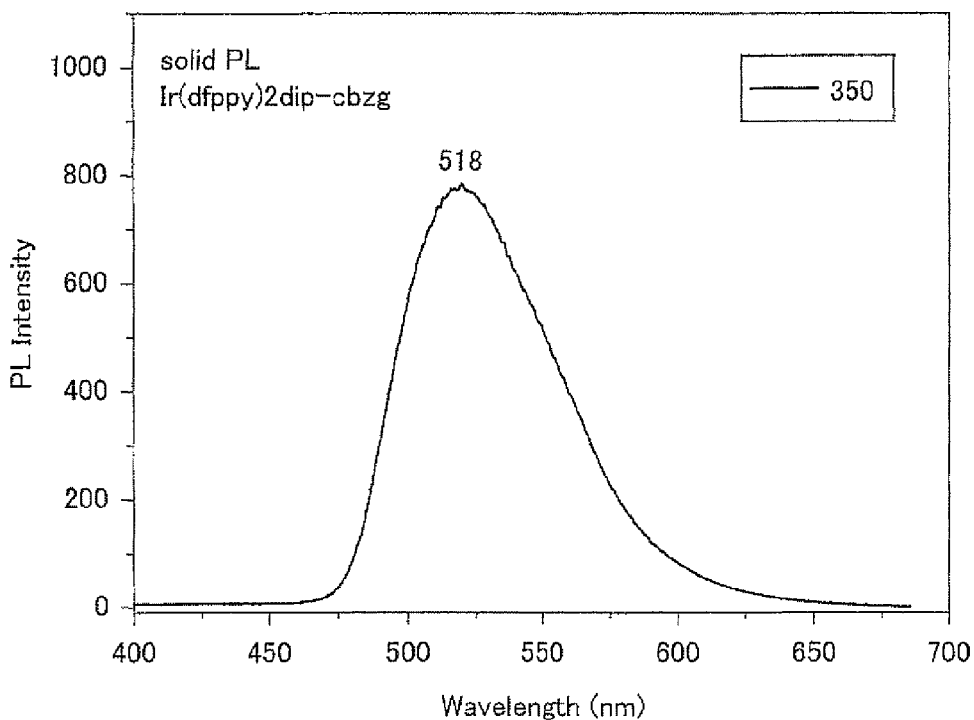
FIG. 46 shows a graph of a PL spectrum of the compound of FIG. 44 observed in a solid-phase state.

FIG. 46 shows a PL spectrum of the Ir(dfppy)$_2$dip-cbzg observed in a solid-phase state. Photoluminescence of the Ir(dfppy)$_2$dip-cbzg in a solid-phase state exhibited a maximum value at a wavelength of 518 nm.

Example 19

Synthesis of Ir(ppy)$_2$dip-fla, Measurement of Absorption and Photoluminescence of Ir(ppy)$_2$dip-fla (Synthesis of Ir(ppy)$_2$dip-fla)

In a 100-ml flask, 10 ml of THF containing fluorene (66 mg, 0.4 mmol), and a hexane solution of n-BuLi (2.77 M, 0.4 mmol, 0.14 ml) were added and stirred in argon atmosphere at a room temperature for 2 hours. Then, N,N'-diisopropyl carbodiimide (50 mg, 0.4 mmol) was dropped into an obtained reactant solution. The reactant solution was quickly stirred for two hours. Then, the reactant solution was dropped into 15 ml of THF containing [(ppy)$_2$Ir(μ-Cl)]$_2$ (0.2 mmol, 220 mg), and stirred at 80° C. for 12 hours.

Subsequently, an obtained reactant was cooled down to a room temperature, and the solvent was vaporized under a reduced pressure. Then, a resultant product was washed with diethyl ether, thereby preparing a novel iridium complex, Ir(ppy)$_2$dip-fla, according to the present invention. A yield thereof was 60%. The novel iridium complex thus obtained was subjected to NMR analysis, so as to confirm that it was an intended compound. The following shows a result of the analysis.

$^1$H NMR (300 MHz, CDCl$_3$, rt): δ=9.46 (d, 1H), 9.22 (d, 1H), 7.92 (d, 1H), 7.78-7.74 (, 5H), 7.68 (t, 1H), 7.61 (t, 3H), 7.48-7.40 (m, 4H), 7.37 (d, 2H), 6.81 (t, 1H), 6.70 (dd, 2H), 6.59 (t, 1H), 6.34 (dd, 2H), 4.93 (s, 1H), 4.13-4.09 (m, 1H), 2.16-2.12 (m, 1H), 0.88 (d, 3H), 0.35 (d, 3H), 0.09 (d, 3H), −0.74 (d, 3H).

(Measurement of Absorption Spectrum and PL Spectrum)

The measurement of an absorption spectrum and a PL spectrum of the obtained novel iridium complex was carried out in the same manner as in Example 2.

Figure 47:
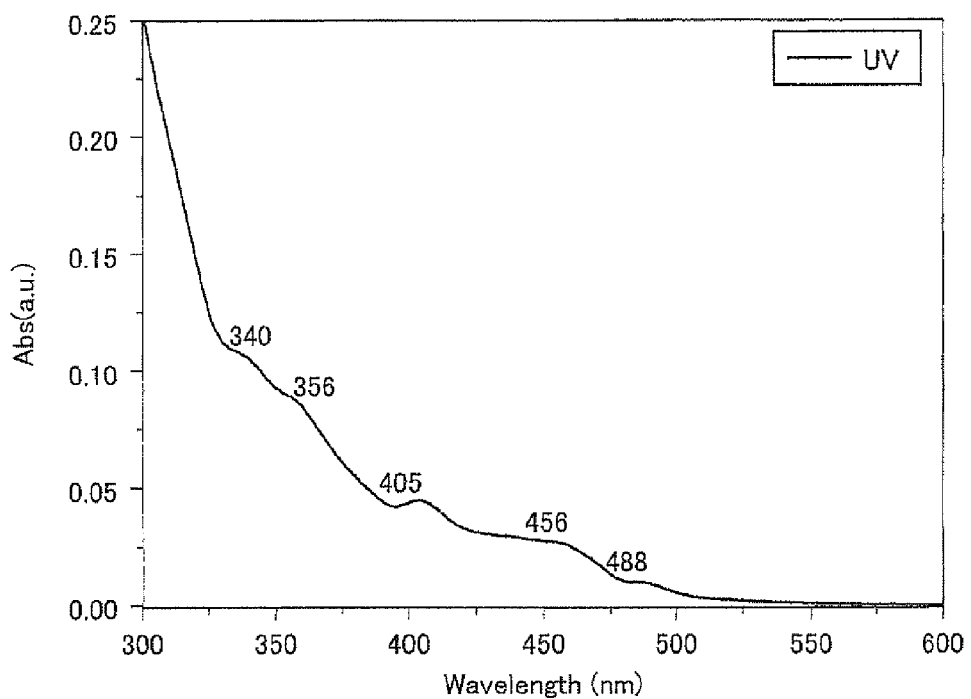
FIG. 47 shows a graph of a UV-vis absorption spectrum of another compound according to the present invention observed in chloroform.

FIG. 47 shows a UV-vis absorption spectrum of the Ir(ppy)$_2$dip-fla observed in a chloroform solution.

Figure 48:
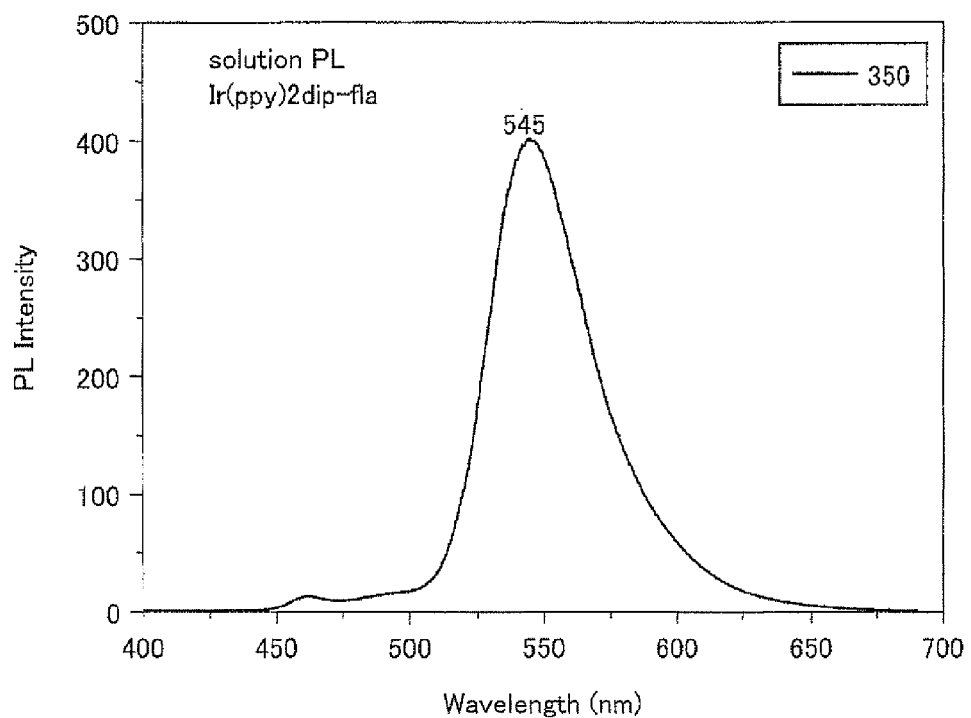
FIG. 48 shows a graph of a PL spectrum of the compound of FIG. 47 observed in chloroform.

FIG. 48 shows a PL spectrum of the Ir(ppy)$_2$dip-fla observed in a chloroform solution. Photoluminescence of the Ir(ppy)$_2$dip-fla in a chloroform solution exhibited a maximum value at a wavelength of 545 nm.

Figure 49:
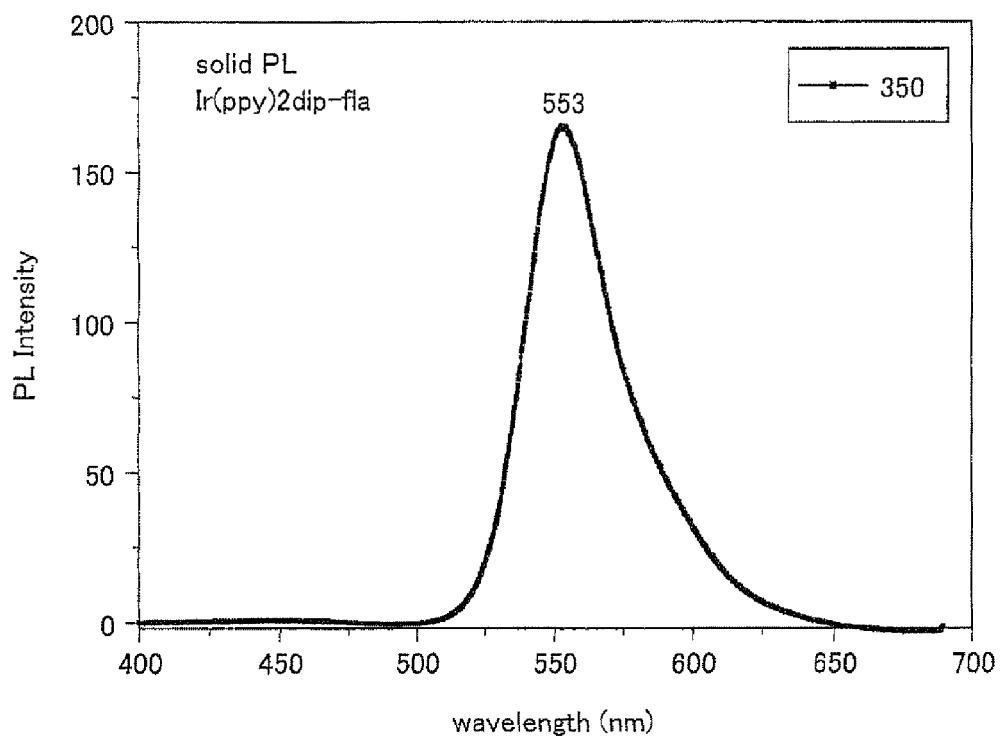
FIG. 49 shows a graph of a PL spectrum of the compound of FIG. 47 observed in a solid-phase state.

FIG. 49 shows a PL spectrum of the Ir(ppy)$_2$dip-fla observed in a solid-phase state. Photoluminescence of the Ir(ppy)$_2$dip-fla in a solid-phase state exhibited a maximum value at a wavelength of 553 nm.

Example 20

Synthesis of Ir(ppy)$_2$dip-dpp, and Measurement of Absorption and Photoluminescence of Ir(ppy)$_2$dip-dpp (Synthesis of Ir(ppy)$_2$dip-dpp)

Synthesis was carried out in the same manner as in Example 19 except that THF containing diphenyl phosphine (74 mg, 0.4 mmol) was used instead of the THF containing fluorene (66 mg, 0.4 mmol).

An obtained product was washed with diethyl ether, thereby preparing a novel iridium complex, Ir(ppy)$_2$dip-dpp, according to the present invention. A yield thereof was 60%. The novel iridium complex thus obtained was subjected to NMR analysis, so as to confirm that it was an intended compound. The following shows a result of the analysis.

$^1$H NMR (300 MHz, CDCl$_3$, rt): δ=8.70 (d, 1H), 8.60 (d, 1H), 7.82 (d, 1H), 7.55-7.65 (m, 3H), 7.35-7.48 (m, 2H), 7.38 (d, 2H), 7.14 (d, 1H), 7.08 (d, 2H), 6.90 (t, 1H), 6.62-6.75 (m, 5H), 6.35-6.60 (m, 6H), 5.95 (t, 1H), 4.13 (m, 1H), 3.61 (m, 1H), 0.90 (d, 3H), 0.61 (d, 3H), 0.45 (d, 3H), 0.15 (d, 3H).

(Measurement of Absorption Spectrum and PL Spectrum)

The measurement of an absorption spectrum and a PL spectrum of the obtained novel iridium complex was carried out in the same manner as in Example 2.

Figure 50:
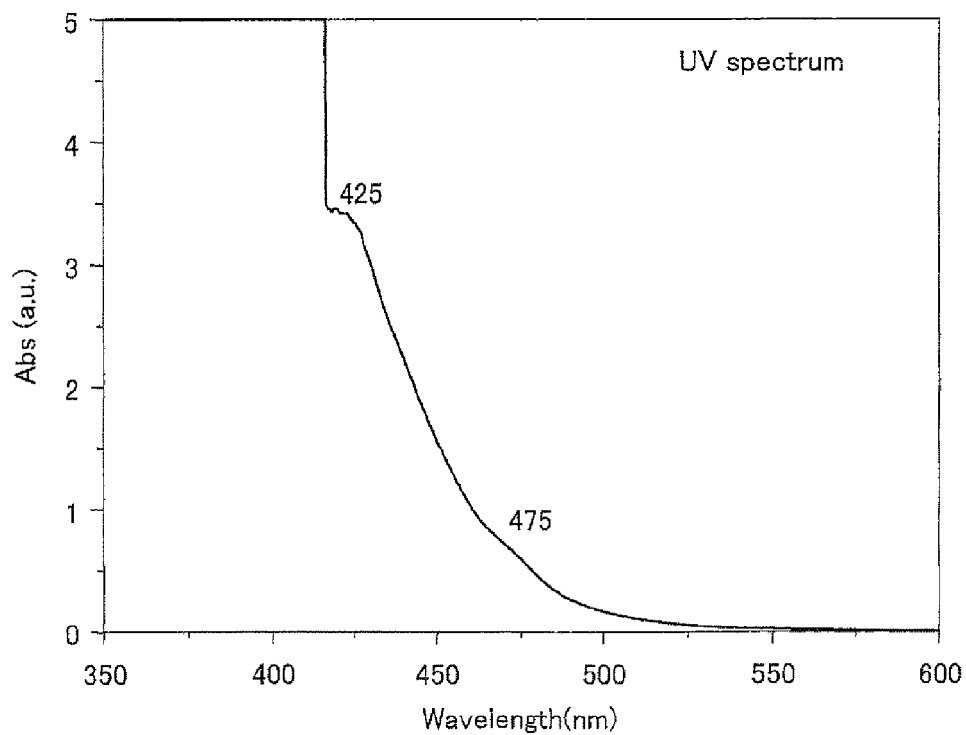
FIG. 50 shows a graph of a UV-vis absorption spectrum of another compound according to the present invention observed in chloroform.

FIG. 50 shows a UV-vis absorption spectrum of the Ir(ppy)$_2$dip-dpp observed in a chloroform solution.

Figure 51:
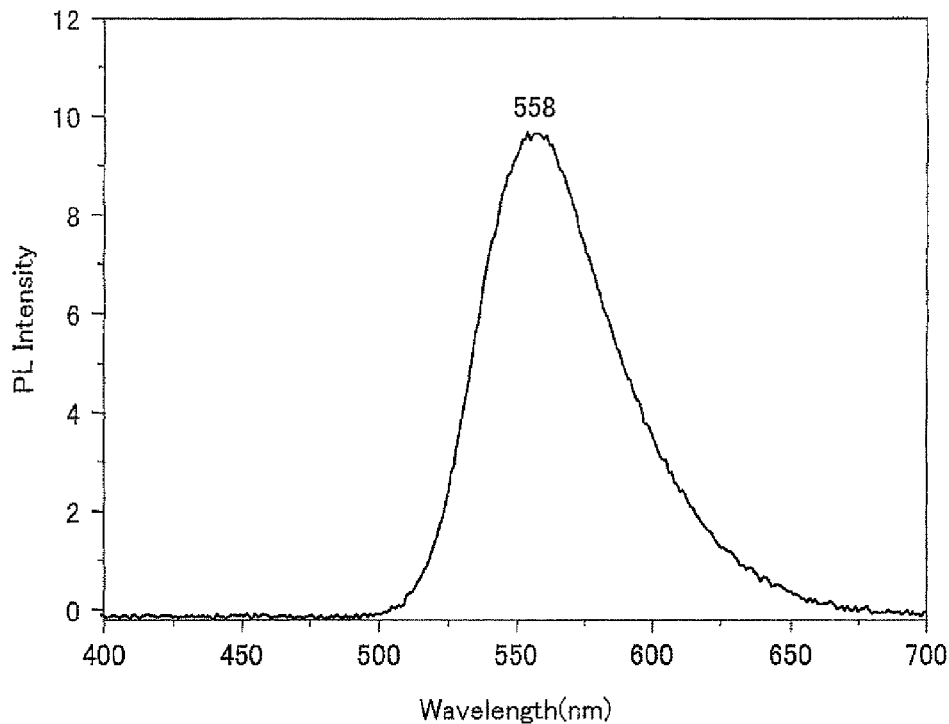
FIG. 51 shows a graph of a PL spectrum of the compound of FIG. 50 observed in chloroform.

FIG. 51 shows a PL spectrum of the Ir(ppy)$_2$dip-dpp observed in a chloroform solution. Photoluminescence of the Ir(ppy)$_2$dip-dpp in a chloroform solution exhibited a maximum value at a wavelength of 558 nm.

Figure 52:
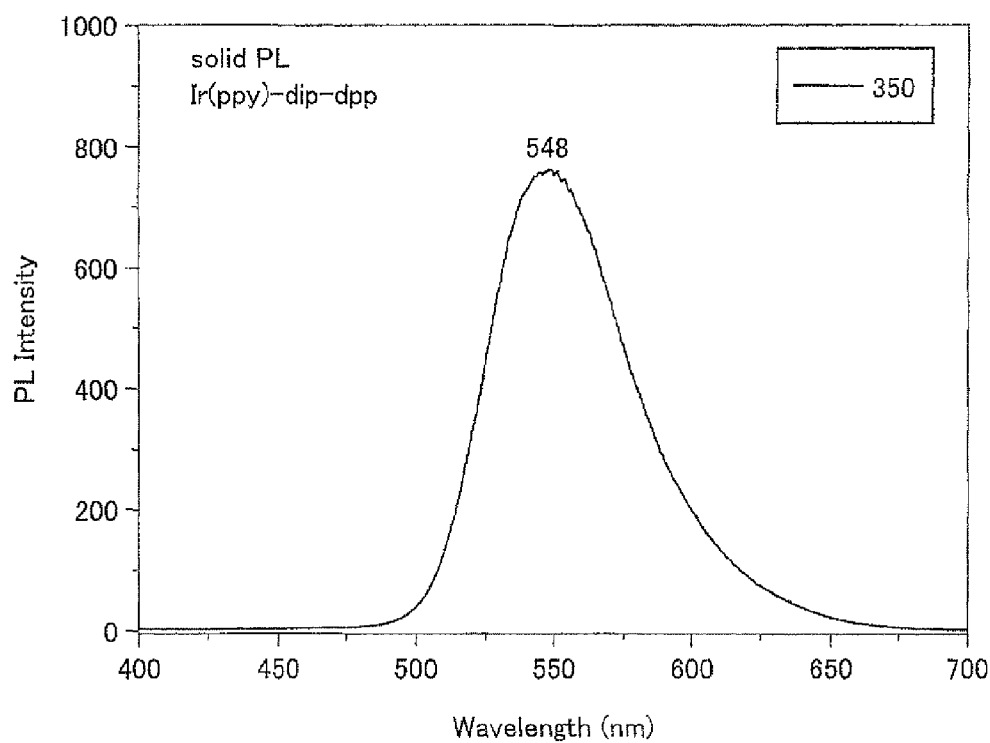
FIG. 52 shows a graph of a PL spectrum of the compound of FIG. 50 observed in a solid-phase state.

FIG. 52 shows a PL spectrum of the Ir(ppy)$_2$dip-dpp observed in a solid-phase state. Photoluminescence of the Ir(ppy)$_2$dip-dpp in a solid-phase state exhibited a maximum value at a wavelength of 548 nm.

INDUSTRIAL APPLICABILITY

According to the present invention, it is possible to provide (i) a novel compound that exhibits a practically sufficient light-emitting property not only in a case where the novel compound is used as a luminescent dopant but also in a case where the novel compound is used solely, (ii) a light-emission method using the compound, and (iii) a light-emitting device using the compound. The present invention is applicable to, for example, a detection marker, or a luminescent material for use in an organic electroluminescence device.

The invention claimed is:

1. A compound represented by the following general formula (1):

[Chem. 1]

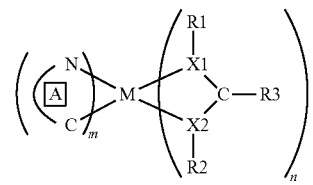

(1)

wherein C^N (indicated by A) represents a cyclometalating ligand,

M represents a transition metal atom,

X1 represents a nitrogen atom or a sulfur atom,

X2 represents a nitrogen atom, a sulfur atom, or a phosphorous atom, wherein the phosphorous atom is connected to two R1 or two R2 respectively, R1 and R2 each independently represent a straight, branched, or cyclic alkyl group, an aryl group, an aralkyl group, or an ether group, which groups may have a substituent, R3 represents a straight, branched, or cyclic alkyl group, an alkenyl group, an alkynyl group, an aryl group, an aralkyl group, an aliphatic, aromatic, or cyclic amino group, a phosphino group, a boryl group, an alkylthio group, an arylthio group, an alkoxy group, an aryloxy group, an ether group, or an imino group, which groups may have a substituent, and m and n each independently represent an integer of not less than 1, and a total of m and n is not more than the largest number of ligands that can coordinate with M.

2. A compound represented by the following general formula (2):

[Chem. 2]

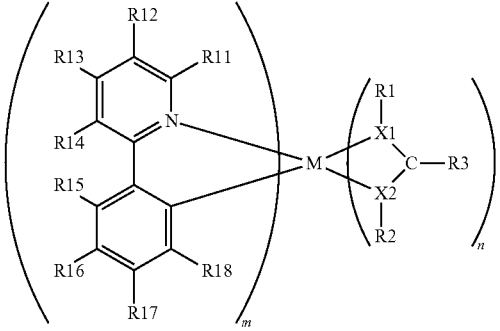

(2)

wherein M represents a transition metal atom,

X1 and X2 each independently represent a nitrogen atom, a sulfur atom, or a phosphorous atom, wherein the phosphorous atom is connected to two R1 or two R2 respectively, R1 and R2 each independently represent a straight, branched, or cyclic alkyl group, an aryl group, an aralkyl group, or an ether group, which groups may have a substituent, R3 represents a straight, branched, or cyclic alkyl group, an alkenyl group, an alkynyl group, an aryl group, an aralkyl group, an aliphatic, aromatic, or cyclic amino group, a phosphino group, a boryl group, an alkylthio group, an arylthio group, an alkoxy group, an aryloxy group, an ether group, or an imino group, which groups may have a substituent, R11, R12, R13, R14, R15, R16, R17, and R18 each independently represent a hydrogen atom, a halogen atom, or a C1 to C10 hydrocarbon group; at least one hydrogen included in the hydrocarbon group may be substituted with a halogen atom; in a case where the hydrocarbon group includes at least two carbon atoms, the at least two carbon atoms may be partially substituted with a sulfur atom or a nitrogen atom; and hydrocarbon groups may be connected to each other so as to form a ring, and m and n each independently represent an integer of not less than 1, and a total of m and n is not more than the largest number of ligands that can coordinate with M.

3. A compound represented by the following general formula (3):

[Chem. 3]

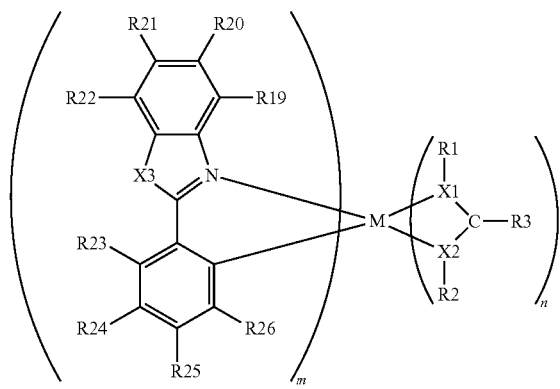

(3)

wherein M represents a transition metal atom,

X1 and X2 each independently represent a nitrogen atom, a sulfur atom, or a phosphorous atom, wherein the phosphorous atom is connected to two R1 or two R2 respectively, X3 represents a sulfur atom or an oxygen atom, R1 and R2 each independently represent a straight, branched, or cyclic alkyl group, an aryl group, an aralkyl group, or an ether group, which groups may have a substituent, R3 represents a straight, branched, or cyclic alkyl group, an alkenyl group, an alkynyl group, an aryl group, an aralkyl group, an aliphatic, aromatic, or cyclic amino group, a phosphino group, a boryl group, an alkylthio group, an arylthio group, an alkoxy group, an aryloxy group, an ether group, or an imino group, which groups may have a substituent, R19, R20, R21, R22, R23, R24, R25, and R26 each independently represent a hydrogen atom, a halogen atom, or a C1 to C10 hydrocarbon group; at least one hydrogen included in the hydrocarbon group may be substituted with a halogen atom; in a case where the hydrocarbon group includes at least two carbon atoms, the at least two carbon atoms may be partially substituted with a sulfur atom or a nitrogen atom; hydrocarbon groups may be connected to each other so as to form a ring, and m and n each independently represent an integer of not less than 1, and a total of m and n is not more than the largest number of ligands that can coordinate with M.

4. The compound as set forth in claim 3, wherein M represents iridium, X1 and X2 each represent a nitrogen atom, and X3 represents a sulfur atom.

5. The compound as set forth in claim 2, wherein M represents iridium, and X1 and X2 each represent a nitrogen atom in the general formula (2).

6. A light-emitting method for causing a compound as set forth in claim 2 to emit light by applying a voltage thereto.

7. A light-emitting method for causing a compound as set forth in claim 3 to emit light by applying a voltage thereto.

8. A light-emitting device comprising:
a pair of electrodes;
an emitting layer containing a luminescent material and provided between the pair of electrodes, the emitting layer containing a compound as set forth in claim 2.

9. A light-emitting device comprising:
a pair of electrodes;
an emitting layer containing a luminescent material and provided between the pair of electrodes, the emitting layer containing only the compound as set forth in claim 2 as the luminescent material.

10. A light-emitting device comprising:
a pair of electrodes;
an emitting layer containing a luminescent material and provided between the pair of electrodes, the emitting layer containing a compound as set forth in claim 3.

11. A light-emitting device comprising:
a pair of electrodes;
an emitting layer containing a luminescent material and provided between the pair of electrodes, the emitting layer containing only the compound as set forth in claim 3 as the luminescent material.

12. A compound represented by the following general formula (1):

[Chem. 1]

(1)

wherein C^N (indicated by A) represents a cyclometalating ligand,

M represents an iridium atom,

X1 and X2 each independently represent a nitrogen atom,

R1 and R2 each independently represent a straight, branched, or cyclic alkyl group, an aryl group, an aralkyl group, or an ether group, which groups may have a substituent, R3 represents a straight, branched, or cyclic alkyl group, an alkenyl group, an alkynyl group, an aryl group, an aralkyl group, an aliphatic, aromatic, or cyclic amino group, a phosphino group, a boryl group, an alkylthio group, an arylthio group, an alkoxy group, an aryloxy group, an ether group, or an imino group, which groups may have a substituent, and m and n each independently represent an integer of not less than 1, and a total of m and n is not more than the largest number of ligands that can coordinate with M.

13. A light-emitting method for causing a compound to emit light by applying a voltage thereto, wherein the compound is represented by the following general formula (1):

[Chem. 1]

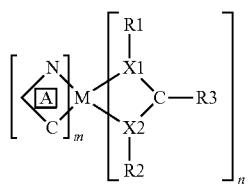

(1)

wherein C^N (indicated by A) represents a cyclometalating ligand,

M represents a transition metal atom,

X1 and X2 each independently represent a nitrogen atom, a sulfur atom, or a phosphorous atom, wherein the phosphorous atom is connected to two R1 or two R2 respectively, R1 and R2 each independently represent a straight, branched, or cyclic alkyl group, an aryl group, an aralkyl group, or an ether group, which groups may have a substituent, R3 represents a straight, branched, or cyclic alkyl group, an alkenyl group, an alkynyl group, an aryl group, an aralkyl group, an aliphatic, aromatic, or cyclic amino group, a phosphino group, a boryl group, an alkylthio group, an arylthio group, an alkoxy group, an aryloxy group, an ether group, or an imino group, which groups may have a substituent, and m and n each independently represent an integer of not less than 1, and a total of m and n is not more than the largest number of ligands that can coordinate with M.

14. A light-emitting device comprising:

a pair of electrodes;

an emitting layer containing a luminescent material and provided between the pair of electrodes, the emitting layer containing a compound represented by the following general formula (1):

[Chem. 1]

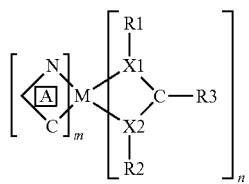

(1)

wherein C^N (indicated by A) represents a cyclometalating ligand,

M represents a transition metal atom,

X1 and X2 each independently represent a nitrogen atom, a sulfur atom, or a phosphorous atom, wherein the phosphorous atom is connected to two R1 or two R2 respectively, R1 and R2 each independently represent a straight, branched, or cyclic alkyl group, an aryl group, an aralkyl group, or an ether group, which groups may have a substituent, R3 represents a straight, branched, or cyclic alkyl group, an alkenyl group, an alkynyl group, an aryl group, an aralkyl group, an aliphatic, aromatic, or cyclic amino group, a phosphino group, a boryl group, an alkylthio group, an arylthio group, an alkoxy group, an aryloxy group, an ether group, or an imino group, which groups may have a substituent, and m and n each independently represent an integer of not less than 1, and a total of m and n is not more than the largest number of ligands that can coordinate with M.

15. A light-emitting device comprising:

a pair of electrodes;

an emitting layer containing a luminescent material and provided between the pair of electrodes, the emitting layer containing only a compound represented by the following general formula (1) as the luminescent material:

[Chem. 1]

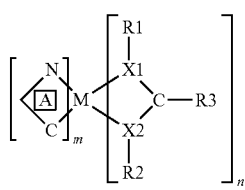

(1)

wherein C^N (indicated by A) represents a cyclometalating ligand, M represents a transition metal atom, X1 and X2 each independently represent a nitrogen atom, a sulfur atom, or a phosphorous atom, wherein the phosphorous atom is connected to two R1 or two R2 respectively, R1 and R2 each independently represent a straight, branched, or cyclic alkyl group, an aryl group, an aralkyl group, or an ether group, which groups may have a substituent, R3 represents a straight, branched, or cyclic alkyl group, an alkenyl group, an alkynyl group, an aryl group, an aralkyl group, an aliphatic, aromatic, or cyclic amino group, a phosphino group, a boryl group, an alkylthio group, an arylthio group, an alkoxy group, an aryloxy group, an ether group, or an imino group, which groups may have a substituent, and m and n each independently represent an integer of not less than 1, and a total of m and n is not more than the largest number of ligands that can coordinate with M.

* * * * *